US007771937B2

(12) United States Patent
Moon et al.

(10) Patent No.: US 7,771,937 B2
(45) Date of Patent: Aug. 10, 2010

(54) METHODS FOR PREDICTING LATE ONSET ALZHEIMER DISEASE IN AN INDIVIDUAL

(75) Inventors: Randall Todd Moon, Kenmore, WA (US); Giancarlo De Ferrari, Concepcion (CL)

(73) Assignee: University of Washington, Seattle, WA (US)

( * ) Notice: Subject to any disclaimer, the term of this patent is extended or adjusted under 35 U.S.C. 154(b) by 264 days.

(21) Appl. No.: 11/133,918

(22) Filed: May 20, 2005

(65) Prior Publication Data

US 2006/0263791 A1 Nov. 23, 2006

(51) Int. Cl.
*C07H 21/04* (2006.01)
*C12Q 1/68* (2006.01)
(52) U.S. Cl. .................. 435/6; 435/91.1; 435/91.2; 536/23.1; 536/24.3
(58) Field of Classification Search .................. None
See application file for complete search history.

(56) References Cited

U.S. PATENT DOCUMENTS

| 6,156,311 | A | 12/2000 | Strickland et al. ......... 424/130.1 |
| 6,342,350 | B1 | 1/2002 | Tanzi et al. ..................... 435/6 |
| 6,447,775 | B1 | 9/2002 | Strickland et al. ......... 424/130.1 |
| 2001/0052137 | A1 | 12/2001 | Klein |
| 2002/0187474 | A1 | 12/2002 | Comings et al. ............... 435/6 |
| 2003/0092019 | A1* | 5/2003 | Meyer et al. .................... 435/6 |
| 2004/0053251 | A1 | 3/2004 | Pericak-Vance et al. ....... 435/6 |
| 2004/0067512 | A1 | 4/2004 | Becker et al. ................... 435/6 |
| 2005/0014170 | A1 | 1/2005 | Weinberger et al. ............ 435/6 |

FOREIGN PATENT DOCUMENTS

| JP | 11279066 A | 10/1999 |
| WO | 97/41854 A1 | 11/1997 |
| WO | 02/092000 A2 | 11/2002 |
| WO | 2004/005534 A2 | 1/2004 |

OTHER PUBLICATIONS

Genecards, http://www.genecards.org/cgi-bin/carddisp.pl?gene=LRP6&search=lrp6.*
Mani et al. (Science, vol. 315, pp. 1278-1282, Mar. 2, 2007).*
Van Meurs et al. (J. of Bone and Mineral Research, vol. 21, No. 1, pp. 141-150, Sep. 6, 2005.*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
DeFerrari et al. (PNAS, vol. 104, No. 22, pp. 9434-9439, May 2007).*
Thisted (May 1998).*
Lucentini (The Scientist; 2004, vol. 24, p. 20).*
Abu-Khalil, A. et al., "Wnt Genes Define Distinct Boundaries in the Developing Human Brain: Implications for Human Forebrain Patterning," *J Comp Neurol* 474: 276-88, 2004.

Alberdi, E. et al., "Pigment epithelium-derived factor (PEDF) binds to glycosaminoglycans: analysis of the binding site," *Biochem*, Jul. 28, 1998, 37(30):10643-52; Erratum in: Biochemistry Dec. 22, 1998; 37(51):18128.
Alberdi, E. et al., "Binding of pigment epithelium-derived factor (PEDF) to retinoblastoma cells and cerebellar granule neurons. Evidence for a PEDF receptor," *J Biol Chem*. 274(44), 31605-12, 1999.
Alvarez, G. et al., "Regulation of tau phosphorylation and protection against β-amyloid-induced neurodegeneration by lithium. Possible implications for Alzheimer's disease," *Bipolar Disorders*, 2002, 4, 153-165.
Aymerich, M. S. et al., "Evidence for Pigment Epithelium-Derived Factor Receptors in the Neural Retina," *Invest Ophthalmol Vis Sci*. 42(13): 3287-93, 2001.
Bertram and Tanzi, "The Current Status of Alzheimer's Disease Genetics: What Do We Tell the Patients?" *Pharmacological Research* 50: 385-396, 2004.
Blacker et al., "ApoE-4 and Age at Onset of Alzheimer's Disease: The NIMH Genetics Initiative," *Neurology* 48: 139-147, 1997.
Blacker, D. et al., "Results of a high-resolution genome screen of 437 Alzheimer's Disease families," *Hum Mol Genet* 12: 23-32, 2003.
Brown, S. D. et al., "Isolation and Characterization of LRP6, a Novel Member of the Low Density Lipoprotein Receptor Gene Family," *Biochem Biophys Res Commun* 248: 879-88, 1998.
Caricasole, A. et al., "Induction of Dickkopf-1, a Negative Modulator of the Wnt Pathway, Is Associated with the Neuronal Degeneration in Alzheimer's Brain," *J. of Neuroscience* 24: 6021-6027, 2004.
Caricasole, A. et al., "The Wnt pathway, cell-cycle activation and β-amyloid: novel therapeutic strategies in Alzheimer's disease?" *Trends Pharmacol Sci* 24(5):233-8, 2003.
Chong, Z. Z. et al., "Targeting WNT, protein kinase B, and mitochondrial membrane integrity to foster cellular survival in the nervous system," *Histol Histopathol*, 2004, 19, 495-504.
Chuang, D-M. et al., "Neuroprotective Effects of Lithium in Cultured Cells and Animal Models of Diseases," *Bipolar Disorders* 4: 129-136, 2002.
Clatworthy, A. E. et al., "Lack of Association of a Polymorphism in the Low-density Lipoprotein Receptor-Related Protein Gene with Alzheimer's Disease," *Arch. Neurol*. 54: 1289-1292, 1997.
Corder, E. H. et al., "Gene Dose of Apoliprotein E Type 4 Allele and the Risk of Alzheimer's Disease in Late Onset Families," *Science* 261: 921-3, 1993.
Daw, W. et al., "The Number of Trait Loci in Late-Onset Alzheimer's Disease," *Am. J. Hum. Genet*. 66: 196-204, 2000.
De Ferrari, G. V. et al., "Wnt signaling function in Alzheimer's disease," *Brain Res Brain Res Rev* 33: 1-12, 2000.
De Ferrari, G. V. et al., "Activation of Wnt signaling rescues neurodegeneration and behavioral impairments induced by β-amyloid fibrils," *Mol Psychiatry* 8: 195-208, 2003.
Gould, T. D. et al., "In Vivo Evidence in the Brain for Lithium Inhibition of Glycogen Synthase Kinase-3," *Neuropsychopharmacology* 29: 32-38, 2004.

(Continued)

*Primary Examiner*—Jeanine A Goldberg
(74) *Attorney, Agent, or Firm*—Nixon Peabody LLP

(57) ABSTRACT

Methods for diagnosis or prognosis of late onset Alzheimer disease in an individual are provided which comprise detecting at least one polymorphism of a low-density lipoprotein receptor related protein 6 gene.

7 Claims, 9 Drawing Sheets

OTHER PUBLICATIONS

He, X. et al., "LDL Receptor-Related Proteins 5 and 6 in Wnt/β-catenin Signaling: Arrows Point the Way," *Development* 131: 1663-1677, 2004.
Herz, J., "The LDL Receptor Gene Family: (Un)Expected Signal Transducers in the Brain,"*Neuron* 29: 571-81, 2001.
Herz, J. et al., "Coaxing the LDL Receptor Family into the Fold," *Cell* 112: 289-292, 2003.
Hollenbach, E. et al., "Confirmation of an Association Between a Polymorphism in Exon 3 of the Low-Density Lipoprotein Receptor-Related Protein Gene and Alzheimer's Disease," *Neurology* 50: 1905-1907, 1998.
Horvath, S. et al., "Family-Based Tests for Associating Haplotypes With General Phenotype Data: Application to Asthma Genetics," *Genet Epidemiol* 26: 61-9, 2004.
Issack, P. S. et al., "Altered Expression of Helix-Loop-Helix Transcriptional Regulators and Cyclin D1 in Wnt-1-transformed PC12 Cells," *Cell Growth Differ* 9: 837-45, 1998.
Jackson, G. R. et al., "Human Wild-type Tau interacts with *wingless* Pathway Components and Produces Neurofibrillary Pathology in *Drosphila*," *Neuron*, May 16, 2002, 34, 509-519.
Jarriault, S. et al., "Signalling downstream of activated mammalian Notch," *Nature* 377: 355-8, 1995.
Jeon, H. et al., "Implications for familial hypercholesterolemia from the structure of the LDL receptor YWTD-EGF domain pair," *Nat Struct Biol* 8: 499-504, 2001.
Jho, E-H. et al., "Wnt/β-Catenin/Tcf Signaling Induces the Transcription of Axin2, a Negative Regulator of the Signaling Pathway," *Mol Cell Biol* 22(4): 1172-83, 2002.
Jones, S. E. et al., "Modulated expression of secreted Frizzled-related proteins in human retinal degeneration," *NeuroReport*, Dec. 2000, 11(18), 3963-3967.
Kang, D. E. et al., "Genetic Association of the Low-Density Lipoprotein Receptor-Related Protein Gene (LRP), an Apolipoprotein E Receptor, with Late-Onset Alzheimer's Disease," *Neurology* 49: 56-61, 1997.
Kang, D. E. et al., "Modulation of amyloid β-protein clearance and Alzheimer's disease susceptibility by the LDL receptor-related protein pathway," *J Clin Invest* 106(9): 1159-66, 2000.
Kehoe, P. et al., "A full genome scan for late onset Alzheimer's disease," *Hum Mol Genet* 8: 237-45, 1999.
Krauter, K. et al., "A Second-Generation YAC Contig Map of Human Chromosome 12," *Nature* 377: 321-333, 1995.
Lake, S. L. et al., "Fami y-Based Tests of Association in the Presence of Linkage," *Am J Hum Genet* 67: 1515-25, 2000.
Lako, M. et al., "A novel mammalian Wnt gene, WNT8B, shows brain-restricted expression in early development, with sharply delimited expression boundaries in the developing forebrain," *Hum Mol Genet* 7: 813-22, 1998.
Lendon et al., "Genetic Association Studies Between Dementia of the Alzheimer's Type and Three Receptors for Apolipoprotein E in a Caucasian Population," *Neuroscience Letters* 222: 187-190, 1997.
Li, Y. et al., "Low-Density Lipoprotein Receptor Family," *Mol Neurobiol* 23: 53-67, 2001.
Liao, A. et al., "Genetic Association of an α2-Macroglobulin (Val100011e) Polymorphism and Alzheimer's Disease,"*Human Mol. Gen.* 7: 1953-1956, 1998.
Maretto, S. et al., "Mapping Wnt / β-catenin signaling during mouse development and in colorectal tumors," *Proc Natl Acad Sci USA* 100: 3299-304, 2003.
Marigo, V. et al., "Sonic hedgehog differentially regulates expression of GLI and GLI3 during limb development," *Dev Biol.* Nov. 25, 1996, 180(1), 273-83.
Marigo, V. et al., "Regulation of Patched by Sonic hedgehog in the developing neural tube," *Proc Natl Acad Sci USA* 93: 9346-9351, 1996.
Mayeux, R. et al., "Chromosome-12 Mapping of Late-Onset Alzheimer Disease among Caribbean Hispanics," *Am J Hum Genet* 70: 237-43, 2002.
Meyer, C et al., "Mapping the type I collagen-binding site on pigment epithelium-derived factor. Implications for its antiangiogenic activity," *J Biol Chem*, Nov. 22, 2002, 277(47), 45400-7.

Moon, R. T. et al., "Wnt and β-Cantenin Signalling: Diseases and Therapies," *Nature Reviews Genetics* 5: 689-699, 2004.
Mudher, A. et al., "Alzheimer's disease- do tauists and Baptists finally shake hands?", *Trends Neurosci* 25: 22-6, 2002.
Myers, A. et al., "Full Genome Screen for Alzheimer Disease: Stage II Analysis," *Am J Med Genet* 114, 235-44, 2002.
Nordstrom, T. et al., "Method Enabling Pyrosequencing on Double-Stranded DNA," *Anal Biochem* 282: 186-93, 2000.
Pericak-Vance, M. A. et al., "Complete Genomic Screen in Late-Onset Familial Alzheimer's Disease: Evidence for a New Locus on Chromosome 12," *JAMA* 278: 1237-1241, 1997.
Pericak-Vance et al., "Complete Genomic Screen in Late-Onset Familial Alzheimer's Disease," *Neurobiology of Aging* 19: S39-S42, 1998.
Phiel, C. J. et al., "GSK-3α regulates production of Alzheimer's disease amyloid-β peptides," *Nature*, May 22, 2003, 423, 435-439.
Pinson, K. I. et al., "An LDL-receptor-related protein mediates Wnt signaling in mice," *Nature* 407: 535-8, 2000.
Rabinowitz, D. et al., "A Unified Approach to Adjusting Association Tests for Population Admixture with Arbitrary Pedigree Structure and Arbitrary Missing Marker Information," *Hum Hered* 50: 211-23, 2000.
Robitaille, J. et al., "Mutant frizzled-4 disrupts retinal angiogenesis in familial exudative vitreoretinopathy," *Nat Genet* 32: 326-30, 2002.
Rogaeva et al., Evidence for an Alzheimer Disease Susceptibility Locus on Chromosome 12 and for Further Locus Heterogeneity, *JAMA* 280: 614-618, 1998.
Saunders, A. J. et al., "Genetic association of Alzheimer's disease with multiple polymorphisms in alpha-2-macroglobulin," *Hum Mol Genet* 12(21): 2765-76, 2003.
Scott, W. K. et al., "No Genetic Association Between the LRP Receptor and Sporadic or Late-Onset Familial Alzheimer's Disease," *Neurogenetica* 1: 179-183, 1998.
Scott, W. K. et al., "Fine Mapping of the Chromosome 12 Late-Onset Alzheimer Disease Locus: Potential Genetic and Phenotypic Heterogeneity," *Am J Hum Genet* 66: 922-32, 2000.
Tamai, K. et al., "LDL-Receptor-Related Proteins in Wnt Signal Transduction," *Nature* 407: 530-535, 2000.
Veeman, M. T. et al., "Zebrafish Prickle, a Modulator of Noncanonical Wnt/Fz Signaling, Regulates Gastrulation Movements," *Current Biology* 13: 680-685, 2003.
Veeman, M. T. et al., "A Second Canon: Functions and Mechanisms of β-Catenin-Independent Wnt Signaling," *Dev Cell.* 5: 367-377, 2003.
Wavrant-DeVrièze, F. et al., "Association Between the Low Density Lipoprotein Receptor-Related Protein (LRP) and Alzheimer's Disease," *Neuroscience Letters* 227: 68-70, 1997.
Wehrli, M. et al., "*arrow* encodes an LDL-receptor-related protein essential for Wingless signaling," *Nature* 407: 527-30, 2000.
Wu, W. S. et al., "Genetic Studies on Chromosome 12 in Late-Onset Alzheimer's Disease," *JAMA* 280: 619-622, 1998.
Yan, D. et al., "Elevated expression of *axin2* and *hnkd* mRNA provides evidence that Wnt / β-catenin signaling is activated in human colon tumors," *Proc Natl Acad Sci USA* 98: 14973-8, 2001.
Primer3 on the WWW, Whitehead Institute for Biomedical Research © 1996-2001 and 2004 http://frodo.wi.mit.edu/cgi-bin/primer3/primer3_www.cgi.
Alzheimer Research Forum, Alzforum: AlzGene © 1996-2006 http://www.alzforum.org/res/com/gen/alzgene/default.asp.
Bhat et al., "Glycogen Synthase Kinase 3: A Drug Target for CNS Therapies," J. Neurochem. 89(6):1313-1317 (2004).
Extended European Search Report for European Patent Application No. EP 06 75 9621 (Oct. 6, 2009).
Haga et al., "Gene-Based SNP Discovery as Part of the Japanese Millennium Genome Project: Identification of 190 562 Genetic Variations in the Human Genome," J. Hum. Genet. 47(11):605-610 (2002).
Haines et al., "Functional Candidate Genes in Age-Related Macular Degeneration: Significant Association with VEGF, VLDLR, and LRP6," Invest. Ophthalmol. Vis. Sci. 47(1):329-335 (2006).
Haines et al., "Genetic Examination of Functional Candidate Genes in Age Related Macular Degeneration," Invest. Ophthalmol. Vis. Sci. 45(Suppl. 2):U201, E-Abstract 3727 (2004).

Holmen et al., "Decreased BMD and Limb Deformities in Mice Carrying Mutations in Both Lrp5 and Lrp6," J. Bone Mineral Res. 19(12):2033-2040 (2004).

Li et al., "LRP6 Expression Promotes Cancer Cell Proliferation and Tumorigenesis by Altering β-Catenin Subcellular Distribution," Oncogene 23:9129-9135 (2004).

Malek et al., "Apolipoprotein E Allele-Dependent Pathogenesis: A Model for Age-Related Retinal Degeneration," PNAS 102(33):11900-11905 (2005).

Reference SNP (refSNP) Cluster Report NCBI Database Accession No. rs1012672, NCBI Assay ID ss28502576 (Aug. 20, 2004).

Su et al., "Lithium, A Common Drug for Bipolar Disorder Treatment, Regulates Amyloid-β Precursor Protein Precessing," Biochem. 43:6899-6908 (2004).

Van Meurs et al., "Common Genetic Variation in the Low-Density Lipoprotein Receptor-Related Protein 5 and 6 Genes Determines Fracture and Risk in Elderly White Men," J. Bone Mineral Res. 21(1):141-150 (2005).

* cited by examiner a b

1 ATGGGGGCCGTCCTGAGGAGCCTCCTGGCCTCTGCTCCTCCTGAGAGCCGGCCCCTTTGTTGCTTTATGCAAACAGACGGACTTGCCGATTGGTTGATGCTACA
AATGGCAAAGAGAATGCTACGATTGTAGTTGGAGGCTTGGAGGATGCAGCTGCGGTGGACTTTGTGTTTAGTCATGGCTTGATATACTGGAGTGATGTCAGCGAAGAAGCC
ATTAAACGAACAGAATTTAACAGAAACTGAGAGTTGCCCCCGATGGGCTGGCATGTGATTGGCTTGATTGGCTTGGAGAAAAATTGTACTGG
ACAGATTCGAAACTAATCGGATTGAAGTTCTAATTTAGATGGATCTTTACGAGAACGTGTCAAGAGAGTTGATCAACCCAGAGCTATTGCCTTAGATCCTTCA
AGTGGTTCATGTACTGACAGACAGTGGGAGAAGCTTTATTGAGGAGACTGCCAAAGATAGAACGTGCAAGACTTAATTTCATCCACAAATCAAATCGGATGGAACAAATCGGACAGCAGTGGTTAAAGGT
GGACTGACTTTGGATTATGAAGACAAAAGCTTTATTGAGGACATATTGTACTGACTGACAGAACCTTTGGCTTGCAACAAGTATACTGGTGAGGGTCTGCGT
TCCCTTCCACATCCTTTGCCTTGACGTTATTGACGTTATTGAGGATAGGCAGCCAACAGAGGCAGCCAAATCCATGTGGAATTGACAATGGGGTTGTTCCATTG
GAAATCCATTCTGACATCTGTCTGACATCTGTCTCCAGCCTTTTATCAGTGTGCTTGCCCCCAGAATTTACAGACCACCAGATTTCTTGATACACCCAGAGTCAAACTCCTGGAGAATGGAAAAACCTGCAAAGATGGTGCCACAGAATTATTGCTTTTTA
GCTCGAAGGACAGAGTTGAGACGCATTTCTTTGATACACCCAGATTTACAGACCACCAGATTTCTTGATACACCGCCATACGCCTAAGATCCGTCATTGCCATTGCCATCCTGATGGT
GAAGGCTACATCTACTGACTGATGAAGTGAGGGCCATACGCCGTCAGTTCAGTCAGTCTCGGACCATGAAGAAGCTCAATGGGAGACCTCAGTCAGTCTGATTTCAGAGGAC
ATTGCTGTGGACTGGGTTGCACGAAATCTTTATTGACAGGCTATTGGACCCATGGAGCTGACTGTATTGGGAGCTCTGGAGGTACATGTTTAGATCCCATGGTTGGGTACTGTATTGGACTGTATTGGGACTGGTTCTGACCGT
TTAGAGGAACCCCGGCTATTGTGTTTAGATCCATGGTTGGGTACATGTTTAGATCCGCCAAATGTTTAGCCTTGGATTATGATGAAGGCAAAATATACTGGGACTGTTACTTTGTTGGTGACTGTTAGCATT
GTAGTATTGGTTAACACTTCTCTTGGTTGTGTTAGATCCGCCAAATGTTTAGCCTTGGATTATGATGAAGGCAAAATATACTGGGACTGTTACTTTGTTGGTGACTGTTAGCATT
ACTGATGGCACTGGGAGACGAGTAGTGCAGAGAGGAAGTTCAGAGAGGAAGTGATCATAGACCAGCTGCCTGACCTCATGGGCCTAAGGCTACAATGTTCATCGAGTGATTGGTTCCAACCCCCTGT
GAAAGAGTTCATAAACGAGTGGGGATGTAGCCATCCTGCCTCTATAGACCTCAGGGCCTTCGCTGTGCTATTGCTTTGAACTCATCAGTGACATGAAGACCTGCATTGTC
CCAGAGGCTTCCTTTTGATGTGACAGAACAACCGAATTTATTCACGAGAGCAGCAGAATTTCTCTGGAAACAACAATAATAATGTGGCTATTCCACTCACTGCCTGTGTCAAAGAAGCTTCTGCT
TTGGATTTATGTGACAGAAGGCATGGCAGTAGACCGGCAGTAGACTCCCCAGAGCTCTGCGTTGGGAAGAACTTGTACTGGGCAGAGACCATGGGAAGAGCACCGACAA
GTTTTGGTGTGTGGAAAGACCTAGATAGTCCCCTAGTTCCAATGTGGGCGGGCAGCAGCGCCTAACTGACGGCCTGCCTCATCCTTTGCTTAACTCAGTAGCATTATATCTCACTCATCTCGACAGTCA
ATAGAATCTTCAAATATGCTGACGTGCCAACAAAACCAGTGCCAAAACCGCCACCATCATTCAGGCCATTGATTATGTGATGGACATCCTCGTCTTTCACTACTACTCTTTAATGCTGAC
CGACGGCAGCATTGAGCGTGCCTTCCAGCAATGCACTGCCTCCGCTCTGCTTGGCTGTGCCAGTTGGCGTTTGTTTGTTGATGCCTGACGTGATTGATAACAACCATGGTTGATTGATGAACAACATGATCCGAAAAACATGATCCGAAAAACATGATCCGAAAAGGCACAAGGCACAAGGCACACAGGAAGATGGCAGCCAGGGC
AACAGGACTTGTAGTGCTCCTACGACTTCCTGCTCTCAGTCAGAAGAGTGCCATCAACCATGGTGATTGATTGAACAACATGATCCGAAAACATGATCCGCTACATCTCCATCCAC
AGCCTTCGGAAATGTCCGGGCCATTGACTATGACCAGCTATGACCAGTTCCGAGTCAGAAATACAACCTGAAATACAACCTGAAATACAACCCGCTACATCTCCATCCAC
TTTACTGTGGTTGTGACAAGATTAGATGGAGATCAGTTGGAGTTGGAGTTGGAGTGCTGAAAGGCGAGCAGGAGCAGGACGACCTGAGCCATTGTGGTAAACCCAGAGAGAAAGGGTATATGTATTT
GTCATTAATGTGACAAGATTAGATGGAGATCAGTTGGAGTTGGAGTTGGAGTGCTGAAAGGCGAGCAGGAGCAGGACGACCTGAGCCATTGTGGTAAACCCAGAGAGAAAGGGTATATGTATTT
TACCAATCTTCAGGAA 3234

Complete DNA sequence of LRP6 gene (SEQ ID NO:1)
Nucleotides 1 to 3234

Figure 5A

3235
AGGTCTCCCTAAAAATTGAACGGGCTGCTTTGGATGGGACAGAACGGGAGGTCCTCTCTTTTTCAGTGGCTTAAGTAAACCAATTGCTTAGCCCTTGATAGCAGGCTGGGCAA
GCTCTTTTGGGCTGATTCAGATTCCGGCGAATTGAAAGCAGTGATCTTCAGGTGCTAACCGATAGTATTAGAAGACTCCAATATCTTGCAGCCTGTGGGACTTACTG
TGTTTGAAAACTGGCTCTATTGGATTGATAAACAGCAGCAAATGATTGAAAAATTGACATGAGAGGTAGAACCAAAGTCGAGACAGTGAGAACCAAAGTCGAACTCGAATTGCCCAGCTT
AGTGACATTCATGCAGTAAGGAGCTGAACCTTCAAGAACTACAGACAGCACCCTTGTCTGCAGGATAATGGTGGCTGTTCACATATTTGTCTTGTAAAGGGGATGGTAC
TACAAGGTGTTCTTGCCCCATGCAGCACCTGGTTCTACTTCAAGATGAGCTATCATGTGGAGAACCTCCAACATGTTCTCCTGACCAGTTACTTGTTTCACGGGGAAATTG
ACTGTATCCCGTGTGGCTTGGCGGTGCGATGGGTTTACTGAAGTGTGAAGACCACAGTGATGAACTCAATTGTCCCTGTATGCTCAGAGTCCCAGTTCCAGTGTGCCAGTGGG
CAGTGTATTGATGGTGCCCTCCGATGCAATGGAGATGCAAATGCCAGGAGAAATCAGATGAAGAAACTGTGAAGTGCTTTGTTTATTGATCAGTTCCGCTGTGCAA
TGGTCAGTGCATTGGAAAGCACAAGAAGTGTGATCATAATGTGCAGTGGATTCAGATGCAGTGATCAGATGAACAAGTCAGAAGAACTCAGATGAAGAACCAGCACCACAGGCCACCA
ATACAGTTGGTTCTGTTATTGGCGTAATTGTCACCATTTTTGTGTCTCTGGTTATGTCTGCCTCTGTTGTTATGTGACCAGAGAATGTGTGTCCACGTATGAAGGGAGATGGGGAAACT
ATGACTAATGACTATGTAGTTCATGGAGCAGTTCATCATGGGGAAGCAGTGGACCCCTATGACCGAGCCCATGTTACAGGAGCATCATCAAGTAGTCTTCAAGCACCAAAGGCACTTACTTCC
GTCAGCTCCCCTCAGTATCATGGGGAAGCAGTGGACCCCTATGACCGAGCCCATGTTACAGGAGCATCATCAAGTAGTCTTCAAGCACCAAAGGCACTTACTTCC
CTGCAATTTGAACCCCTGCACTTTGCACCCCACCACAGAGCGATCACATTACACTAGAAGAACCTGCAGCACCCCTGCAGCACAGCCCTGCAGCACAGATGTTTGTGACAGTGACAGTGACTATGCCTCGGAGAATGACCTCAGTGGCAACAGCCAAGGG
CCAATATAGCTACCGGCACTTGAACCTCATGATGACTATGATTCTTCATCACCTGAACTATGATTCAGAACTATGATTCTCATCACCTGAACTATGATTCAGAACTATGATTCTCATCACCTGAACTATGATTGAAACTATGAAAGCTGCCCACCTTCTCCAT
CTATACCAGTGACTTGAACTATGATTCTCATCACCTGAACTATGATTCAGAACTATGATTCTCATCACCTGAACTATGATTGAAACTATGAAAGCTGCCCACCTTCTCCAT
ACACAGAGAGAACTATTCTCATCACCTCTACCCACCGCCACCCCCTCCCCCGTACAGACTCCTCCTGA 4842

Complete DNA sequence of LRP6 gene (SEQ ID NO:1)
Nucleotides 3235 to 4842

Figure 5B

MGAVLRSLLACSFCVLLRAAPLLLYANRRDLRLVDATNGKENATIVVGGLEDAAAVDFVF
SHGLIYWSDVSEEAIKRTEFNKTESVQNVVSGLLSPDGLACDWLGEKLYWTDSETNRIE
VSNLDGSLRKVLFWQELDQPRAIALDPSSGFMWTDWGEVPKIERAGMDGSSRFIIINSE
IYWPNGLTLDYEEQKLYWADAKLNFIHKSNLDGTNRQAVVKGSLPHPFALTLFEDILYWT
DWSTHSILACNKYTGEGLREIHSDIFSPMDIHAFSQQRQPNATNPCGIDNGGCSHLCLMS
PVKPFYQCACPTGVKLLENGKTCKDGATELLLLARRTDLRRISLDTPDFTDIVLQLEDIR
HAIAIDYDPVEGYIYWTDDEVRAIRRSFIDGSGSQFVTAQIAHPDGIAVDWVARNLYWT
DTGTDRIEVTRLNGTMRKILISEDLEEPRAIVLDPMVGYMYWTDWGEIPKIERAALDGSD
RVVLVNTSLGWPNGLALDYDEGKIYWGDAKTDKIEVMNTDGTGRRVLVEDKIPHIFGFTL
LGDYVYWTDWQRRSIERVHKRSAEREVIIDQLPDLMGLKATNVHRVIGSNPCAEENGGCS
HLCLYRPQGLRCACPIGFELISDMKTCIVPEAFLLFSRRADIRRISLETNNNNVAIPLTG
VKEASALDFDVTDNRIYWTDISLKTISRAFMNGSALEHVVEFGLDYPEGMAVDWLGKNLY
WADTGTNRIEVSKLDGQHRQVLVWKDLDSPRALALDPAEGFMYWTEWGGKPKIDRAAMDG
SERTTLVPNVGRANGLTIDYAKRRLYWTDLDTNLIESSNMLGLNREVIADDLPHPFGLTQ
YQDYIYWTDWSRRSIERANKTSGQNRTIIQGHLDYVMDILVFHSSRQSGWNECASSNGHC
SHLCLAVPVGGFVCGCPAHYSLNADNRTCSAPTTFLLFSQKSAINRMVIDEQQSPDIILP
IHSLRNVRAIDYDPLDKQLYWIDSRQNMIRKAQEDGSQGFTVVVSSVPSQNLEIQPYDLS
IDIYSRYIYWTCEATNVINVTRLDGRSVGVVLKGEQDRPRAIVVNPEKGYMYFTNLQERS
PKIERAALDGTEREVLFFSGLSKPIALALDSRLGKLFWADSDLRRIESSDLSGANRIVLE
DSNILQPVGLTVFENWLYWIDKQQQMIEKIDMTGREGRTKVQARIAQLSDIHAVKELNLQ
EYRQHPCAQDNGGCSHICLVKGDGTTRCSCPMHLVLLQDELSCGEPPTCSPQQFTCFTGE
IDCIPVAWRCDGFTECEDHSDELNCPVCSESQFQCASGQCIDGALRCNGDANCQDKSDEK
NCEVLCLIDQFRCANGQCIGKHKKCDHNVDCSDKSDELDCYPTEEPAPQATNTVGSVIGV
IVTIFVSGTVYFICQRMLCPRMKGDGETMTNDYVVHGPASVPLGVYPHPSSLSGSLPGMS
RGKSMISSLSIMGGSSGPPYDRAHVTGASSSSSSTKGTYFPAILNPPPSPATERSHYTM
EFGYSSNSPSTHRSYSYRPYSYRHFAPPTPCSTDVCDSDYAPSRRMTSVATAKGYTSDL
NYDSEPVPPPTPRSQYLSAEENYESCPPSPYTERSYSHHLYPPPPSPCTDSS

Complete amino acid sequence of LRP6 protein (SEQ ID NO:2)

Figure 6

GGCTTTACTGTGGTTGTGAGCTCAGTTCCGAGTCAGAACCTGGAAATACAACCCTATGACCTCAGCATTGATATTTACAGCCGCTACATCTACTGGACTTGTGAGC
CTACCAATGTCATTAATGTGACAAGATTAGATGGGAGATCAGTTGGAGTGGTGCTGAAGGGCGAGCAGGACAGACCTCGAGCCATTGTGTGGTAAACCCAGAGAAAG(

Sequence of exon 14 of the LRP6 gene (SEQ ID NO:3)

GFTVVSSVPSQNLEIQPYDLSIDIYSRYIYWTCEATNVINVTRLDGRSVGVVLKGEQDRPRAIVVNPEKG

Amino acid sequence of exon 14 of LRP6 gene (SEQ ID NO:4)

GGCTTTACTGTGGTTGTGAGCTCAGTTCCGAGTCAGAACCTGGAAATACAACCCTATGACCTCAGCATTGATATTTACAGCCGCTACATCTACTGGACTTGTGAGC
CTACCAATGTCATTAATGTGACAAGATTAGATGGGAGATCAGTTGGAGTGGTGCTGAAGGGCGAGCAGGACAGACCTCGAGCCGTTGTGTGGTAAACCCAGAGAAAG(

Sequence of exon 14 of the LRP6 gene (including SNP rs2302685) (SEQ ID NO:5)

GFTVVSSVPSQNLEIQPYDLSIDIYSRYIYWTCEATNVINVTRLDGRSVGVVLKGEQDRPRAVVVNPEKG

Amino acid sequence of exon 14 of LRP6 (including SNP rs2302685) (SEQ ID NO:6)

Figure 7

AACCTCCAACATGTTCTCCTCAGCAGTTTACTTGTTTCACGGGGGAAATTGACTGTATCCCTGTGGCTTGGCGGTGCGATGGGTTTACTGAATGTGAAGACCACAGTG
ATGAACTCAATTGTCCTGTATGCTCAGAGTCTCAGAGTTCCCAGTGCCAGTGTGGGCAGTGTATTGATGGTGCCCTCCGATGCAATGGAGATGCAAACTGCCAGGACAAAT
CAGAGATGAGAAGAACTGTGAAG

Sequence of exon 18 of the LRP6 gene (SEQ ID NO:7)

EPPTCSPQQFTCFTGEIDCIPVAWRCDGFTECEDHSDELNCPVCSESQFQCASGQCIDGALRCNGDANCQDKSDEKNCEV

Amino acid sequence of exon 18 of LRP6 (SEQ ID NO:8)

AACCTCCAACATGTTCTCCTCAGCAGTTTACTTGTTTCACGGGGGAAATTGACTGTATCCCTGTGGCTTGGCGGTGCTGATGGGTTTACTGAATGTGAAGACCACAGTG
ATGAACTCAATTGTCCTGTATGCTCAGAGTCTCAGAGTTCCCAGTGCCAGTGTGGGCAGTGTATTGATGGTGCCCTCCGATGCAATGGAGATGCAAACTGCCAGGACAAAT
CAGAGATGAGAAGAACTGTGAAG

Sequence of exon 18 of the LRP6 gene (including SNP rs1012672 which does not change amino acid) (SEQ ID NO:9)

Figure 8

SEQUENCE LISTING

```
<160> NUMBER OF SEQ ID NOS: 35

<210> SEQ ID NO 1
<211> LENGTH: 4842
<212> TYPE: DNA
<213> ORGANISM: LRP6 gene

<400> SEQUENCE: 1
atgggggccg tcctgaggag cctcctggcc tgcagcttct gtgtgctcct gagagcggcc      60
cctttgttgc tttatgcaaa cagacgggac ttgcgattgg ttgatgctac aaatggcaaa     120
gagaatgcta cgattgtagt tggaggcttg gaggatgcag ctgcggtgga ctttgtgttt     180
agtcatggct tgatatactg gagtgatgtc agcgaagaag ccattaaacg aacagaattt     240
aacaaaactg agagtgtgca gaatgttgtt gtttctggat tattgtcccc cgatgggctg     300
gcatgtgatt ggcttggaga aaaattgtac tggacagatt ctgaaactaa tcggattgaa     360
gtttctaatt tagatggatc tttacgaaaa gttttatttt ggcaagagtt ggatcaaccc     420
agagctattg ccttagatcc ttcaagtggg ttcatgtact ggacagactg gggagaagtg     480
ccaaagatag aacgtgctgg aatggatggt tcaagtcgct tcattataat aaacagtgaa     540
atttactggc aaatggact gactttggat tatgaagaac aaaagcttta ttgggcagat     600
gcaaaactta atttcatcca caatcaaat ctggatggaa caaatcggca ggcagtggtt     660
aaaggttccc ttccacatcc ttttgccttg acgttatttg aggacatatt gtactggact     720
gactggagca cacactccat tttggcttgc aacaagtata ctggtgaggg tctgcgtgaa     780
atccattctg acatcttctc tcccatggat atacatgcct tcagccaaca gaggcagcca     840
aatgccacaa atccatgtgg aattgacaat ggggggttgtt cccatttgtg tttgatgtct     900
ccagtcaagc cttttatca gtgtgcttgc cccactgggg tcaaactcct ggagaatgga     960
aaaacctgca aagatggtgc cacagaatta ttgcttttag ctcgaaggac agacttgaga    1020
cgcatttctt tggatacacc agattttaca gacattgttc tgcagttaga agacatccgt    1080
catgccattg ccatagatta cgatcctgtg gaaggctaca tctactggac tgatgatgaa    1140
gtgagggcca tacgccgttc atttatagat ggatctggca gtcagtttgt ggtcactgct    1200
caaattgccc atcctgatgg tattgctgtg gactgggttg cacgaaatct ttattggaca    1260
gacactggca ctgatcgaat agaagtgaca aggctcaatg ggaccatgag gaagatcttg    1320
atttcagagg acttagagga accccgggct attgtgttag atcccatggt tgggtacatg    1380
tattggactg actggggaga aattccgaaa attgagcgag cagctctgga tggttctgac    1440
cgtgtagtat tggttaacac ttctcttggt tggccaaatg gtttagcctt ggattatgat    1500
```

-continued

```
gaaggcaaaa tatactgggg agatgccaaa acagacaaga ttgaggttat gaatactgat    1560
ggcactggga gacgagtact agtggaagac aaaattcctc acatatttgg atttactttg    1620
ttgggtgact atgtttactg gactgactgg cagaggcgta gcattgaaag agttcataaa    1680
cgaagtgcag agagggaagt gatcatagat cagctgcctg acctcatggg cctaaaggct    1740
acaaatgttc atcgagtgat tggttccaac ccctgtgctg aggaaaacgg gggatgtagc    1800
catctctgcc tctatagacc tcagggcctt cgctgtgctt gccctattgg ctttgaactc    1860
atcagtgaca tgaagacctg cattgtccca gaggctttcc ttttgttttc acggagagca    1920
gatatcagac gaatttctct ggaaacaaac aataataatg tggctattcc actcactggt    1980
gtcaaagaag cttctgcttt ggattttgat gtgacagaca accgaattta ttggactgat    2040
atatcactca agaccatcag cagagccttt atgaatggca gtgcactgga acatgtggta    2100
gaattcggct tagattatcc agaaggcatg gcagtagact ggcttgggaa gaacttgtac    2160
tgggcagaca caggaacgaa tcgaattgag gtgtcaaagt tggatgggca gcaccgacaa    2220
gttttggtgt ggaaagacct agatagtccc agagctctcg cgttggaccc tgccgaagga    2280
tttatgtatt ggactgaatg gggtggaaaa cctaagatag acagagctgc aatggatgga    2340
agtgaacgta ctaccttagt tccaaatgtg gggcgggcaa acggcctaac tattgattat    2400
gctaaaagga ggctttattg gacagacctg gacaccaact aatagaaatc ttcaaatatg    2460
cttgggctca accgtgaagt tatagcagat gacttgcctc atccttttgg cttaactcag    2520
taccaagatt atatctactg gacggactgg agccgacgca gcattgagcg tgccaacaaa    2580
accagtggcc aaaaccgcac catcattcag ggccatttgg attatgtgat ggacatcctc    2640
gtctttcact catctcgaca gtcagggtgg aatgaatgtg cttccagcaa tgggcactgc    2700
tcccacctct gcttggctgt gccagttggg ggttttgttt gtggatgccc tgcccactac    2760
tctcttaatg ctgacaacag gacttgtagt gctcctacga ctttcctgct cttcagtcaa    2820
aagagtgcca tcaaccgcat ggtgattgat gaacaacaga gccccgacat catccttccc    2880
atccacagcc ttcggaatgt ccgggccatt gactatgacc cactggacaa gcaactctat    2940
tggattgact cacgacaaaa catgatccga aaggcacaag aagatggcag ccagggcttt    3000
actgtggttg tgagctcagt tccgagtcag aacctggaaa tacaacccta tgacctcagc    3060
attgatattt acagccgcta catctactgg acttgtgagg ctaccaatgt cattaatgtg    3120
acaagattag atgggagatc agttggagtg gtgctgaaag cgagcagga cagacctcga    3180 gccattgtgg taaacccaga gaaagggtat atgtattta ccaatcttca ggaaaggtct    3240
cctaaaattg aacgggctgc tttggatggg acagaacggg aggtcctctt tttcagtggc    3300
ttaagtaaac caattgcttt agcccttgat agcaggctgg gcaagctctt tgggctgat    3360 tcagatctcc ggcgaattga aagcagtgat ctctcaggtg ctaaccggat agtattagaa    3420
gactccaata tcttgcagcc tgtgggactt actgtgtttg aaaactggct ctattggatt    3480
gataaacagc agcaaatgat tgaaaaaatt gacatgacag tcgagaggg tagaaccaaa    3540 gtccaagctc gaattgccca gcttagtgac attcatgcag taaggagct gaaccttcaa    3600 gaatacagac agcacccttg tgctcaggat aatggtggct gttcacatat ttgtcttgta    3660
aagggggatg gtactacaag gtgttcttgc cccatgcacc tggttctact tcaagatgag    3720
ctatcatgtg gagaacctcc aacatgttct cctcagcagt ttacttgttt cacggggaa    3780 attgactgta tccctgtggc ttggcggtgc gatgggttta ctgaatgtga agaccacagt    3840
```

```
gatgaactca attgtcctgt atgctcagag tcccagttcc agtgtgccag tgggcagtgt    3900
attgatggtg ccctccgatg caatggagat gcaaactgcc aggacaaatc agatgagaag    3960
aactgtgaag tgctttgttt aattgatcag ttccgctgtg ccaatggtca gtgcattgga    4020
aagcacaaga gtgtgatca taatgtggat tgcagtgaca gtcagatga actggattgt      4080 tatccgactg aagaaccagc accacaggcc accaatacag ttggttctgt tattggcgta    4140
attgtcacca ttttgtgtc tggaactgta tactttatct gccagaggat gttgtgtcca     4200
cgtatgaagg gagatgggga aactatgact aatgactatg tagttcatgg accagcttct    4260
gtgcctcttg gttatgtgcc acacccaagt tctttgtcag atctcttcc aggaatgtct     4320 cgaggtaaat caatgatcag ctccctcagt atcatggggg gaagcagtgg acccccctat    4380
gaccgagccc atgttacagg agcatcatca agtagttctt caagcaccaa aggcacttac    4440
ttccctgcaa ttttgaaccc tccaccatcc ccagccacag agcgatcaca ttacactatg    4500
gaatttggat attcttcaaa cagtccttcc actcataggt catacagcta caggccatat    4560
agctaccggc actttgcacc ccccaccaca ccctgcagca cagatgtttg tgacagtgac    4620
tatgctccta gtcggagaat gacctcagtg gcaacagcca aggctatac cagtgacttg      4680 aactatgatt cagaacctgt gccccacct cccacacccc gaagccaata cttgtcagca     4740
gaggagaact atgaaagctg cccaccttct ccatacacag agaggagcta ttctcatcac    4800
ctctacccac cgccaccctc tccctgtaca gactcctcct ga                        4842

<210> SEQ ID NO 2
<211> LENGTH: 1613
<212> TYPE: PRT
<213> ORGANISM: LRP6 protein

<400> SEQUENCE: 2

Met Gly Ala Val Leu Arg Ser Leu Leu Ala Cys Ser Phe Cys Val Leu
1               5                   10                  15

Leu Arg Ala Ala Pro Leu Leu Leu Tyr Ala Asn Arg Arg Asp Leu Arg
                20                  25                  30

Leu Val Asp Ala Thr Asn Gly Lys Glu Asn Ala Thr Ile Val Val Gly
            35                  40                  45

Gly Leu Glu Asp Ala Ala Ala Val Asp Phe Val Phe Ser His Gly Leu
        50                  55                  60

Ile Tyr Trp Ser Asp Val Ser Glu Glu Ala Ile Lys Arg Thr Glu Phe
65                  70                  75                  80

Asn Lys Thr Glu Ser Val Gln Asn Val Val Val Ser Gly Leu Leu Ser
                85                  90                  95

Pro Asp Gly Leu Ala Cys Asp Trp Leu Gly Glu Lys Leu Tyr Trp Thr
            100                 105                 110

Asp Ser Glu Thr Asn Arg Ile Glu Val Ser Asn Leu Asp Gly Ser Leu
        115                 120                 125

Arg Lys Val Leu Phe Trp Gln Glu Leu Asp Gln Pro Arg Ala Ile Ala
    130                 135                 140

Leu Asp Pro Ser Ser Gly Phe Met Tyr Trp Thr Asp Trp Gly Glu Val
145                 150                 155                 160

Pro Lys Ile Glu Arg Ala Gly Met Asp Gly Ser Ser Arg Phe Ile Ile
                165                 170                 175

Ile Asn Ser Glu Ile Tyr Trp Pro Asn Gly Leu Thr Leu Asp Tyr Glu
            180                 185                 190

Glu Gln Lys Leu Tyr Trp Ala Asp Ala Lys Leu Asn Phe Ile His Lys
```

-continued

```
            195                 200                 205
Ser Asn Leu Asp Gly Thr Asn Arg Gln Ala Val Lys Gly Ser Leu
    210                 215                 220

Pro His Pro Phe Ala Leu Thr Leu Phe Glu Asp Ile Leu Tyr Trp Thr
225                 230                 235                 240

Asp Trp Ser Thr His Ser Ile Leu Ala Cys Asn Lys Tyr Thr Gly Glu
                245                 250                 255

Gly Leu Arg Glu Ile His Ser Asp Ile Phe Ser Pro Met Asp Ile His
            260                 265                 270

Ala Phe Ser Gln Gln Arg Gln Pro Asn Ala Thr Asn Pro Cys Gly Ile
        275                 280                 285

Asp Asn Gly Gly Cys Ser His Leu Cys Leu Met Ser Pro Val Lys Pro
    290                 295                 300

Phe Tyr Gln Cys Ala Cys Pro Thr Gly Val Lys Leu Leu Glu Asn Gly
305                 310                 315                 320

Lys Thr Cys Lys Asp Gly Ala Thr Glu Leu Leu Leu Ala Arg Arg
                325                 330                 335

Thr Asp Leu Arg Arg Ile Ser Leu Asp Thr Pro Asp Phe Thr Asp Ile
            340                 345                 350

Val Leu Gln Leu Glu Asp Ile Arg His Ala Ile Ala Ile Asp Tyr Asp
        355                 360                 365

Pro Val Glu Gly Tyr Ile Tyr Trp Thr Asp Asp Glu Val Arg Ala Ile
    370                 375                 380

Arg Arg Ser Phe Ile Asp Gly Ser Gly Ser Gln Phe Val Val Thr Ala
385                 390                 395                 400

Gln Ile Ala His Pro Asp Gly Ile Ala Val Asp Trp Val Ala Arg Asn
                405                 410                 415

Leu Tyr Trp Thr Asp Thr Gly Thr Asp Arg Ile Glu Val Thr Arg Leu
            420                 425                 430

Asn Gly Thr Met Arg Lys Ile Leu Ile Ser Glu Asp Leu Glu Glu Pro
        435                 440                 445

Arg Ala Ile Val Leu Asp Pro Met Val Gly Tyr Met Tyr Trp Thr Asp
    450                 455                 460

Trp Gly Glu Ile Pro Lys Ile Glu Arg Ala Ala Leu Asp Gly Ser Asp
465                 470                 475                 480

Arg Val Val Leu Val Asn Thr Ser Leu Gly Trp Pro Asn Gly Leu Ala
                485                 490                 495

Leu Asp Tyr Asp Glu Gly Lys Ile Tyr Trp Gly Asp Ala Lys Thr Asp
            500                 505                 510

Lys Ile Glu Val Met Asn Thr Asp Gly Thr Gly Arg Arg Val Leu Val
        515                 520                 525

Glu Asp Lys Ile Pro His Ile Phe Gly Phe Thr Leu Leu Gly Asp Tyr
    530                 535                 540

Val Tyr Trp Thr Asp Trp Gln Arg Ser Ile Glu Arg Val His Lys
545                 550                 555                 560

Arg Ser Ala Glu Arg Glu Val Ile Ile Asp Gln Leu Pro Asp Leu Met
                565                 570                 575

Gly Leu Lys Ala Thr Asn Val His Arg Val Ile Gly Ser Asn Pro Cys
            580                 585                 590

Ala Glu Glu Asn Gly Gly Cys Ser His Leu Cys Leu Tyr Arg Pro Gln
        595                 600                 605

Gly Leu Arg Cys Ala Cys Pro Ile Gly Phe Glu Leu Ile Ser Asp Met
    610                 615                 620
```

-continued

```
Lys Thr Cys Ile Val Pro Glu Ala Phe Leu Leu Phe Ser Arg Arg Ala
625                 630                 635                 640

Asp Ile Arg Arg Ile Ser Leu Glu Thr Asn Asn Asn Val Ala Ile
            645                 650                 655

Pro Leu Thr Gly Val Lys Glu Ala Ser Ala Leu Asp Phe Asp Val Thr
            660                 665                 670

Asp Asn Arg Ile Tyr Trp Thr Asp Ile Ser Leu Lys Thr Ile Ser Arg
            675                 680                 685

Ala Phe Met Asn Gly Ser Ala Leu Glu His Val Glu Phe Gly Leu
690                 695                 700

Asp Tyr Pro Glu Gly Met Ala Val Asp Trp Leu Gly Lys Asn Leu Tyr
705                 710                 715                 720

Trp Ala Asp Thr Gly Thr Asn Arg Ile Glu Val Ser Lys Leu Asp Gly
                725                 730                 735

Gln His Arg Gln Val Leu Val Trp Lys Asp Leu Asp Ser Pro Arg Ala
            740                 745                 750

Leu Ala Leu Asp Pro Ala Glu Gly Phe Met Tyr Trp Thr Glu Trp Gly
            755                 760                 765

Gly Lys Pro Lys Ile Asp Arg Ala Ala Met Asp Gly Ser Glu Arg Thr
770                 775                 780

Thr Leu Val Pro Asn Val Gly Arg Ala Asn Gly Leu Thr Ile Asp Tyr
785                 790                 795                 800

Ala Lys Arg Arg Leu Tyr Trp Thr Asp Leu Asp Thr Asn Leu Ile Glu
                805                 810                 815

Ser Ser Asn Met Leu Gly Leu Asn Arg Glu Val Ile Ala Asp Asp Leu
            820                 825                 830

Pro His Pro Phe Gly Leu Thr Gln Tyr Gln Asp Tyr Ile Tyr Trp Thr
            835                 840                 845

Asp Trp Ser Arg Arg Ser Ile Glu Arg Ala Asn Lys Thr Ser Gly Gln
850                 855                 860

Asn Arg Thr Ile Ile Gln Gly His Leu Asp Tyr Val Met Asp Ile Leu
865                 870                 875                 880

Val Phe His Ser Ser Arg Gln Ser Gly Trp Asn Glu Cys Ala Ser Ser
                885                 890                 895

Asn Gly His Cys Ser His Leu Cys Leu Ala Val Pro Val Gly Gly Phe
            900                 905                 910

Val Cys Gly Cys Pro Ala His Tyr Ser Leu Asn Ala Asp Asn Arg Thr
            915                 920                 925

Cys Ser Ala Pro Thr Thr Phe Leu Leu Phe Ser Gln Lys Ser Ala Ile
930                 935                 940

Asn Arg Met Val Ile Asp Glu Gln Gln Ser Pro Asp Ile Ile Leu Pro
945                 950                 955                 960

Ile His Ser Leu Arg Asn Val Arg Ala Ile Asp Tyr Asp Pro Leu Asp
                965                 970                 975

Lys Gln Leu Tyr Trp Ile Asp Ser Arg Gln Asn Met Ile Arg Lys Ala
            980                 985                 990

Gln Glu Asp Gly Ser Gln Gly Phe Thr Val Val Val Ser Ser Val Pro
            995                 1000                1005

Ser Gln Asn Leu Glu Ile Gln Pro Tyr Asp Leu Ser Ile Asp Ile
    1010                1015                1020

Tyr Ser Arg Tyr Ile Tyr Trp Thr Cys Glu Ala Thr Asn Val Ile
    1025                1030                1035
```

-continued

Asn Val Thr Arg Leu Asp Gly Arg Ser Val Gly Val Val Leu Lys
1040                1045                1050

Gly Glu Gln Asp Arg Pro Arg Ala Ile Val Val Asn Pro Glu Lys
1055                1060                1065

Gly Tyr Met Tyr Phe Thr Asn Leu Gln Glu Arg Ser Pro Lys Ile
1070                1075                1080

Glu Arg Ala Ala Leu Asp Gly Thr Glu Arg Glu Val Leu Phe Phe
1085                1090                1095

Ser Gly Leu Ser Lys Pro Ile Ala Leu Ala Leu Asp Ser Arg Leu
1100                1105                1110

Gly Lys Leu Phe Trp Ala Asp Ser Asp Leu Arg Arg Ile Glu Ser
1115                1120                1125

Ser Asp Leu Ser Gly Ala Asn Arg Ile Val Leu Glu Asp Ser Asn
1130                1135                1140

Ile Leu Gln Pro Val Gly Leu Thr Val Phe Glu Asn Trp Leu Tyr
1145                1150                1155

Trp Ile Asp Lys Gln Gln Gln Met Ile Glu Lys Ile Asp Met Thr
1160                1165                1170

Gly Arg Glu Gly Arg Thr Lys Val Gln Ala Arg Ile Ala Gln Leu
1175                1180                1185

Ser Asp Ile His Ala Val Lys Glu Leu Asn Leu Gln Glu Tyr Arg
1190                1195                1200

Gln His Pro Cys Ala Gln Asp Asn Gly Gly Cys Ser His Ile Cys
1205                1210                1215

Leu Val Lys Gly Asp Gly Thr Thr Arg Cys Ser Cys Pro Met His
1220                1225                1230

Leu Val Leu Leu Gln Asp Glu Leu Ser Cys Gly Glu Pro Pro Thr
1235                1240                1245

Cys Ser Pro Gln Gln Phe Thr Cys Phe Thr Gly Glu Ile Asp Cys
1250                1255                1260

Ile Pro Val Ala Trp Arg Cys Asp Gly Phe Thr Glu Cys Glu Asp
1265                1270                1275

His Ser Asp Glu Leu Asn Cys Pro Val Cys Ser Glu Ser Gln Phe
1280                1285                1290

Gln Cys Ala Ser Gly Gln Cys Ile Asp Gly Ala Leu Arg Cys Asn
1295                1300                1305

Gly Asp Ala Asn Cys Gln Asp Lys Ser Asp Glu Lys Asn Cys Glu
1310                1315                1320

Val Leu Cys Leu Ile Asp Gln Phe Arg Cys Ala Asn Gly Gln Cys
1325                1330                1335

Ile Gly Lys His Lys Lys Cys Asp His Asn Val Asp Cys Ser Asp
1340                1345                1350

Lys Ser Asp Glu Leu Asp Cys Tyr Pro Thr Glu Glu Pro Ala Pro
1355                1360                1365

Gln Ala Thr Asn Thr Val Gly Ser Val Ile Gly Val Ile Val Thr
1370                1375                1380

Ile Phe Val Ser Gly Thr Val Tyr Phe Ile Cys Gln Arg Met Leu
1385                1390                1395

Cys Pro Arg Met Lys Gly Asp Gly Glu Thr Met Thr Asn Asp Tyr
1400                1405                1410

Val Val His Gly Pro Ala Ser Val Pro Leu Gly Tyr Val Pro His
1415                1420                1425

Pro Ser Ser Leu Ser Gly Ser Leu Pro Gly Met Ser Arg Gly Lys

-continued

```
                  1430                1435                1440
Ser Met Ile Ser Ser Leu Ser Ile Met Gly Gly Ser Ser Gly Pro
    1445                1450                1455

Pro Tyr Asp Arg Ala His Val Thr Gly Ala Ser Ser Ser Ser Ser
    1460                1465                1470

Ser Ser Thr Lys Gly Thr Tyr Phe Pro Ala Ile Leu Asn Pro Pro
    1475                1480                1485

Pro Ser Pro Ala Thr Glu Arg Ser His Tyr Thr Met Glu Phe Gly
    1490                1495                1500

Tyr Ser Ser Asn Ser Pro Ser Thr His Arg Ser Tyr Ser Tyr Arg
    1505                1510                1515

Pro Tyr Ser Tyr Arg His Phe Ala Pro Pro Thr Thr Pro Cys Ser
    1520                1525                1530

Thr Asp Val Cys Asp Ser Asp Tyr Ala Pro Ser Arg Arg Met Thr
    1535                1540                1545

Ser Val Ala Thr Ala Lys Gly Tyr Thr Ser Asp Leu Asn Tyr Asp
    1550                1555                1560

Ser Glu Pro Val Pro Pro Pro Thr Pro Arg Ser Gln Tyr Leu
    1565                1570                1575

Ser Ala Glu Glu Asn Tyr Glu Ser Cys Pro Pro Ser Pro Tyr Thr
    1580                1585                1590

Glu Arg Ser Tyr Ser His His Leu Tyr Pro Pro Pro Ser Pro
    1595                1600                1605

Cys Thr Asp Ser Ser
    1610

<210> SEQ ID NO 3
<211> LENGTH: 212
<212> TYPE: DNA
<213> ORGANISM: LRP6 gene

<400> SEQUENCE: 3
ggctttactg tggttgtgag ctcagttccg agtcagaacc tggaaataca accctatgac      60
ctcagcattg atatttacag ccgctacatc tactggactt gtgaggctac caatgtcatt     120
aatgtgacaa gattagatgg gagatcagtt ggagtggtgc tgaaaggcga gcaggacaga     180
cctcgagcca ttgtggtaaa cccagagaaa gg                                   212

<210> SEQ ID NO 4
<211> LENGTH: 71
<212> TYPE: PRT
<213> ORGANISM: LRP6 gene

<400> SEQUENCE: 4

Gly Phe Thr Val Val Ser Ser Val Pro Ser Gln Asn Leu Glu Ile
1               5                   10                  15

Gln Pro Tyr Asp Leu Ser Ile Asp Ile Tyr Ser Arg Tyr Ile Tyr Trp
            20                  25                  30

Thr Cys Glu Ala Thr Asn Val Ile Asn Val Thr Arg Leu Asp Gly Arg
        35                  40                  45

Ser Val Gly Val Val Leu Lys Gly Glu Gln Asp Arg Pro Arg Ala Ile
    50                  55                  60

Val Val Asn Pro Glu Lys Gly
65                  70

<210> SEQ ID NO 5
```

```
<211> LENGTH: 212
<212> TYPE: DNA
<213> ORGANISM: LRP6 gene

<400> SEQUENCE: 5
ggctttactg tggttgtgag ctcagttccg agtcagaacc tggaaataca accctatgac        60
ctcagcattg atatttacag ccgctacatc tactggactt gtgaggctac caatgtcatt       120
aatgtgacaa gattagatgg gagatcagtt ggagtggtgc tgaaaggcga gcaggacaga       180
cctcgagccg ttgtggtaaa cccagagaaa gg                                     212

<210> SEQ ID NO 6
<211> LENGTH: 71
<212> TYPE: PRT
<213> ORGANISM: LRP6

<400> SEQUENCE: 6

Gly Phe Thr Val Val Ser Ser Val Pro Ser Gln Asn Leu Glu Ile
1               5                   10                  15

Gln Pro Tyr Asp Leu Ser Ile Asp Ile Tyr Ser Arg Tyr Ile Tyr Trp
            20                  25                  30

Thr Cys Glu Ala Thr Asn Val Ile Asn Val Thr Arg Leu Asp Gly Arg
        35                  40                  45

Ser Val Gly Val Val Leu Lys Gly Glu Gln Asp Arg Pro Arg Ala Val
    50                  55                  60

Val Val Asn Pro Glu Lys Gly
65                  70

<210> SEQ ID NO 7
<211> LENGTH: 237
<212> TYPE: DNA
<213> ORGANISM: LRP6 gene

<400> SEQUENCE: 7
aacctccaac atgttctcct cagcagttta cttgtttcac gggggaaatt gactgtatcc        60
ctgtggcttg gcggtgcgat gggtttactg aatgtgaaga ccacagtgat gaactcaatt       120
gtcctgtatg ctcagagtcc cagttccagt gtgccagtgg cagtgtatt  gatggtgccc       180 tccgatgcaa tggagatgca aactgccagg acaaatcaga tgagaagaac tgtgaag          237

<210> SEQ ID NO 8
<211> LENGTH: 80
<212> TYPE: PRT
<213> ORGANISM: LRP6

<400> SEQUENCE: 8

Glu Pro Pro Thr Cys Ser Pro Gln Gln Phe Thr Cys Phe Thr Gly Glu
1               5                   10                  15

Ile Asp Cys Ile Pro Val Ala Trp Arg Cys Asp Gly Phe Thr Glu Cys
            20                  25                  30

Glu Asp His Ser Asp Glu Leu Asn Cys Pro Val Cys Ser Glu Ser Gln
        35                  40                  45

Phe Gln Cys Ala Ser Gly Gln Cys Ile Asp Gly Ala Leu Arg Cys Asn
    50                  55                  60

Gly Asp Ala Asn Cys Gln Asp Lys Ser Asp Glu Lys Asn Cys Glu Val
65                  70                  75                  80

<210> SEQ ID NO 9
<211> LENGTH: 237
```

```
<212> TYPE: DNA
<213> ORGANISM: LRP6 gene

<400> SEQUENCE: 9
aacctccaac atgttctcct cagcagttta cttgtttcac gggggaaatt gactgtatcc    60
ctgtggcttg gcggtgtgat gggtttactg aatgtgaaga ccacagtgat gaactcaatt   120
gtcctgtatg ctcagagtcc cagttccagt gtgccagtgg cagtgtatt  atggtgccc    180
tccgatgcaa tggagatgca aactgccagg acaaatcaga tgagaagaac tgtgaag      237

<210> SEQ ID NO 10
<211> LENGTH: 55
<212> TYPE: PRT
<213> ORGANISM: Human LRP6

<400> SEQUENCE: 10

Tyr Ser Arg Tyr Ile Tyr Trp Thr Cys Glu Ala Thr Asn Val Ile Asn
1               5                   10                  15

Val Thr Arg Leu Asp Gly Arg Ser Val Gly Val Val Leu Lys Gly Glu
            20                  25                  30

Gln Asp Arg Pro Arg Ala Ile Val Val Asn Pro Glu Lys Gly Tyr Met
        35                  40                  45

Tyr Phe Thr Asn Leu Gln Glu
    50                  55

<210> SEQ ID NO 11
<211> LENGTH: 55
<212> TYPE: PRT
<213> ORGANISM: Mouse LRP6

<400> SEQUENCE: 11

Tyr Ser Arg Tyr Ile Tyr Trp Thr Cys Glu Ala Thr Asn Val Ile Asp
1               5                   10                  15

Val Thr Arg Leu Asp Gly Arg Ser Val Gly Val Val Leu Lys Gly Glu
            20                  25                  30

Gln Asp Arg Pro Arg Ala Ile Val Val Asn Pro Glu Lys Gly Tyr Met
        35                  40                  45

Tyr Phe Thr Asn Leu Gln Glu
    50                  55

<210> SEQ ID NO 12
<211> LENGTH: 55
<212> TYPE: PRT
<213> ORGANISM: Human LRP5

<400> SEQUENCE: 12

Tyr Ser Arg Thr Leu Phe Trp Thr Cys Glu Ala Thr Asn Thr Ile Asn
1               5                   10                  15

Val His Arg Leu Ser Gly Glu Ala Met Gly Val Val Leu Arg Gly Asp
            20                  25                  30

Arg Asp Lys Pro Arg Ala Ile Val Val Asn Ala Glu Arg Gly Tyr Leu
        35                  40                  45

Tyr Phe Thr Asn Met Gln Asp
    50                  55

<210> SEQ ID NO 13
<211> LENGTH: 55
<212> TYPE: PRT
<213> ORGANISM: Mouse LRP5
```

-continued

```
<400> SEQUENCE: 13

Tyr Ser Arg Thr Leu Phe Trp Thr Cys Glu Ala Thr Asn Thr Ile Asn
1               5                   10                  15

Val His Arg Leu Asp Gly Asp Ala Met Gly Val Val Leu Arg Gly Asp
            20                  25                  30

Arg Asp Lys Pro Arg Ala Ile Ala Val Asn Ala Glu Arg Gly Tyr Met
        35                  40                  45

Tyr Phe Thr Asn Met Gln Asp
    50                  55

<210> SEQ ID NO 14
<211> LENGTH: 55
<212> TYPE: PRT
<213> ORGANISM: Drosophila melanogaster Arrow

<400> SEQUENCE: 14

Ile Gly Arg Leu Leu Phe Trp Thr Cys Ser Gln Ser Asn Ser Ile Asn
1               5                   10                  15

Val Thr Ser Phe Leu Gly Glu Ser Val Gly Val Ile Asp Thr Gly Asp
            20                  25                  30

Ser Glu Lys Pro Arg Asn Ile Ala Val His Ala Met Lys Arg Leu Leu
        35                  40                  45

Phe Trp Thr Asp Val Gly Ser
    50                  55

<210> SEQ ID NO 15
<211> LENGTH: 55
<212> TYPE: PRT
<213> ORGANISM: Human LDLR

<400> SEQUENCE: 15

Ile His Ser Asn Ile Tyr Trp Thr Asp Ser Val Leu Gly Thr Val Ser
1               5                   10                  15

Val Ala Asp Thr Lys Gly Val Lys Arg Lys Thr Leu Phe Arg Glu Asn
            20                  25                  30

Gly Ser Lys Pro Arg Ala Ile Val Val Asp Pro Val His Gly Phe Met
        35                  40                  45

Tyr Trp Thr Asp Trp Gly Arg
    50                  55

<210> SEQ ID NO 16
<211> LENGTH: 55
<212> TYPE: PRT
<213> ORGANISM: Mouse LDLR

<400> SEQUENCE: 16

Ile His Arg Asn Ile Tyr Trp Thr Asp Ser Val Pro Gly Ser Val Ser
1               5                   10                  15

Val Ala Asp Thr Lys Gly Val Lys Arg Arg Thr Leu Phe Gln Glu Ala
            20                  25                  30

Gly Ser Arg Pro Arg Ala Ile Val Val Asp Pro Val His Gly Phe Met
        35                  40                  45

Tyr Trp Thr Asp Trp Gly Thr
    50                  55

<210> SEQ ID NO 17
<211> LENGTH: 4
<212> TYPE: PRT
<213> ORGANISM: Artificial
```

```
<220> FEATURE:
<223> OTHER INFORMATION: Synthetic Construct

<400> SEQUENCE: 17

Tyr Trp Thr Asp
1

<210> SEQ ID NO 18
<211> LENGTH: 25
<212> TYPE: DNA
<213> ORGANISM: Artificial
<220> FEATURE:
<223> OTHER INFORMATION: Forward Primer

<400> SEQUENCE: 18
agggatggat ctcacctta gaata                                          25

<210> SEQ ID NO 19
<211> LENGTH: 25
<212> TYPE: DNA
<213> ORGANISM: Artificial
<220> FEATURE:
<223> OTHER INFORMATION: Forward Primer

<400> SEQUENCE: 19
catgaatatg actctttccc ccaga                                         25

<210> SEQ ID NO 20
<211> LENGTH: 25
<212> TYPE: DNA
<213> ORGANISM: Artificial
<220> FEATURE:
<223> OTHER INFORMATION: Forward Primer

<400> SEQUENCE: 20
attgtgactg attgcctcag ggtta                                         25

<210> SEQ ID NO 21
<211> LENGTH: 25
<212> TYPE: DNA
<213> ORGANISM: Artificial
<220> FEATURE:
<223> OTHER INFORMATION: Forward Primer

<400> SEQUENCE: 21
tgacccacat gagtcatttc tgttg                                         25

<210> SEQ ID NO 22
<211> LENGTH: 25
<212> TYPE: DNA
<213> ORGANISM: Artificial
<220> FEATURE:
<223> OTHER INFORMATION: Forward Primer

<400> SEQUENCE: 22
gtcactcccc ttctccttgt tcatt                                         25

<210> SEQ ID NO 23
<211> LENGTH: 27
<212> TYPE: DNA
<213> ORGANISM: Artificial
<220> FEATURE:
<223> OTHER INFORMATION: Reverse Primer

<400> SEQUENCE: 23
cattatactg tcgactcaaa acccatt                                       27
```

```
<210> SEQ ID NO 24
<211> LENGTH: 25
<212> TYPE: DNA
<213> ORGANISM: Artificial
<220> FEATURE:
<223> OTHER INFORMATION: Reverse Primer

<400> SEQUENCE: 24
accaatgata aatagcagcc actga                                              25

<210> SEQ ID NO 25
<211> LENGTH: 25
<212> TYPE: DNA
<213> ORGANISM: Artificial
<220> FEATURE:
<223> OTHER INFORMATION: Reverse Primer

<400> SEQUENCE: 25
taacaggctg aaaagaagg gtgag                                               25

<210> SEQ ID NO 26
<211> LENGTH: 25
<212> TYPE: DNA
<213> ORGANISM: Artificial
<220> FEATURE:
<223> OTHER INFORMATION: Reverse Primer

<400> SEQUENCE: 26
ttcctccaat tagctttatc ccatt                                              25

<210> SEQ ID NO 27
<211> LENGTH: 25
<212> TYPE: DNA
<213> ORGANISM: Artificial
<220> FEATURE:
<223> OTHER INFORMATION: Reverse Primer

<400> SEQUENCE: 27
ggcactgaag aattctggat acctt                                              25

<210> SEQ ID NO 28
<211> LENGTH: 15
<212> TYPE: DNA
<213> ORGANISM: Artificial
<220> FEATURE:
<223> OTHER INFORMATION: PCR Primer

<400> SEQUENCE: 28
gacagacctc gagcc                                                         15

<210> SEQ ID NO 29
<211> LENGTH: 13
<212> TYPE: DNA
<213> ORGANISM: Artificial
<220> FEATURE:
<223> OTHER INFORMATION: PCR Primer

<400> SEQUENCE: 29
tggcttggcg gtg                                                           13

<210> SEQ ID NO 30
<211> LENGTH: 20
<212> TYPE: DNA
<213> ORGANISM: Artificial
<220> FEATURE:
```

```
<223> OTHER INFORMATION: LRP5 Forward Primer

<400> SEQUENCE: 30
actcagagac caaccgcatc                                               20

<210> SEQ ID NO 31
<211> LENGTH: 20
<212> TYPE: DNA
<213> ORGANISM: Artificial
<220> FEATURE:
<223> OTHER INFORMATION: LRP5 Reverse Primer

<400> SEQUENCE: 31
tccattgggc cagtaaatgt                                               20

<210> SEQ ID NO 32
<211> LENGTH: 20
<212> TYPE: DNA
<213> ORGANISM: Artificial
<220> FEATURE:
<223> OTHER INFORMATION: LRP6 Forward Primer

<400> SEQUENCE: 32
catgtgattg gcttggagaa                                               20

<210> SEQ ID NO 33
<211> LENGTH: 20
<212> TYPE: DNA
<213> ORGANISM: Artificial
<220> FEATURE:
<223> OTHER INFORMATION: LRP6 Reverse Primer

<400> SEQUENCE: 33
cgacttgaac catccattcc                                               20

<210> SEQ ID NO 34
<211> LENGTH: 20
<212> TYPE: DNA
<213> ORGANISM: Artificial
<220> FEATURE:
<223> OTHER INFORMATION: Beta-Actin Forward Primer

<400> SEQUENCE: 34
agagcaagag aggcatcctc                                               20

<210> SEQ ID NO 35
<211> LENGTH: 20
<212> TYPE: DNA
<213> ORGANISM: Artificial
<220> FEATURE:
<223> OTHER INFORMATION: Beta-Actin Reverse Primer

<400> SEQUENCE: 35
ctcaaacatg atctgggtca                                               20
```

METHODS FOR PREDICTING LATE ONSET ALZHEIMER DISEASE IN AN INDIVIDUAL

FIELD

The present invention provides methods for diagnosis or prognosis of late onset Alzheimer disease in an individual which comprise detecting at least one polymorphism of a low-density lipoprotein receptor related protein 6 gene.

BACKGROUND

Inheritance of the Apolipoprotein E-ε4 (APOE-ε4) allele is a risk factor for Alzheimer disease (AD). Corder et al., *Science* 261: 921-3, 1993. Nevertheless, epidemiological studies estimate that 42-68% of AD sufferers do not present the APOE-ε4 allele, suggesting that additional genetic or environmental factors could play essential roles in the disease. Warwick Daw et al., *Am J Hum Genet* 66: 196-204, 2000. A fact consistent with this observation is that genome-wide screens have identified several regions that show significant linkage to AD, of which the most likely to harbor new risk factors are chromosomes 10 and 12. Pericak-Vance et al., *JAMA* 278: 1237-41, 1997; Rogaeva et al., *JAMA* 280: 614-8, 1998; Wu et al., *JAMA* 280: 619-22, 1998; Kehoe et al., *Hum Mol Genet* 8: 237-45, 1999; Scott et al., *Am J Hum Genet* 66: 922-32, 2000; Myers et al., *Am J Med Genet* 114: 235-44, 2002; Mayeux et al., *Am J Hum Genet* 70: 237-43, 2002; Blacker et al., *Hum Mol Genet* 12: 23-32, 2003. Low density lipoprotein receptor related protein 6 (LRP6), a co-receptor for Wnt signaling, is located on chromosome 12. Brown et al., *Biochem Biophys Res Commun* 248: 879-88, 1998; Pinson et al., *Nature* 407: 535-8, 2000; Tamai et al., *Nature* 407: 530-5, 2000; Wehrli et al., *Nature* 407: 527-30, 2000.

The reported linkage peaks for chromosome 12 show significant association to AD only when samples had been stratified according to APOE carrier status and cluster into two distinct regions (see candidate genes showing association to AD. One region is located at the p-ter, from ~6-30 cM, in the same vicinity as the α-2-macroglobulin gene (located at ~20 cM). Saunders et al, *Hum Mol Genet* 12: 2765-76, 2003. The other region is pericentromeric, from ~48-68 cM close to the LRP1 gene (~68 cM). The loss of Wnt signalling function may underlie AD. De Ferrari & Inestrosa, *Brain Res. Rev.* 33: 1-12, 2000; Mudher & Lovestone, *Trends Neuroset* 25: 22-6, 2002; Caricasole et al., *Trends Pharmacol Sci* 24: 233-8, 2003; Moon et al., *Nat Rev Genet* 5: 691-701, 2004. A need exists in the art to further examine and identify risk factors and genes that are associated with AD.

SUMMARY

Methods for diagnosis or prognosis of late onset Alzheimer disease in an individual are provided which comprise detecting one or more polymorphisms of a low-density lipoprotein receptor related protein 6 gene, wherein the presence of the one or more polymorphisms is diagnostic or prognostic of a patient's relative risk of late onset Alzheimer disease.

Genome-wide linkage studies have defined a broad susceptibility region for late-onset Alzheimer disease (AD) on chromosome 12, which contains the low density lipoprotein receptor related protein 6 (LRP6), a co-receptor for Wnt signalling. The reported linkage peaks for chromosome 12 show significant association to AD only when samples had been stratified according to APOE carrier status and cluster into two distinct regions. In this study, a linkage region associated with AD has been identified located in the region located at the p-ter, from ~6-30 cM, in particular, at the low density lipoprotein receptor related protein 6 (LRP6) gene (at ~26 cM) The LRP6 gene is in the same vicinity as the α-2-macroglobulin gene (located at ~20 cM), also associated with AD. Functional analyses revealed that LRP6 14e alleles display differential Wnt signalling activity and that LRP6 is normally expressed in adult human hippocampus. The data supports the notion that altered Wnt signalling function is central to the onset of this neurodegenerative disease.

A method for diagnosis or prognosis of late onset Alzheimer disease in an individual is provided which comprises detecting at least one polymorphism of a low-density lipoprotein receptor related protein 6 gene, wherein the presence of the at least one polymorphism is diagnostic or prognostic of a patient's relative risk of late onset Alzheimer disease.

In one aspect, the method further comprises identifying at least one single nucleotide polymorphism in the low-density lipoprotein receptor related protein 6 gene. In a further aspect, the at least one single nucleotide polymorphism is within exon 14 of the low-density lipoprotein receptor related protein 6 gene. Within exon 14, the at least one single nucleotide polymorphism includes, but is not limited to, a polymorphism corresponding to lrp6-14e: rs2302685, an A to G substitution at nucleotide 3184 of SEQ ID NO:1. Within exon 14, the at least one single nucleotide polymorphism includes, but is not limited to, a polymorphism corresponding to an isoleucine to valine substitution at amino acid 1062 of SEQ ID NO:2. In a further aspect, the at least one single nucleotide polymorphism is within exon 18 of the low-density lipoprotein receptor related protein 6 gene. Within exon 18, the at least one single nucleotide polymorphism includes, but is not limited to, a polymorphism corresponding to lrp6-18e:rs1012672, a C to T substitution at nucleotide 3810 of SEQ ID NO:3.

In another aspect, the method further comprises detecting at least one apolipoprotein E gene allele, wherein the at least one apolipoprotein E gene allele is correlated with diagnosis or prognosis of late onset Alzheimer disease. The method further provides wherein the at least one apolipoprotein E gene allele is apolipoprotein E allele 4 positive or wherein the at least one apolipoprotein E gene allele is apolipoprotein E allele 4 negative.

For the detecting step of the method, the at least one polymorphism of a low-density lipoprotein receptor related protein 6 gene is carried out by techniques of polymerase chain reaction, hybridization, Southern blotting onto membrane, digestion with nucleases, restriction fragment length polymorphism, or direct sequencing, or combinations thereof. In a further aspect of the method, the detecting step comprises extracting DNA of the individual, amplifying the isolated DNA using primers capable of amplifying the sequence corresponding to an lrp6-14e: rs2302685 polymorphism, an A to G substitution at nucleotide 3184 of SEQ ID NO:1 of the LRP6 gene, and determining the presence of at least one of the alleles of the lrp6-14e: rs2302685 polymorphism of the LRP6 gene in the amplified DNA. In a detailed aspect the amplified DNA carrying the allele of the lrp6-14e: rs2302685 polymorphism is distinguished from the amplified DNA not carrying the allele of the lrp6-14e: rs2302685 polymorphism by a technique using a 5' nuclease activity of DNA polymerase I. In a further detailed aspect, the amplified DNA carrying the allele of the lrp6-14e: rs2302685 polymorphism is distinguished from the amplified DNA not carrying the allele of the lrp6-14e: rs2302685 polymorphism by restriction fragment polymorphism analysis. In a further detailed aspect, the amplified DNA carrying the allele of the lrp6-14e: rs2302685 polymorphism is distinguished from the amplified DNA not carrying the allele of the lrp6-14e: rs2302685 polymorphism by polymerase chain reaction.

In a further aspect of the method, the detecting step comprises extracting DNA of the individual, amplifying the isolated DNA using primers capable of amplifying the sequence corresponding to an lrp6-18e: rs1012672 polymorphism, a C to T substitution at nucleotide 3810 of SEQ ID NO:3 of the LRP6 gene, and determining the presence of at least one of the alleles of the lrp6-18e: rs1012672 polymorphism of the LRP6 gene in the amplified DNA. In a further detailed aspect, the amplified DNA carrying the allele of the lrp6-18e: rs1012672 polymorphism is distinguished from the amplified DNA not carrying the allele of the lrp6-18e: rs1012672 polymorphism by a technique using a 5' nuclease activity of DNA polymerase I. In a further detailed aspect, the amplified DNA carrying the allele of the lrp6-18e: rs1012672 polymorphism is distinguished from the amplified DNA not carrying the allele of the lrp6-18e: rs1012672 polymorphism by restriction fragment polymorphism analysis. In a further detailed aspect, the amplified DNA carrying the allele of the lrp6-18e: rs1012672 polymorphism is distinguished from the amplified DNA not carrying the allele of the lrp6-18e: rs1012672 polymorphism by polymerase chain reaction.

A method of detecting an increased susceptibility to late onset Alzheimer disease in an individual is provided which comprises analyzing a DNA sample from the individual for the presence of at least one single nucleotide polymorphism of a low-density lipoprotein receptor related protein 6 gene sequence, wherein the presence of the at least one single nucleotide polymorphism is indicative of an increased susceptibility to late onset Alzheimer disease. In one aspect, the at least one single nucleotide polymorphism is a lrp6-14e: rs2302685 polymorphism, an A to G substitution at nucleotide 3184 of SEQ ID NO:1. In a further aspect, the at least one single nucleotide polymorphism is a lrp6-18e:rs1012672 polymorphism, a C to T substitution at nucleotide 3810 of SEQ ID NO:3. In a further aspect, the at least one single nucleotide polymorphism is a polymorphism corresponding to an isoleucine to valine substitution at amino acid 1062 of SEQ ID NO:2.

The method provided for detecting an increased susceptibility to late onset Alzheimer disease in an individual further comprises determining the presence in the nucleic acid sample of at least one apolipoprotein E gene allele. In one aspect, the at least one apolipoprotein E gene allele is apolipoprotein E allele 4 positive. In another aspect, the at least one apolipoprotein E gene allele is apolipoprotein E allele 4 negative.

The method provided for detecting an increased susceptibility to late onset Alzheimer disease in an individual further comprises performing a pedigree analysis by analyzing DNA samples obtained from family members of the test individual for the presence of the DNA polymorphism and correlating the presence or absence of the DNA polymorphism with a phenotypic diagnosis of late onset Alzheimer disease for the individual, wherein a correlation indicates that the test individual has an increased susceptibility to develop late onset Alzheimer disease. In one aspect, the at least one single nucleotide polymorphism is a lrp6-14e: rs2302685 polymorphism, an A to G substitution at nucleotide 3184 of SEQ ID NO:1. In a further aspect, the at least one single nucleotide polymorphism is a lrp6-18e:rs1012672 polymorphism, a C to T substitution at nucleotide 3810 of SEQ ID NO:3. In a further aspect, the at least one single nucleotide polymorphism is a polymorphism corresponding to an isoleucine to valine substitution at amino acid 1062 of SEQ ID NO:2.

The method provided for detecting an increased susceptibility to late onset Alzheimer disease in an individual further comprises determining the presence in the nucleic acid sample of at least one apolipoprotein E gene allele. In one aspect, the at least one apolipoprotein E gene allele is apolipoprotein E allele 4 positive. In another aspect, the at least one apolipoprotein E gene allele is apolipoprotein E allele 4 negative.

A method of screening compounds useful for modulation of risk of late onset Alzheimer disease is provided which comprises contacting a compound with a cultured host cell or membrane thereof that expresses a low-density lipoprotein receptor related protein 6 or domain thereof, in the presence of labeled or unlabeled Wnt or Frizzled or homolog thereof, determining whether the compound changes binding of the Wnt or Frizzled receptor or homolog thereof to the LRP6 or domain thereof by measuring an amount of Wnt or Frizzled receptor or homolog thereof bound to the LRP6 or domain thereof, and identifying the compound as a candidate useful for modulation of risk of late onset Alzheimer disease, whereby the compound causes a change in binding of the Wnt or Frizzled or homolog thereof. A method of making a pharmaceutical composition useful for modulation of risk of late onset Alzheimer disease comprises combining a pharmaceutically acceptable excipient and a compound identified by the screening method. A pharmaceutical composition comprises a compound identified by the screening method in combination with a pharmaceutically acceptable excipient.

An isolated nucleic acid is provided which comprises a nucleotide sequence coding for human LRP6 containing a lrp6-14e: rs2302685 polymorphism, an A to G substitution at nucleotide 3184 of SEQ ID NO:1. A nucleic acid probe is provided which hybridizes specifically to the isolated nucleic acid under stringent hybridization conditions wherein the stringent hybridization conditions prevent the nucleic acid probe from hybridizing to a wild-type DNA. A method for diagnosing a polymorphism in the LRP6 gene associated with late onset Alzheimer disease comprising hybridizing the nucleic acid probe to a patient's sample of DNA or RNA under stringent conditions which allow hybridization of the probe to nucleic acid comprising the polymorphism but prevent hybridization of the probe to a wild-type nucleic acid, wherein the presence of a hybridization signal indicates the presence of the polymorphism in the LRP6 gene associated with late onset Alzheimer disease. For the diagnostic method, the stringent hybridization conditions further comprise hybridization of the nucleic acid probe to the isolated DNA at 42° C. in a solution comprising: 50% formamide, 5×SSC (150 mM NaCl, 15 mM trisodium citrate), 50 mM sodium phosphate pH 7.6, 5× Denhardt's solution, 10% dextran sulfate, and 20 µg/ml denatured, sheared salmon sperm DNA, followed by washing the filters in 0.1×SSC at about 65° C. For the diagnostic method, the patient's DNA or RNA can be amplified and the amplified DNA or RNA can be hybridized to the probe. In a further aspect, hybridization is performed in situ. In a further aspect, a host comprises the isolated nucleic acid comprising a nucleotide sequence coding for human LRP6 containing a lrp6-14e: rs2302685 polymorphism, an A to G substitution at nucleotide 3184 of SEQ ID NO:1. In a detailed aspect, the host is a transformed or transfected cell. In a further detailed aspect, the host is a nonhuman transgenic animal.

An isolated nucleic acid is provided comprising a nucleotide sequence coding for human LRP6 containing a lrp6-18e:rs1012672 polymorphism, a C to T substitution at nucleotide 3810 of SEQ ID NO:3. A nucleic acid probe is provided which hybridizes specifically to the nucleic acid under stringent hybridization conditions wherein the stringent hybridization conditions prevent the nucleic acid probe from hybridizing to a wild-type DNA. A method for diagnosing a polymorphism in the LRP6 gene associated with late onset Alzheimer disease is provided which comprises hybridizing the nucleic acid probe to a patient's sample of DNA or RNA under stringent conditions which allow hybridization of the probe to nucleic acid comprising the polymorphism but prevent hybridization of the probe to a wild-type nucleic acid, wherein the presence of a hybridization signal indicates the presence of the polymorphism in the LRP6 gene associated with late onset Alzheimer disease.

A method for diagnosing the presence of a polymorphism in human LRP6 gene associated with late onset Alzheimer disease wherein the method to identify the presence of a polymorphism is a single-stranded conformation polymorphism assay comprises sequencing a human LRP6 gene or an amplified fragment thereof which contains the polymorphism, hybridizing an allele specific probe, and amplifying a human LRP6 gene fragment containing the polymorphism, cutting the amplified fragment with a restriction enzyme and determining the restriction pattern, wherein the presence of a polymorphism in human LRP6 gene associated with late onset Alzheimer disease is diagnosed.

A method for treating late onset Alzheimer disease is provided which comprises detecting the presence of a lrp6-14e: rs2302685 polymorphism, an A to G substitution at nucleotide 3184 of SEQ ID NO:1 of an LRP6 gene, or a lrp6-18e: rs1012672 polymorphism, a C to T substitution at nucleotide 3810 of SEQ ID NO:3 of an LRP6 gene in an individual, and administering a compound or of a mixture of compounds known for their activity against late onset Alzheimer disease to an individual exhibiting the lrp6-14e: rs2302685 polymorphism, or the lrp6-18e:rs1012672 polymorphism, wherein symptoms of late onset Alzheimer disease are treated.

In one aspect, the compound is an agonist of a Wnt/β-catenin signaling pathway. In an detailed aspect, the compound is a polypeptide, nucleic acid, small molecule, antisense oligonucleotide, ribozyme, RNAi construct, siRNA, shRNA, or antibody. In a further detailed aspect, the compound is an LRP6 polypeptide, a wnt polypeptide, a dishevelled polypeptide, or a β-catenin polypeptide. In a further aspect, the compound is a glycogen synthase kinase (GSK) inhibitor, wherein the GSK inhibitor includes, but is not limited to, a GSK-3 inhibitor, a GSK-3β inhibitor, or LiCl.

BRIEF DESCRIPTION OF THE DRAWINGS

FIGS. 5a and 5b show the complete DNA sequence of LRP6 gene(SEQ ID NO:1).

FIG. 6 shows the complete amino acid sequence of LRP6 protein (SEQ ID NO:2).

FIG. 7 shows the sequence of exon 14 of the LRP6 gene (SEQ ID NOs:3, 4, 5, 6).

FIG. 8 shows the sequence of exon 18 of the LRP6 gene (SEQ ID NOs:7, 8, 9).

DETAILED DESCRIPTION

1. Introduction

Figure 1:
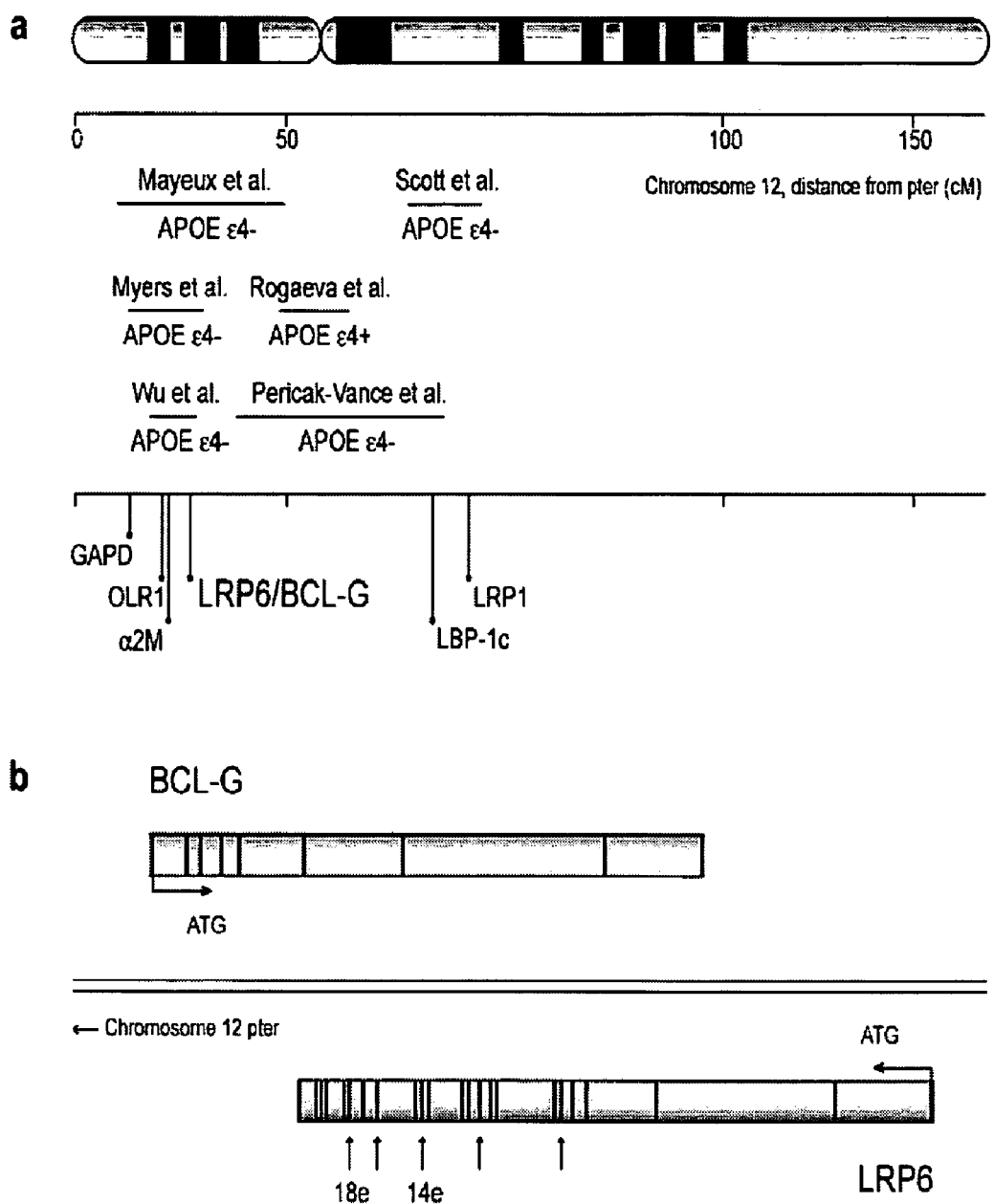
FIG. 1a and 1b show a relationship between late onset Alzheimer disease and chromosome 12.

Methods for diagnosis or prognosis of late onset Alzheimer disease in an individual are provided which comprise detecting at least one polymorphism of a low-density lipoprotein receptor related protein 6 gene, wherein the presence of the at least one polymorphism is diagnostic or prognostic of a patient's relative risk of late onset Alzheimer disease. In a further aspect, methods of detecting an increased susceptibility to late onset Alzheimer disease in an individual are provided which comprise analyzing a DNA sample from the individual for the presence of at least one single nucleotide polymorphism of a low-density lipoprotein receptor related protein 6 gene sequence, wherein the presence of the at least one single nucleotide polymorphism is indicative of an increased susceptibility to late onset Alzheimer disease.

The reported linkage peaks for chromosome 12 show significant association to AD only when samples had been stratified according to APOE carrier status and cluster into two distinct regions (FIG. 1A). One region is located at the p-ter, from ~6-30 cM, in the same vicinity as the α-2-macroglobulin gene (located at ~20 cM) and the low density lipoprotein receptor related protein 6 (LRP6) gene (at ~26 cM). Saunders et al., *Hum Mol Genet* 12: 2765-76, 2003. The other region is pericentromeric, from ~48-68 cM close to the LRP1 gene (~68 cM). It has been proposed that loss of Wnt signalling function may underlie AD, leading us to examine whether the LRP6 gene is associated with AD. De Ferrari & Inestrosa, *Brain Res Brain Res Rev* 33: 1-12, 2000; Mudher & Lovestone, *Trends Neurosci* 25: 22-6, 2002; Caricasole et al., *Trends Pharmacol Sci* 24: 233-8, 2003; Moon et al., *Nat Rev Genet* 5: 691-701, 2004.

Genome-wide linkage studies have defined a broad susceptibility region for late-onset Alzheimer disease (AD) on chromosome 12, which contains the low density lipoprotein receptor related protein 6 (LRP6), a co-receptor for Wnt signalling. Pericak-Vance et al., *JAMA* 278: 1237-41, 1997; Rogaeva et al., *JAMA* 280: 614-8, 1998; Wu et al., *JAMA* 280: 619-22, 1998; Kehoe et al., *Hum Mol Genet* 8: 237-45, 1999; Scott et al., *Am J Hum Genet* 66: 922-32, 2000; Myers et al., *Am J Med Genet* 114: 235-44, 2002; Mayeux et al., *Am J Hum Genet* 70: 237-43, 2002; Brown et al., *Biochem Biophys Res Commun* 248: 879-88, 1998; Pinson et al., *Nature* 407: 535-8, 2000; Tamai et al., *Nature* 407: 530-5, 2000; Wehrli et al., *Nature* 407: 527-30, 2000. In a large family-based series ascertained by the NIMH-NIA Genetics Initiative it has been found that LRP6 single nucleotide polymorphisms (SNPs) 14e (Ile1062→Val) and 18e (Cys1270→Cys) are significantly associated to late-onset AD in the Apolipoprotein E-ϵ4 (APOE-ϵ4) negative stratum. Functional analyses revealed that LRP6 14e alleles display differential Wnt signalling activity and that LRP6 is normally expressed in adult human hippocampus. The data supports the notion that altered Wnt signalling function is central to the onset of this neurodegenerative disease, for example, Alzheimer disease.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

"Trait" and "phenotype" are used interchangeably and refer to any visible, detectable or otherwise measurable property of an organism such as symptoms of, or susceptibility to a disease for example. Typically the terms "trait" or "phenotype" are used to refer to symptoms of, or susceptibility to a disease, a beneficial response to or side effects related to a treatment. Preferably, said trait can be, without being limited to, neurological conditions such as Alzheimer disease.

"Allele" refers to variants of a nucleotide sequence. A biallelic polymorphism has two forms. Diploid organisms may be homozygous or heterozygous for an allelic form.

"Heterozygosity rate" refers to the incidence of individuals in a population which are heterozygous at a particular allele. In a biallelic system, the heterozygosity rate is on average equal to $2P_a(1-P_a)$, where $P_a$ is the frequency of the least common allele. In order to be useful in genetic studies, a genetic marker should have an adequate level of heterozygosity to allow a reasonable probability that a randomly selected person will be heterozygous.

"Genotype" refers the identity of the alleles present in an individual or a sample. A genotype preferably refers to the description of the biallelic marker alleles present in an individual or a sample. "Genotyping" a sample or an individual for a biallelic marker involves determining the specific allele or the specific nucleotide carried by an individual at a biallelic marker.

"Mutation" refers to a difference in DNA sequence between or among different genomes or individuals which has a frequency below 1%.

"Haplotype" refers to a combination of alleles present in an individual or a sample. A haplotype preferably refers to a combination of biallelic marker alleles found in a given individual and which may be associated with a phenotype.

"Polymorphism" refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. A single nucleotide polymorphism is the replacement of one nucleotide by another nucleotide at the polymorphic site. Deletion of a single nucleotide or insertion of a single nucleotide also gives rise to single nucleotide polymorphisms. "Single nucleotide polymorphism" preferably refers to a single nucleotide substitution. Typically, between different individuals, the polymorphic site can be occupied by two different nucleotides.

"Biallelic polymorphism" and "biallelic marker" are used interchangeably to refer to a single nucleotide polymorphism having two alleles at a fairly high frequency in the population. A "biallelic marker allele" refers to the nucleotide variants present at a biallelic marker site. Typically, the frequency of the less common allele of the biallelic markers of the present invention has been validated to be greater than 1%, preferably the frequency is greater than 10%, more preferably the frequency is at least 20% (i.e. heterozygosity rate of at least 0.32), even more preferably the frequency is at least 30% (i.e. heterozygosity rate of at least 0.42). A biallelic marker wherein the frequency of the less common allele is 30% or more is termed a "high quality biallelic marker". "polypeptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups; acetyl groups, phosphate groups, lipid groups and the like are expressly encompassed by polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

"Recombinant polypeptide" is used herein to refer to polypeptides that have been artificially designed and which comprise at least two polypeptide sequences that are not found as contiguous polypeptide sequences in their initial natural environment, or to refer to polypeptides which have been expressed from a recombinant polynucleotide, i.e. using recombinant DNA methods.

"Mammal" or "mammalian subject" for purposes of the treatment of, alleviating the symptoms of or diagnosis of Alzheimer disease refers to any animal classified as a mammal, including humans, domestic and farm animals, and zoo, sports, or pet animals, such as dogs, cats, cattle, horses, sheep, pigs, goats, rabbits, etc. Preferably, the mammal is human. "Non-human animal" refers to any non-human vertebrate, birds and more usually mammals, preferably primates, farm animals such as swine, goats, sheep, donkeys, and horses, rabbits or rodents, more preferably rats or mice. As used herein, "animal" is used to refer to any vertebrate, preferable a mammal. Both the terms "animal" and "mammal" expressly embrace human subjects unless preceded with "non-human".

"Antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

"Antigenic determinant" is the portion of an antigen molecule that determines the specificity of the antigen-antibody reaction. An "epitope" refers to an antigenic determinant of a polypeptide. An epitope can comprise as few as 3 amino acids in a spatial conformation which is unique to the epitope. Generally an epitope comprises at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by Geysen et al. 1984; PCT Publication No. WO 84/03564; and PCT Publication No. WO 84/03506.

Throughout the present specification, "nucleotide sequence" can be employed to designate indifferently a polynucleotide or a nucleic acid. More precisely, "nucleotide sequence" encompasses the nucleic material itself and is thus not restricted to the sequence information (i.e. the succession of letters chosen among the four base letters) that biochemically characterizes a specific DNA or RNA molecule.

"Nucleic acids", "oligonucleotides", and "polynucleotides" include RNA, DNA, or RNA/DNA hybrid sequences of more than one nucleotide in either single chain or duplex form. "Nucleotide" as used herein as an adjective to describe molecules comprising RNA, DNA, or RNA/DNA hybrid sequences of any length in single-stranded or duplex form. "Nucleotide" is also used as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although "nucleotide" is also used herein to encompass "modified nucleotides" which comprise at least one modifications (a) an alternative linking group, (b) an analogous form of purine, (c) an analogous form of pyrimidine, or (d) an analogous sugar, for examples of analogous linking groups, purine, pyrimidines, and sugars see for example PCT publication No. WO 95/04064. The polynucleotide sequences of the invention may be prepared by any known method, including synthetic, recombinant, ex vivo generation, or a combination thereof, as well as utilizing any purification methods known in the art.

"Operably linked" refers to a linkage of polynucleotide elements in a functional relationship. For instance, a promoter or enhancer is operably linked to a coding sequence if it affects the transcription of the coding sequence.

2. Oligonucleotide Arrays

A substrate comprising a plurality of oligonucleotide primers or probes of the invention may be used, e.g., to detect expression of a plurality of any of the herein-provided cDNAs, or to detect the expression of one or more of the present cDNAs in conjunction with the expression of one or more heterologous genes.

Any polynucleotide provided herein can be attached in overlapping areas or at random locations on the solid support. Alternatively the polynucleotides of the invention may be attached in an ordered array wherein each polynucleotide is attached to a distinct region of the solid support which does not overlap with the attachment site of any other polynucleotide. Preferably, such an ordered array of polynucleotides is designed to be "addressable" where the distinct locations are recorded and can be accessed as part of an assay procedure. Addressable polynucleotide arrays typically comprise a plurality of different oligonucleotide probes that are coupled to a surface of a substrate in different known locations. The knowledge of the precise location of each polynucleotides location makes these "addressable" arrays particularly useful in hybridization assays. Any addressable array technology known in the art can be employed with the polynucleotides of the invention. One particular embodiment of these polynucleotide arrays is known as the Genechips™, and has been generally described in U.S. Pat. No. 5,143,854; PCT publications WO 90/15070 and 92/10092. These arrays may generally be produced using mechanical synthesis methods or light directed synthesis methods which incorporate a combination of photolithographic methods and solid phase oligonucleotide synthesis. Fodor et al., *Science* 251: 767-73, 1991. The immobilization of arrays of oligonucleotides on solid supports has been rendered possible by the development of a technology generally identified as "Very Large Scale Immobilized Polymer Synthesis" (VSLSIPS™) in which, typically, probes are immobilized in a high density array on a solid surface of a chip. Examples of VLSIPS™ technologies are provided in U.S. Pat. Nos. 5,143,854; and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and sequence information. Examples of such presentation strategies are disclosed in PCT Publications WO 94/12305, WO 94/11530, WO 97/29212 and WO 97/31256, the disclosures of which are incorporated herein by reference in their entireties.

Consequently, the invention concerns an array of nucleic acid molecules comprising at least one polynucleotide described above as probes and primers. Preferably, the invention concerns an array of nucleic acid comprising at least two polynucleotides described above as probes and primers.

3. Identification of Modulators of Wnt/b-catenin Signaling

"Activators," "inhibitors," and "modulators" of signaling via low density lipoprotein receptor-related protein 6, e.g., Wnt/β-catenin signaling, Notch signaling or Hedgehog signaling are used to refer to activating, or modulating molecules, respectively, identified using in vitro and in vivo assays for signaling via low density lipoprotein receptor-related protein 6, e.g., Wnt/β-catenin signal-, Notch signal- or Hedgehog signal-promoting agents, e.g., ligands, agonists, antagonists, and their homologs and mimetics. "Modulator" includes inhibitors and activators. Inhibitors are agents that, e.g., bind to, partially or totally block stimulation, decrease, prevent, delay activation, inactivate, desensitize, or down regulate the activity of signaling via low density lipoprotein receptor-related protein 6, for example, Wnt/β-catenin signaling, Notch signaling or Hedgehog signaling, e.g., antagonists. Activators are agents that, e.g., bind to, stimulate, increase, open, activate, facilitate, enhance activation, sensitize or up regulate the activity of signaling via low density lipoprotein receptor-related protein 6, for example, Wnt/β-catenin signaling, Notch signaling or Hedgehog signaling, e.g., agonists. Modulators include agents that, e.g., alter the interaction of signaling via low density lipoprotein receptor-related protein 6, for example, Wnt/-catenin, Notch, or Hedgehog with: proteins that bind activators or inhibitors, receptors, including proteins, peptides, lipids, carbohydrates, polysaccharides, or combinations of the above, e.g., lipoproteins, glycoproteins, and the like. Modulators include genetically modified versions of naturally-occurring low density lipoprotein receptor-related protein 6 polypeptides, Wnt/β-catenin, Notch, or Hedgehog ligands, e.g., Wnt, β-catenin, Notch, or Hedgehog polypeptides with altered activity, as well as naturally occurring and synthetic ligands, antagonists, agonists, small chemical molecules and the like. Such assays for inhibitors and activators include, e.g., applying putative modulator compounds to a cell expressing low density lipoprotein receptor-related protein 6, Wnt/β-catenin, Notch, or Hedgehog and then determining the functional effects on signaling via low density lipoprotein receptor-related protein 6, for example, Wnt/β-catenin signaling, Notch signaling or Hedgehog signaling, as described herein. Samples or assays comprising signaling via low density lipoprotein receptor-related protein 6, for example, Wnt/β-catenin signaling, Notch signaling or Hedgehog signaling that are treated with a potential activator, inhibitor, or modulator are compared to control samples without the inhibitor, activator, or modulator to examine the extent of inhibition. Control samples (untreated with activators, inhibitors, or modulators) can be assigned a relative low density lipoprotein receptor-related protein 6 activity, Wnt/β-catenin, Notch, or Hedgehog activity value of 100%. Inhibition of signaling via low density lipoprotein receptor-related protein 6, for example, Wnt/β-catenin signaling, Notch signaling or Hedgehog signaling is achieved when the low density lipoprotein receptor-related protein 6, Wnt/β-catenin, Notch, or Hedgehog activity value relative to the control is about 80%, optionally 50% or 25-0%. Activation of signaling via low density lipoprotein receptor-related protein 6, for example, Wnt/β-catenin signaling, Notch signaling or Hedgehog signaling is achieved when the low density lipoprotein receptor-related protein 6, Wnt/β-catenin, Notch, or Hedgehog activity value relative to the control is 110%, optionally 150%, optionally 200-500%, or 1000-3000% higher. Activation of signaling via low density lipoprotein receptor-related protein 6, for example, Wnt/β-catenin signaling, Notch signaling or Hedgehog signaling can be measured in a cellular assay for increasing brain cells in vivo in a mammalian subject or increasing cells of the hippocampus or forebrain in vivo in a mammalian subject, as described herein.

"Agonist" is used in the broadest sense and includes any molecule that mimics or enhances a biological activity of low density lipoprotein receptor-related protein 6, Wnt/β-catenin, Notch, or Hedgehog polypeptides, or signaling via low density lipoprotein receptor-related protein 6, for example, Wnt/β-catenin signaling, Notch signaling or Hedgehog signaling. Suitable agonist molecules specifically include agonist antibodies or antibody fragments, fragments or amino acid sequence variants of native low density lipoprotein receptor-related protein 6, Wnt, β-catenin, Notch, or Hedgehog polypeptides, peptides, antisense oligonucleotides, small organic molecules, and the like. Methods for identifying agonists of low density lipoprotein receptor-related protein 6, Wnt, β-catenin, Notch, or Hedgehog polypeptides can comprise contacting a low density lipoprotein receptor-related protein 6, Wnt, β-catenin, Notch, or Hedgehog polypeptide with a candidate agonist molecule and measuring a detectable change in one or more biological activities normally associated with the signaling via low density lipoprotein receptor-related protein 6, for example, Wnt/β-catenin signaling, Notch signaling or Hedgehog signaling, e.g., Wnt binding to the Frizzled receptor, or intracellular accumulation of β-catenin.

"Antagonist" is used in the broadest sense, and includes any molecule that partially or fully blocks, inhibits, or neutralizes an inhibitor of a biological activity of a low density lipoprotein receptor-related protein 6, Wnt, β-catenin, Notch, or Hedgehog polypeptide, or signaling via low density lipoprotein receptor-related protein 6, for example, Wnt/β-catenin signaling, Notch signaling or Hedgehog signaling. Suitable antagonist molecules specifically include antagonist antibodies or antibody fragments, fragments or amino acid sequence variants of native polypeptides, peptides, antisense oligonucleotides, small organic molecules, and the like. Methods for identifying antagonists of an inhibitor of a biological activity of a Wnt, β-catenin, Notch, or Hedgehog polypeptide, or of signaling via low density lipoprotein receptor-related protein 6, for example, Wnt- or β-catenin-signaling can comprise contacting Wnt, β-catenin, Notch, or Hedgehog polypeptides, or signaling via low density lipoprotein receptor-related protein 6, for example, Wnt- or β-catenin-signaling polypeptides with a candidate antagonist molecule and measuring a detectable change in one or more biological activities normally associated with signaling via low density lipoprotein receptor-related protein 6, for example, Wnt/β-catenin signaling, Notch signaling or Hedgehog signaling.

"Signaling in cells" refers to the interaction of a ligand, such as an endogenous or exogenous ligand, e.g., Notch signal-promoting or Hedgehog signal-promoting, or signaling via low density lipoprotein receptor-related protein 6, for example, Wnt signal-promoting or β-catenin signal-promoting agents, with receptors, such as Frizzled receptor, resulting in cell signaling to produce a response, for example, increasing expression of β-catenin target genes resulting in increased brain cells, hippocampus cells or forebrain cells in vivo in a mammalian subject.

"Endogenous" refers a protein, nucleic acid, lipid or other component produced within the body or within cells or organs of the body of a mammalian subject or originating within cells or organs of the body of a mammalian subject.

"Exogenous" refers a protein, nucleic acid, lipid, or other component originating outside the body of a mammalian subject.

"Test compound" refers to a nucleic acid, DNA, RNA, protein, polypeptide, or small chemical entity that is determined to effect an increase or decrease in a gene expression as a result of signaling through the signaling via low density lipoprotein receptor-related protein 6, for example, Wnt/β-catenin signaling, Notch signaling or Hedgehog signaling pathways. The test compound can be an antisense RNA, ribozyme, polypeptide, or small molecular chemical entity. "Test compound" can be any small chemical compound, or a biological entity, such as a protein, sugar, nucleic acid or lipid. Typically, test compounds will be small chemical molecules and polypeptides. A "test compound specific for signaling via low density lipoprotein receptor-related protein 6, for example, Wnt/β-catenin signaling, Notch signaling or Hedgehog signaling" is determined to be a modulator of Notch signaling or Hedgehog signaling or signaling via low density lipoprotein receptor-related protein 6, for example, Wnt signaling or β-catenin signaling, for example, resulting in Wnt binding to the Frizzled receptor, or intracellular accumulation of β-catenin.

"Cell-based assays" include signaling via low density lipoprotein receptor-related protein 6, for example, Wnt/β-catenin signaling, Notch signaling or Hedgehog signaling assays, for example, radioligand or fluorescent ligand binding assays for Wnt, β-catenin, Notch, or Hedgehog to cells, plasma membranes, detergent-solubilized plasma membrane proteins, immobilized collagen (Alberdi, *J Biol Chem.* 274: 31605-12, 1999; Meyer et al., 2002); Wnt, β-catenin, Notch, or Hedgehog-affinity column chromatography (Alberdi, *J Biol Chem.* 274: 31605-12, 1999; Aymerich et al., *Invest Ophthalmol Vis Sci.* 42: 3287-93, 2001); Wnt, β-catenin, Notch, or Hedgehog blot using a radio- or fluoresceinated-ligand (Aymerich et al., *Invest Ophthalmol Vis Sci.* 42: 3287-93, 2001; Meyer et al., 2002); Size-exclusion ultrafiltration (Alberdi et al., 1998, *Biochem.*; Meyer et al., 2002); or ELISA. Cellular assay to measure increasing brain cells, hippocampus cells or forebrain cells in vivo in a mammalian subject, or increasing Wnt/β-catenin activity in cells. as described herein. Multilineage donor HSC reconstitution was examined by flow cytometry for surface markers representing primitive (c-Kit+Sca-1+), myeloid (CD45+CD11b+), erythroid (CD45−Ter119+), B cell (CD45+B220+), and T cell (CD45+CD3+) lineages indicating multilineage donor HSC reconstitution. Exemplary signaling via low density lipoprotein receptor-related protein 6, for example, Wnt/β-catenin signaling, Notch signaling or Hedgehog signaling activity assays of the present invention are: Assays for Wnt-regulated target gene Axin2 quantified by real-time PCR; Yan et al., *Proc Natl Acad Sci USA* 98: 14973-8, 2001; Jho et al., *Mol Cell Biol* 22: 1172-83, 2002. Wnt-regulated target gene CyclinD1 quantified by real-time PCR; Issack and Ziff, *Cell Growth Differ* 9: 837-45, 1998. Notch regulated target gene, Hes1, quantified by real-time PCR; Jarriault et al., *Nature* 377: 355-8, 1995. Hedgehog regulated target genes, Gli3 and Patched1 (Ptc1), quantified by real-time PCR. Marigo et al., 180 1: 1996; Marigo and Tabin, *Proc Natl Acad Sci USA* 93: 9346-9351, 1996, each incorporated by reference in their entirety. Further cell based assays include but are not limited to, luciferase, green fluorescent protein (GFP), or β-galactosidase reporter screens for β-catenin responsive genes, for example using TOPFLASH reporter. See, for example, Veeman et al., *Current Biology* 13: 680-685, 2003; Veeman et al., *Dev Cell.* 5: 367-377, 2003, each incorporated by reference in their entirety.

In one aspect, a method of screening drug candidates to promote signaling via low density lipoprotein receptor-related protein 6, for example, Wnt/β-catenin signal-, Notch signal- or Hedgehog signal-promoting agents is provided and comprise, for example, a β-catenin-responsive gene reporter assay in which a reporter DNA construct consists of TCF or LEF binding sites upstream of a minimal promoter, and drives expression of luciferase, GFP, or β-galactosidase. Luciferase, GFP, or β-galactosidase is used as a surrogate to demonstrate increased activity of β-catenin signaling, as measured by the reporter protein fluorescence or enzymatic means. Further methods of screening drug candidates to promote signaling via low density lipoprotein receptor-related protein 6, for example, Wnt signal- or β-catenin signal-promoting agents involve an assay to measure Wnt binding to the Frizzled receptor, or intracellular accumulation of β-catenin. Wnt binding to the Frizzled receptor or intracellular accumulation of β-catenin can be assayed by either immobilizing the ligand or the receptor. For example, the assay can include immobilizing Frizzled receptor fused to a His tag onto Ni-activated NTA resin beads. Low density lipoprotein receptor-related protein 6 can be added in an appropriate buffer and the beads incubated for a period of time at a given temperature. After washes to remove unbound material, the bound protein can be released with, for example, SDS, buffers with a high pH, and the like and analyzed. For example, the Wnt signal- or β-catenin signal-promoting agent promotes Wnt binding to the Frizzled receptor or intracellular accumulation of β-catenin.

"Interacting" refers to mixing a test compound, e.g., one or more compounds signaling via low density lipoprotein receptor-related protein 6, for example, Wnt/β-catenin signal-, Notch signal- or Hedgehog signal-promoting agents, in a soluble form into an assay system, for example, a cell-based assay system, such that an effect upon receptor-mediated signaling or intracellular signaling can be measured. For example, the "interacting" step can occur directly by contacting the brain cells, hippocampus cells or forebrain cells and the one or more Wnt/β-catenin signal-, Notch signal- or Hedgehog signal-promoting agents to induce signaling via low density lipoprotein receptor-related protein 6 within the brain cells, hippocampus cells or forebrain cells. Alternatively, the "interacting" step can occur indirectly between a brain cells, hippocampus cells or forebrain cells and the low density lipoprotein receptor-related protein 6 signal-, Wnt/β-catenin signal-, Notch signal- or Hedgehog signal-promoting agents, for example, through an intermediary signaling molecule, receptor, ligand, growth factor, or cell type, that affects, or is affected by, signaling via low density lipoprotein receptor-related protein 6, for example, Wnt/β-catenin signaling, Notch signaling or Hedgehog signaling.

"Signaling responsiveness" or "effective to activate signaling" or "stimulating a cell-based assay system" refers to the ability of low density lipoprotein receptor-related protein 6 signal-, Wnt/β-catenin signal-, Notch signal- or Hedgehog signal-promoting agent to enhance or increase growth or development of brain cells, hippocampus cells or forebrain cells in vivo in a mammalian subject, or to treat Alzheimer disease or late-onset Alzheimer disease in a mammalian subject.

"Detecting an effect" refers to an effect measured in a cell-based assay system. For example, the effect detected can be signaling via low density lipoprotein receptor-related protein 6, for example, Wnt/β-catenin signaling, Notch signaling or Hedgehog signaling in an assay system, for example, Wnt, β-catenin, Notch, or Hedgehog cellular assay, Frizzled receptor binding assay, Axin2 assay, or CyclinD1 assay, or β-catenin-responsive gene reporter assay. See, for example, Veeman et al., *Current Biology* 13: 680-685, 2003; Veeman et al., *Dev Cell.* 5: 367-377, 2003, each incorporated by reference in their entirety.

"Assay being indicative of modulation" refers to results of a cell-based assay system indicating that cell activation by low density lipoprotein receptor-related protein 6 signal-, Wnt/β-catenin signal-, Notch signal- or Hedgehog signal-promoting agents are indicated to treat Alzheimer disease or late-onset Alzheimer disease in a mammalian subject by increasing brain cells, hippocampus cells or forebrain cells in vivo in a mammalian subject or treating Alzheimer disease or late-onset Alzheimer disease in a mammalian subject by increasing Wnt/β-catenin signaling in brain cells, hippocampus cells or forebrain cells.

"Biological activity" and "biologically active" with regard to low density lipoprotein receptor-related protein 6 signal-, Wnt/β-catenin signal-, Notch signal- or Hedgehog signal-promoting agents of the present invention refer to the ability of the ligand molecule to specifically bind to and signal through a native or recombinant low density lipoprotein receptor-related protein 6, Wnt, β-catenin, Notch, or Hedgehog, or to block the ability of an inhibitor of native or recombinant low density lipoprotein receptor-related protein 6, Wnt/β-catenin, Notch, or Hedgehog polypeptides to participate in signal transduction. Thus, the (native and variant) low density lipoprotein receptor-related protein 6 signal-, Wnt/β-catenin signal-, Notch signal- or Hedgehog signal-promoting agents of the present invention include agonists of a native or recombinant low density lipoprotein receptor-related protein 6, Wnt, β-catenin, Notch, or Hedgehog polypeptides and receptors or ligands thereof. Preferred biological activities of the low density lipoprotein receptor-related protein 6 signal-, Wnt/β-catenin signal-, Notch signal- or Hedgehog signal-promoting agents of the present invention include the ability to induce or inhibit, for example, increasing growth or development of brain cells, hippocampus cells or forebrain cells in vivo in a mammalian subject or treating Alzheimer disease or late-onset Alzheimer disease in a mammalian subject. Accordingly, the administration of the compounds or agents of the present invention can prevent or delay, to alleviate, or to arrest or inhibit development of the symptoms or conditions associated with Alzheimer disease or late-onset Alzheimer disease in a mammalian subject.

"Signal transduction pathway" or "signal transduction event" refers to at least one biochemical reaction, but more commonly a series of biochemical reactions, which result from interaction of a cell with a stimulatory compound or agent. Thus, the interaction of a stimulatory compound with a cell generates a "signal" that is transmitted through the signal transduction pathway, ultimately resulting in a cellular response, e.g., signaling via Wnt/β-catenin pathway.

"High affinity" for a ligand refers to an equilibrium association constant (Ka) of at least about $10^3 M^{-1}$, at least about $10^4 M^{-1}$, at least about $10^5 M^-$, at least about $10^6 M^{-1}$, at least about $10^7 M^{-1}$, at least about $10^8 M^{-1}$, at least about $10^9 M^{-1}$, at least about $10^{10} M^-$, at least about $10^{11} M^{-1}$, or at least about $10^{12} M^{-1}$ or greater, e.g., up to $10^{13} M^{-1}$ or $10^{14} M^{-1}$ or greater. However "high affinity" binding can vary for other ligands.

"$K_a$", as used herein, is intended to refer to the equilibrium association constant of a particular ligand-receptor interaction, e.g., antibody-antigen interaction. This constant has units of 1/M.

"$K_d$", as used herein, is intended to refer to the equilibrium dissociation constant of a particular ligand-receptor interaction. This constant has units of M.

"$k_a$", as used herein, is intended to refer to the kinetic association constant of a particular ligand-receptor interaction. This constant has units of 1/Ms.

"$k_d$", as used herein, is intended to refer to the kinetic dissociation constant of a particular ligand-receptor interaction. This constant has units of 1/s.

"Particular ligand-receptor interactions" refers to the experimental conditions under which the equilibrium and kinetic constants are measured.

"Isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$)

The ability of a molecule to bind to low density lipoprotein receptor-related protein 6, Wnt, β-catenin, Notch, or Hedgehog can be determined, for example, by the ability of the putative ligand to modulate Wnt binding to the Frizzled receptor, by measuring intracellular accumulation of β-catenin, Axin2 assay, or CyclinD1 assay. Specificity of binding can be determined by comparing binding in the presence or absence of the putative ligand.

"Control sequences" or "regulatory sequences" refers to DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

"Sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

"Cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny cannot be precisely identical in DNA content, due to deliberate or inadvertent mutations. Mutant progeny that have the same function or biological activity as screened for in the originally transformed cell are included. Where distinct designations are intended, it will be clear from the context.

"Receptor" denotes a cell-associated protein, for example Frizzled receptor, that binds to a bioactive molecule termed a "ligand." This interaction mediates the effect of the ligand on the cell. Receptors can be membrane bound, cytosolic or nuclear; monomeric (e.g., Frizzled receptor, thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors, for example Frizzled receptor, are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

"Treatment" or "treating" refers to any indicia of success in the treatment or amelioration of an injury, pathology or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination. Accordingly, "treatment" or "treating" includes the administration of the compounds or agents of the present invention to inhibit or enhance signaling via low density lipoprotein receptor-related protein 6, e.g., Wnt/β-catenin pathway, or treat Alzheimer disease or late-onset Alzheimer disease. Accordingly, "treatment" or "treating" includes the administration of the compounds or agents of the present invention to prevent or delay, to alleviate, or to arrest or inhibit development of the symptoms or conditions associated with Alzheimer disease, late-onset Alzheimer disease, or other disorders. "Therapeutic effect" refers to the reduction, elimination, or prevention of the disease, symptoms of the disease, or side effects of the disease in the subject.

"Concomitant administration" of a known drug with a compound of the present invention means administration of the drug and the compound at such time that both the known drug and the compound will have a therapeutic effect or diagnostic effect. Such concomitant administration can involve concurrent (i.e. at the same time), prior, or subsequent administration of the drug with respect to the administration of a compound of the present invention. A person of ordinary skill in the art, would have no difficulty determining the appropriate timing, sequence and dosages of administration for particular drugs and compounds of the present invention.

"Subject", "mammalian subject" or "patient" refers to any mammalian patient or subject to which the compositions of the invention can be administered. "Mammal" or "mammalian" refers to human patients and non-human primates, as well as experimental animals such as rabbits, rats, and mice, and other animals. In an exemplary embodiment, of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that can be associated with the targeted or suspected disease or condition. These and other routine methods allow the clinician to select patients in need of therapy using the methods and formulations of the invention.

By "solid phase" is meant a non-aqueous matrix to which a reagent of interest (e.g., low density lipoprotein receptor-related protein 6, Wnt, β-catenin, or Frizzled receptor, or an antibody thereto) can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g.,an affinity chromatography column). This term also includes a discontinuous solid phase of discrete particles, such as those described in U.S. Pat. No. 4,275,149.

"Specifically (or selectively) binds" to an antibody refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample.

"Specifically bind(s)" or "bind(s) specifically" when referring to a peptide refers to a peptide molecule which has intermediate or high binding affinity, exclusively or predominately, to a target molecule. The phrase "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions can require a binding moiety that is selected for its specificity for a particular target antigen. A variety of assay formats can be used to select ligands that are specifically reactive with a particular protein. For example, solid-phase ELISA immunoassays, immunoprecipitation, Biacore and Western blot are used to identify peptides that specifically affect signaling via low density lipoprotein receptor-related protein 6, for example, Wnt signaling, β-catenin signaling, or Frizzled receptor proteins. Typically a specific or selective reaction will be at least twice background signal or noise and more typically more than 10 times background. Specific binding between a monovalent peptide and signaling via low density lipoprotein receptor-related protein 6, for example, Wnt signaling, β-catenin signaling, or Frizzled receptor proteins means a binding affinity of at least $10^3$ $M^{-1}$, and preferably $10^5$, $10^6$, $10^7$, $10^8$, $10^9$ or $10^{10}$ $M^{-1}$. The binding affinity of Wnt to the Frizzled receptor is between about $10^6$ $M^{-1}$ to about $10^{10}$ $M^{-1}$.

4. Recombinant DNA Techniques

This invention relies on routine techniques in the field of recombinant genetics. Basic texts disclosing the general methods of use in this invention include Sambrook et al., *Molecular Cloning, A Laboratory Manual,* 2nd ed., 1989; Kriegler, *Gene Transfer and Expression: A Laboratory Manual,* 1990; and Ausubel et al., eds., *Current Protocols in Molecular Biology,* 1994.

Nucleic acids encoding low density lipoprotein receptor-related protein 6, polymorphic variants, orthologs, and alleles that are substantially identical to sequences provided herein can be isolated using low density lipoprotein receptor-related protein 6 nucleic acid probes and oligonucleotides under stringent hybridization conditions, by screening libraries. Alternatively, expression libraries can be used to clone nucleic acids encoding low density lipoprotein receptor-related protein 6, polymorphic variants, orthologs, and alleles by detecting expressed homologs immunologically with antisera or purified antibodies made against human low density lipoprotein receptor-related protein 6, or portions thereof.

5. Target and Pathway Genes

In addition to expression profile genes, the present invention also provides target genes. "Target gene," as used herein, refers to a differentially expressed expression profile gene whose expression is unique for a particular state, such that the presence or absence of the transcript of a target gene(s) can indicate the state the cell is in. A target gene can be completely unique to a particular state; the presence or absence of the gene is only seen in a particular cell state, or alternatively, cells in all other states express the gene but it is not seen in the first state. For example, genes encoding low density lipoprotein receptor-related protein 6 are expressed at lower levels in cells of the brain, e.g., in the hippocampus or frontal cortex, of human subjects with a prognosis or diagnosis of late-onset Alzheimer disease. Alternatively, target genes can be identified as relevant to a comparison of two states, that is, the state is compared to another particular state or standard to determine the uniqueness of the target gene. Target genes can be used in the diagnostic, prognostic, and compound identification methods described herein.

It should be understood that a target gene for a first state can be an expression profile gene for a second state. The presence or absence of a particular target gene in one state can be diagnostic of the state; the same gene in a different state can be an expression profile gene.

Further, pathway genes are provided herein. "Pathway genes" are defined by the ability of their gene products to interact with expression profile genes. Pathway genes can also exhibit target gene and/or expression profile gene characteristics and can be included as modulators of expression profile genes as further described below.

The present invention includes the products of such expression profile, target, and pathway genes, as well as antibodies to such gene products. Furthermore, the engineering and use of cell- and animal-based models to understand the prognosis or diagnosis of late-onset Alzheimer disease in human subjects can be accomplished by comparing expression levels of genes encoding low density lipoprotein receptor-related protein 6 in cells of the brain, e.g., in the hippocampus or frontal cortex, can be prognostic or diagnostic of disease states in which analysis of profiles, genes and gene products can contribute.

6. Determining the Degree of Sequence Identity

The invention provides nucleic acids having at least 90%, 91%, 92%, 93%, 94%, 95%, 96%, 97%, 98%, 99% or more sequence identity to nucleic acid sequence for genes encoding low density lipoprotein receptor-related protein 6. The invention provides polypeptides having at least 90%, 91%, 92%, 93%, 94%, 95%, 96%, 97%, 98%, 99% or more sequence identity to polypeptides encoding low density lipoprotein receptor-related protein 6. The sequence identities can be determined by analysis with a sequence comparison algorithm or by a visual inspection. Protein and/or nucleic acid sequence identities (homologies) can be evaluated using any of the variety of sequence comparison algorithms and programs known in the art.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.2.2. or FASTA version 3.0t78 algorithms and the default parameters discussed below can be used.

A "comparison window", as used herein, includes reference to a segment of any one of the number of contiguous positions selected from the group consisting of from 20 to 600, usually about 50 to about 200, more usually about 100 to about 150 in which a sequence can be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman, *Adv. Appl. Math.* 2: 482, 1981, by the homology alignment algorithm of Needleman and Wunsch, *J. Mol. Biol.* 48: 443, 1970, by the search for similarity method of Pearson and Lipman, *Proc. Natl. Acad. Sci. U.S.A.* 85: 2444, 1988, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., (1999 Suppl.), *Current Protocols in Molecular Biology*, Greene Publishing Associates and Wiley Interscience, N.Y., 1987)

A preferred example of an algorithm that is suitable for determining percent sequence identity and sequence similarity is the FASTA algorithm, which is described in Pearson and Lipman, *Proc. Natl. Acad. Sci. U.S.A.* 85: 2444, 1988. See also Pearson, *Methods Enzymol.* 266: 227-258, 1996. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Another preferred example of algorithm that is suitable for determining percent sequence identity and sequence similarity are the BLAST and BLAST 2.0 algorithms, which are described in Altschul et al., *Nuc. Acids Res.* 25: 3389-3402, 1977; and Altschul et al., *J. Mol. Biol.* 215: 403-410, 1990, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy-some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff, *Proc. Natl. Acad. Sci. U.S.A.* 89: 10915, 1989) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. U.S.A.* 90: 5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng and Doolittle, *J. Mol. Evol.* 35: 351-360, 1987. The method used is similar to the method described by Higgins and Sharp, *CABIOS* 5: 151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12: 387-395, 1984.)

Another preferred example of an algorithm that is suitable for multiple DNA and amino acid sequence alignments is the CLUSTALW program (Thompson et al., *Nucl. Acids. Res.* 22: 46734680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, *Proc. Natl. Acad. Sci. U.S.A.* 89: 10915-10919, 1992).

"Sequence identity" refers to a measure of similarity between amino acid or nucleotide sequences, and can be measured using methods known in the art, such as those described below:

"Identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, 91%, 92%, 93%, 94%, 95%, 96%, 97%, 98%, or 99% or more identity over a specified region, when compared and aligned for maximum correspondence over a comparison window, or designated region as measured using one of the following sequence comparison algorithms or by manual alignment and visual inspection.

"Substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

"Homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (for example, nucleic acid sequence for genes encoding low density lipoprotein receptor-related protein 6) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the numbers of contiguous residues. For example, in alternative aspects of the invention, continugous residues ranging anywhere from 20 to the full length of an exemplary polypeptide or nucleic acid sequence of the invention, e.g., polypeptide or nucleic acid sequence for genes encoding low density lipoprotein receptor-related protein 6, are compared to a reference sequence of the same number of contiguous positions after the two sequences are optimally aligned. If the reference sequence has the requisite sequence identity to an exemplary polypeptide or nucleic acid sequence of the invention, e.g., at least 90%, 91%, 92%, 93%, 94%, 95%, 96%, 97%, 98%, 99% or more sequence identity to polypeptide or nucleic acid sequence for genes encoding low density lipoprotein receptor-related protein 6, that sequence is within the scope of the invention.

Motifs which can be detected using the above programs include sequences encoding β-propeller domains, leucine zippers, helix-turn-helix motifs, glycosylation sites, ubiquitination sites, alpha helices, and beta sheets, signal sequences encoding signal peptides which direct the secretion of the encoded proteins, sequences implicated in transcription regulation such as homeoboxes, acidic stretches, enzymatic active sites, substrate binding sites, and enzymatic cleavage sites.

LRP6 14e SNP encode a sequence polymorphism that results in an amino acid substitution (Ile1062→Val). Determining a sequence motif in LRP6 polypeptide, Ile1062 is located within the fourth YWTD (SEQ ID NO.: 17) β-propeller domain of LRP6, following the second YWTD (SEQ ID NO.: 17) tetrarepeat. Most mutations in the LDLR and LRP5 genes that are responsible for different syndromes reside within YWTD (SEQ ID NO.: 17) β-propeller domains which are regions involved in ligand recognition and binding. Ile1062 of LRP6 polypeptide appears to be buried inside the hydrophobic core of the domain, thus helping to maintain circularization of the six-bladed β-propeller structure, rather than participating in ligand presentation.

7. Computer Systems and Computer Program Products

To determine and identify sequence identities, structural homologies, motifs and the like in silico, the sequence of the invention can be stored, recorded, and manipulated on any medium which can be read and accessed by a computer. Accordingly, the invention provides computers, computer systems, computer readable mediums, computer programs products and the like recorded or stored thereon the nucleic acid and polypeptide sequences of the invention. As used herein, the words "recorded" and "stored" refer to a process for storing information on a computer medium. A skilled artisan can readily adopt any known methods for recording information on a computer readable medium to generate manufactures comprising one or more of the nucleic acid and/or polypeptide sequences of the invention.

Another aspect of the invention is a computer readable medium having recorded thereon at least one nucleic acid and/or polypeptide sequence of the invention. Computer readable media include magnetically readable media, optically readable media, electronically readable media and magnetic/optical media. For example, the computer readable media can be a hard disk, a floppy disk, a magnetic tape, CD-ROM, Digital Versatile Disk (DVD), Random Access Memory (RAM), or Read Only Memory (ROM) as well as other types of other media known to those skilled in the art.

As used herein, the terms "computer," "computer program" and "processor" are used in their broadest general contexts and incorporate all such devices.

8. Supports

Supports can be made of a variety of materials, such as glass, silica, plastic, nylon or nitrocellulose. Supports are preferably rigid and have a planar surface. Supports typically have from 1-10,000,000 discrete spatially addressable regions, or cells. Supports having 10-1,000,000 or 100-100,000 or 1000-100,000 cells are common. The density of cells is typically at least 1000, 10,000, 100,000 or 1,000,000 cells within a square centimeter. Typically a single probe per cell. In some supports, all cells are occupied by pooled mixtures of probes. In other supports, some cells are occupied by pooled mixtures of probes, and other cells are occupied, at least to the degree of purity obtainable by synthesis methods, by a single type of polynucleotide. The strategies for probe design described in the present application can be combined with other strategies, such as those described by WO 95/11995, EP 717,113 and WO 97/29212 in the same array.

The location and sequence of each different polynucleotide probe in the array is generally known. Moreover, the large number of different probes can occupy a relatively small area providing a high density array having a probe density of generally greater than about 60, more generally greater than about 100, and most generally greater than about 600, often greater than about 1000, more often greater than about 5,000, most often greater than about 10,000, preferably greater than about 40,000 more preferably greater than about 100,000, and most preferably greater than about 400,000 different polynucleotide probes per $cm^2$. The small surface area of the array (often less than about 10 $cm^2$, preferably less than about 5 $cm^2$ more preferably less than about 2 $cm^2$, and most preferably less than about 1.6 $cm^2$) permits the use of small sample volumes and extremely uniform hybridization conditions.

9. Synthesis of Probe Arrays

Arrays of probes can be synthesized in a step-by-step manner on a support or can be attached in presynthesized form. A preferred method of synthesis is VLSIPS™ (see Fodor et al., Nature 364: 555-556, 1993; McGall et al., U.S. Ser. No. 08/445,332; U.S. Pat. No. 5,143,854; EP 476,014), which entails the use of light to direct the synthesis of polynucleotide probes in high-density, miniaturized arrays. Algorithms for design of masks to reduce the number of synthesis cycles are described by Hubbel et al., U.S. Pat. No. 5,571,639 and U.S. Pat. No. 5,593,839. Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id.; Pease et al., EP 728,520.

After hybridization of control and target samples to an array containing one or more probe sets as described above and optional washing to remove unbound and nonspecifically bound probe, the hybridization intensity for the respective samples is determined for each probe in the array. For fluorescent labels, hybridization intensity can be determined by, for example, a scanning confocal microscope in photon counting mode. Appropriate scanning devices are described by e.g., Trulson et al., U.S. Pat. No. 5,578,832; Stem et al., U.S. Pat. No. 5,631,734 and are available from Affymetrix, Inc., under the GeneChip™ label. Some types of label provide a signal that can be amplified by enzymatic methods (see Broude et al., Proc. Natl. Acad. Sci. U.S.A. 91: 3072-3076, 1994)

10. Design of Arrays

Customized and Generic Arrays. The design of arrays for expression monitoring is generally described, for example, WO 97/27317 and WO 97/10365 (these references are herein incorporated by reference). There are two principal categories of arrays. One type of array detects the presence and/or levels of particular mRNA sequences that are known in advance. In these arrays, polynucleotide probes can be selected to hybridize to particular preselected subsequences of mRNA gene sequence. Such expression monitoring arrays can include a plurality of probes for each mRNA to be detected. For analysis of mRNA nucleic acids, the probes are designed to be complementary to the region of the mRNA that is incorporated into the nucleic acids (i.e., the 3' end). The array can also include one or more control probes.

Generic arrays can include all possible nucleotides of a given length; that is, polynucleotides having sequences corresponding to every permutation of a sequence. Thus since the polynucleotide probes of this invention preferably include up to 4 bases (A, G, C, T) or (A, G, C, U) or derivatives of these bases, an array having all possible nucleotides of length X contains substantially $4.\text{sup}.X$ different nucleic acids (e.g., 16 different nucleic acids for a 2 mer, 64 different nucleic acids for a 3 mer, 65536 different nucleic acids for an 8 mer). Some small number of sequences can be absent from a pool of all possible nucleotides of a particular length due to synthesis problems, and inadvertent cleavage). An array comprising all possible nucleotides of length X refers to an array having substantially all possible nucleotides of length X. All possible nucleotides of length X includes more than 90%, typically more than 95%, preferably more than 98%, more preferably more than 99%, and most preferably more than 99.9% of the possible number of different nucleotides. Generic arrays are particularly useful for comparative hybridization analysis between two mRNA populations or nucleic acids derived therefrom.

Variations. Either customized or generic probe arrays can contain control probes in addition to the probes described above.

Normalization Controls. Normalization controls are typically perfectly complementary to one or more labeled reference polynucleotides that are added to the nucleic acid sample. The signals obtained from the normalization controls after hybridization provide a control for variations in hybridization conditions, label intensity, reading and analyzing efficiency and other factors that can cause the signal of a perfect hybridization to vary between arrays. Signals (e.g., fluorescence intensity) read from all other probes in the array can be divided by the signal (erg., fluorescence intensity) from the control probes thereby normalizing the measurements.

Virtually any probe can serve as a normalization control. However, hybridization efficiency can vary with base composition and probe length. Normalization probes can be selected to reflect the average length of the other probes present in the array, however, they can also be selected to cover a range of lengths. The normalization control(s) can also be selected to reflect the (average) base composition of the other probes in the array. However one or a fewer normalization probes can be used and they can be selected such that they hybridize well (i.e., no secondary structure) and do not match any target-specific probes.

Normalization probes can be localized at any position in the array or at multiple positions throughout the array to control for spatial variation in hybridization efficiently. The normalization controls can be located at the corners or edges of the array as well as in the middle of the array.

Expression Level Controls. Expression level controls can be probes that hybridize specifically with constitutively expressed genes in the biological sample. Expression level controls can be designed to control for the overall health and metabolic activity of a cell. Examination of the covariance of an expression level control with the expression level of the target nucleic acid can indicate whether measured changes or variations in expression level of a gene is due to changes in transcription rate of that gene or to general variations in health of the cell. Thus, for example, when a cell is in poor health or lacking a critical metabolite the expression levels of both an active target gene and a constitutively expressed gene are expected to decrease. The converse can also be true. Thus where the expression levels of both an expression level control and the target gene appear to both decrease or to both increase, the change can be attributed to changes in the metabolic activity of the cell as a whole, not to differential expression of the target gene in question. Conversely, where the expression levels of the target gene and the expression level control do not covary, the variation in the expression level of the target gene can be attributed to differences in regulation of that gene and not to overall variations in the metabolic activity of the cell.

Virtually any constitutively expressed gene can provide a suitable target for expression level controls. Typically expression level control probes can have sequences complementary to subsequences of constitutively expressed genes including, but not limited to the B-actin gene, the transferrin receptor gene, the GAPDH gene, and the like.

Mismatch Controls. Mismatch controls can also be provided for the probes to the target genes, for expression level controls or for normalization controls. Mismatch controls are typically employed in customized arrays containing probes matched to known mRNA species. For example, some such arrays contain a mismatch probe corresponding to each match probe. The mismatch probe is the same as its corresponding match probe except for at least one position of mismatch. A mismatched base is a base selected so that it is not complementary to the corresponding base in the target sequence to which the probe can otherwise specifically hybridize. One or more mismatches are selected such that under appropriate hybridization conditions (e.g. stringent conditions) the test or control probe can be expected to hybridize with its target sequence, but the mismatch probe cannot hybridize (or can hybridize to a significantly lesser extent). Mismatch probes can contain a central mismatch. Thus, for example, where a probe is a 20 mer, a corresponding mismatch probe can have the identical sequence except for a single base mismatch (e.g., substituting a G, a C or a T for an A) at any of positions 6 through 14 (the central mismatch).

In generic (e.g., random, arbitrary, or haphazard) arrays, since the target nucleic acid(s) are unknown perfect match and mismatch probes cannot be a priori determined, designed, or selected. In this instance, the probes can be provided as pairs where each pair of probes differ in one or more preselected nucleotides. Thus, while it is not known a priori which of the probes in the pair is the perfect match, it is known that when one probe specifically hybridizes to a particular target sequence, the other probe of the pair can act as a mismatch control for that target sequence. The perfect match and mismatch probes need not be provided as pairs, but can be provided as larger collections (e.g., 3, 4, 5, or more) of probes that differ from each other in particular preselected nucleotides.

In both customized and generic arrays mismatch probes can provide a control for non-specific binding or cross-hybridization to a nucleic acid in the sample other than the target to which the probe is complementary. Mismatch probes thus can indicate whether a hybridization is specific or not. For example, if the complementary target is present the perfect match probes can be consistently brighter than the mismatch probes. In addition, if all central mismatches are present, the mismatch probes can be used to detect a mutation. Finally, the difference in intensity between the perfect match and the mismatch probe (I(PM)-I(MM)) can provide a good measure of the concentration of the hybridized material.

Sample Preparation, Amplification, and Quantitation Controls. Arrays can also include sample preparation/amplification control probes. These can be probes that are complementary to subsequences of control genes selected because they do not normally occur in the nucleic acids of the particular biological sample being assayed. Suitable sample preparation/amplification control probes can include, for example, probes to bacterial genes (e.g., Bio B) where the sample in question is a biological sample from a eukaryote.

The RNA sample can then be spiked with a known amount of the nucleic acid to which the sample preparation/amplification control probe is directed before processing. Quantification of the hybridization of the sample preparation/amplification control probe can then provide a measure of alteration in the abundance of the nucleic acids caused by processing steps (e.g., PCR, reverse transcription, or in vitro transcription).

Quantitation controls can be similar. Typically they can be combined with the sample nucleic acid(s) in known amounts prior to hybridization. They are useful to provide a quantitation reference and permit determination of a standard curve for quantifying hybridization amounts (concentrations).

11. Methods of Detection

In one method of detection, mRNA or nucleic acid derived therefrom, typically in denatured form, are applied to an array. The component strands of the nucleic acids hybridize to complementary probes, which are identified by detecting label. Optionally, the hybridization signal of matched probes can be compared with that of corresponding mismatched or other control probes. Binding of mismatched probe serves as a measure of background and can be subtracted from binding of matched probes. A significant difference in binding between a perfectly matched probes and a mismatched probes signifies that the nucleic acid to which the matched probes are complementary is present. Binding to the perfectly matched probes is typically at least 1.2, 1.5, 2, 5 or 10 or 20 times higher than binding to the mismatched probes.

In a variation of the above method, nucleic acids are not labeled but are detected by template-directed extension of a probe hybridized to a nucleic acid strand with the nucleic acid strand serving as a template. The probe is extended with a labeled nucleotide, and the position of the label indicates, which probes in the array have been extended. By performing multiple rounds of extension using different bases bearing different labels, it is possible to determine the identity of additional bases in the tag than are determined through complementarity with the probe to which the tag is hybridized. The use of target-dependent extension of probes is described by U.S. Pat. No. 5,547,839.

In a further variation, probes can be extended with inosine. The inosine strand can be labeled. The addition of degenerate bases, such as inosine (it can pair with all other bases), can increase duplex stability between the polynucleotide probe and the denatured single stranded DNA nucleic acids. The addition of 1-6 inosines onto the end of the probes can increase the signal intensity in both hybridization and ligation reactions on a generic ligation array. This can allow for ligations at higher temperatures. The use of degenerate bases is described in WO 97/27317.

Ligation reactions can offer improved discriminate between fully complementary hybrids and those that differ by one or more base pairs, particularly in cases where the mismatch is near the 5' terminus of the polynucleotide probes. Use of a ligation reaction in signal detection increases the stability of the hybrid duplex, improves hybridization specificity (particularly for shorter polynucleotide probes (e.g., 5 to 12-mers), and optionally, provides additional sequence information. Ligation reactions used in signal detection are described in WO 97/27317. Optionally, ligation reactions can be used in conjunction with template-directed extension of probes, either by inosine or other bases.

12. Analysis of Hybridization Patterns

The position of label is detected for each probe in the array using a reader, such as described by U.S. Pat. No. 5,143,854, WO 90/15070, and Trulson et al., supra. For customized arrays, the hybridization pattern can then be analyzed to determine the presence and/or relative amounts or absolute amounts of known mRNA species in samples being analyzed as described in e.g., WO 97/10365. Comparison of the expression patterns of two samples is useful for identifying mRNAs and their corresponding genes that are differentially expressed between the two samples.

The quantitative monitoring of expression levels for large numbers of genes can prove valuable in elucidating gene function, exploring the causes and mechanisms of disease, and for the discovery of potential therapeutic and diagnostic targets. Expression monitoring can be used to monitor the expression (transcription) levels of nucleic acids whose expression is altered in a disease state. For example, late-onset Alzheimer disease can be characterized by the under-expression or overexpression of a particular marker, for example, the underexpression of the gene encoding low density lipoprotein receptor-related protein 6 in the case of determining a prognosis or diagnosis of a human subject with late-onset Alzheimer disease.

Expression monitoring can be used to monitor expression of various genes in response to defined stimuli, such as a drug. This is especially useful in drug research if the end point description is a complex one, not simply asking if one particular gene is overexpressed or underexpressed. Therefore, where a disease state or the mode of action of a drug is not well characterized, the expression monitoring can allow rapid determination of the particularly relevant genes.

In generic arrays, the hybridization pattern is also a measure of the presence and abundance of relative mRNAs in a sample, although it is not immediately known, which probes correspond to which mRNAs in the sample.

However the lack of knowledge regarding the particular genes does not prevent identification of useful therapeutics. For example, if the hybridization pattern on a particular generic array for a healthy cell is known and significantly different from the pattern for a diseased cell, then libraries of compounds can be screened for those that cause the pattern for a diseased cell to become like that for the healthy cell. This provides a detailed measure of the cellular response to a drug.

Generic arrays can also provide a powerful tool for gene discovery and for elucidating mechanisms underlying complex cellular responses to various stimuli. For example, generic arrays can be used for expression fingerprinting. Suppose it is found that the mRNA from a certain cell type displays a distinct overall hybridization pattern that is different under different conditions (e.g., when harboring mutations in particular genes, in a disease state). Then this pattern of expression (an expression fingerprint), if reproducible and clearly differentiable in the different cases can be used as a very detailed diagnostic. It is not required that the pattern be fully interpretable, but just that it is specific for a particular cell state (and preferably of diagnostic and/or prognostic relevance).

Both customized and generic arrays can be used in drug safety studies. For example, if one is making a new antibiotic, then it should not significantly affect the expression profile for mammalian cells. The hybridization pattern can be used as a detailed measure of the effect of a drug on cells, for example, as a toxicological screen.

The sequence information provided by the hybridization pattern of a generic array can be used to identify genes encoding mRNAs hybridized to an array. Such methods can be performed using DNA nucleic acids of the invention as the target nucleic acids described in WO 97/27317. DNA nucleic acids can be denatured and then hybridized to the complementary regions of the probes, using standard conditions described in WO 97/27317. The hybridization pattern indicates which probes are complementary to nucleic acid strands in the sample. Comparison of the hybridization pattern of two samples indicates which probes hybridize to nucleic acid strands that derive from mRNAs that are differentially expressed between the two samples. These probes are of particular interest, because they contain complementary sequence to mRNA species subject to differential expression. The sequence of such probes is known and can be compared with sequences in databases to determine the identity of the full-length mRNAs subject to differential expression provided that such mRNAs have previously been sequenced. Alternatively, the sequences of probes can be used to design hybridization probes or primers for cloning the differentially expressed mRNAs. The differentially expressed mRNAs are typically cloned from the sample in which the mRNA of interest was expressed at the highest level. In some methods, database comparisons or cloning is facilitated by provision of additional sequence information beyond that inferable from probe sequence by template dependent extension as described above.

13. Diagnostic Methods

Diagnosis or prognosis of late-onset Alzheimer disease. The invention provides a variety of methods for the diagnosis or prognosis of late-onset Alzheimer disease. In particular, A method of detecting an increased susceptibility to late onset Alzheimer disease in an individual comprising analyzing a DNA sample from the individual for the presence of at least one single nucleotide polymorphism of a low-density lipo-protein receptor related protein 6 gene sequence, wherein the presence of the at least one single nucleotide polymorphism is indicative of an increased susceptibility to late onset Alzheimer disease. In some methods, the at least one single nucleotide polymorphism is a lrp6-14e (rs2302685; A to G) polymorphism of SEQ ID NO:1. In some methods, the at least one single nucleotide polymorphism is a polymorphism corresponding to a lrp6-14e (Ile1062 to Val) of SEQ ID NO:2. In some methods, the at least one single nucleotide polymorphism is a lrp6-18e (rs1012672; C to T) polymorphism of SEQ ID NO:3. It is to be understood that "diagnosis or prognosis of late-onset Alzheimer disease" does not necessarily mean that the subject will develop late-onset Alzheimer disease but rather that the subject is, in a statistical sense, more likely to develop late-onset Alzheimer disease than an average member of the population. As used herein, "diagnosis or prognosis for late-onset Alzheimer disease" can exist if the subject has one or more genetic determinants (e.g., polymorphic variants or alleles) that can, either alone or in combination with one or more other genetic determinants, contribute to an increased risk of developing late-onset Alzheimer disease in some or all subjects. Ascertaining whether the subject has any such genetic determinants (i.e., genetic determinants that can increase the risk of developing late-onset Alzheimer disease in the appropriate genetic background) is included in the concept of diagnosing susceptibility to late-onset Alzheimer disease, as used herein. Such determination is useful, for example, for purposes of genetic counseling. Thus providing diagnostic information regarding late-onset Alzheimer disease includes providing information useful in genetic counseling, and the provision of such information is encompassed herein.

The sample itself will typically consist of cells (e.g., cells of the hippocampus), tissue, and the like, removed from the subject. The subject can be an adult, child, fetus, or embryo. According to certain embodiments of the invention the sample is obtained prenatally, either from the fetus or embryo or from the mother (e.g., from fetal or embryonic cells in that enter the maternal circulation). The sample can be further processed before the detecting step. For example, DNA in the cell or tissue sample can be separated from other components of the sample, can be amplified, and the like. All samples obtained from a subject, including those subjected to any sort of further processing, are considered to be obtained from the subject.

In general, if the polymorphism is located in a gene, it can be located in a noncoding or coding region of the gene. If located in a coding region the polymorphism can, but frequently will not, result in an amino acid alteration. Such alteration can or can not have an effect on the function or activity of the encoded polypeptide. If the polymorphism is linked to, but not located within, a gene, it is preferred that the polymorphism is closely linked to the gene. For example, it is preferred that the recombination frequency between the polymorphism and the gene is less than approximately 20%, preferably less than approximately 10%, less than approximately 5%, less than approximately 1%, or still less.

According to certain preferred embodiments of any of the inventive methods described above, the gene can be coincident with a mapped or identified locus for late-onset Alzheimer disease, e.g., genes encoding low density lipoprotein receptor-related protein. For example, according to various embodiments of the invention the gene can encode any of the molecules listed in the tables as shown herein. In a particular embodiment of the invention, discussed further below, the preferred genes encode the genes as set forth in SEQ ID NOs 1, 2, or 3. In a further particular embodiment, the following gene alleles from SEQ ID NOs 1, 2, or 3 include, but are not limited to wherein the at least one single nucleotide polymorphism is a lrp6-14e (rs2302685; A to G) polymorphism of SEQ ID NO:1, at least one single nucleotide polymorphism corresponding to a lrp6-14e (Ile1062 to Val) of SEQ ID NO:2, or at least one single nucleotide polymorphism is a lrp6-18e (rs1012672; C to T) polymorphism of SEQ ID NO:3. The inventive methods also encompass genes coincident with late-onset Alzheimer disease susceptibility loci that have yet to be mapped or identified. By "coincident with" is meant either that the gene or a portion thereof falls within the identified chromosomal location or is located in close proximity to that location. In general, the resolution of studies identifying genetic susceptibility loci can be on the order of tens of centimorgans. According to certain embodiments of the invention "close proximity" refers to within 20 centimorgans of either side of the susceptibility locus, more preferably within 10 centimorgans of either side of the susceptibility locus, yet more preferably within 5 centimorgans of either side of the susceptibility locus. In general, susceptibility loci are designated by the chromosomal band positions that they span (e.g., 8p21 refers to chromosome 8, arm p, band 21; 8p20-21 refers to chromosome 8, arm p, bands 20-21 inclusive) and can be defined at higher resolution (e.g., 8p21.1). In general, the terms "coincident with" and "close proximity" can be interpreted in light of the knowledge of one of ordinary skill in the art.

Methods and reagents for identification and detection of polymorphisms. In general, polymorphisms of use in the practice of the invention can be initially identified using any of a number of methods well known in the art. For example, numerous polymorphisms are known to exist and are available in public databases, which can be searched as described. Alternately, polymorphisms can be identified by sequencing either genomic DNA or cDNA in the region in which it is desired to find a polymorphism. According to one approach, primers are designed to amplify such a region, and DNA from a subject suffering from late-onset Alzheimer disease is obtained and amplified. The DNA is sequenced, and the sequence (referred to as a "subject sequence") is compared with a reference sequence, which is typically taken to represent the "normal" or "wild type" sequence. Such a sequence can be, for example, the human draft genome sequence, publicly available in various databases, or a sequence deposited in a database such as GenBank. In general, if sequencing reveals a difference between the sequenced region and the reference sequence, a polymorphism has been identified. Note that this analysis does not necessarily presuppose that either the subject sequence or the reference sequence is the "normal", most common, or wild type sequence. It is the fact that a difference in nucleotide sequence is identified at a particular site that determines that a polymorphism exists at that site. In most instances, particularly in the case of SNPs, only two polymorphic variants will exist at any location. However, in the case of SNPs, up to four variants can exist since there are four naturally occurring nucleotides in DNA. Other polymorphisms such as insertions can have more than four alleles.

Once a polymorphic site is identified, any of a variety of methods can be employed to detect the existence of any particular polymorphic variant in a subject. In general, a subject can have either the reference sequence or an alternate sequence at the site. The phrase "detecting a polymorphism" or "detecting a polymorphic variant" as used herein generally refers to determining which of two or more polymorphic variants exists at a polymorphic site, although "detecting a polymorphism" can also refer to the process of initially determining that a polymorphic site exists in a population. The meaning to be given to these phrases will be clear from the context as interpreted in light of the knowledge of one of ordinary skill in the art. For purposes of description, if a subject has any sequence other than a defined reference sequence (e.g. the sequence present in the human draft genome) at a polymorphic site, the subject can be said to exhibit the polymorphism. In general, for a given polymorphism, any individual will exhibit either one or two possible variants at the polymorphic site (one on each chromosome). (This can, however, not be the case if the individual exhibits one more chromosomal abnormalities such as deletions.)

Detection of a polymorphism or polymorphic variant in a subject (genotyping) can be performed by sequencing, similarly to the manner in which the existence of a polymorphism is initially established as described above. However, once the existence of a polymorphism is established a variety of more efficient methods can be employed. Many such methods are based on the design of oligonucleotide probes or primers that facilitate distinguishing between two or more polymorphic variants.

"Probes" or "primers", as used herein, typically refers to oligonucleotides that hybridize in a base-specific manner to a complementary nucleic acid molecule as described herein. Such probes and primers include polypeptide nucleic acids, as described in Nielsen et al., *Science* 254: 1497-1500, 1991. "primer" in particular generally refers to a single-stranded oligonucleotide that can act as a point of initiation of template-directed DNA synthesis using methods such as PCR (polymerase chain reaction), LCR (ligase chain reaction), and the like. Typically, a probe or primer will comprise a region of nucleotide sequence that hybridizes to at least about 8, more often at least about 10 to 15, typically about 20-25, and frequently about 40, 50 or 75, consecutive nucleotides of a nucleic acid molecule. In certain embodiments of the invention, a probe or primer comprises 100 or fewer nucleotides, preferably from 6 to 50 nucleotides, preferably from 12 to 30 nucleotides. In certain embodiments of the invention, the probe or primer is at least 70% identical to the contiguous nucleotide sequence or to the complement of the contiguous nucleotide sequence, preferably at least 80% identical, more preferably at least 90% identical, even more preferably at least 95% identical, or having an even higher degree of identity. In certain embodiments of the invention a preferred probe or primer is capable of selectively hybridizing to a target contiguous nucleotide sequence or to the complement of the contiguous nucleotide sequence. According to certain embodiments of the invention a probe or primer further comprises a label, for example by incorporating a radioisotope, fluorescent compound, enzyme, or enzyme co-factor.

Oligonucleotides that exhibit differential or selective binding to polymorphic sites can readily be designed by one of ordinary skill in the art. For example, an oligonucleotide that is perfectly complementary to a sequence that encompasses a polymorphic site (i.e., a sequence that includes the polymorphic site within it or at one or the other end) will generally hybridize preferentially to a nucleic acid comprising that sequence as opposed to a nucleic acid comprising an alternate polymorphic variant.

In order to detect polymorphisms and/or polymorphic variants, it will frequently be desirable to amplify a portion of DNA encompassing the polymorphic site. Such regions can be amplified and isolated by PCR using oligonucleotide primers designed based on genomic and/or cDNA sequences that flank the site. See e.g., PCR Primer: A Laboratory Manual, Dieffenbach, C. W. and Dveksler, G. S. (eds.); PCR Basics: From Background to Bench, Springer Verlag, 2000; McPherson et al; Mattila et al., *Nucleic Acids Res.* 19: 4967, 1991; Eckert et al., *PCR Methods and Applications* 1: 17, 1991; PCR (eds. McPherson et al., IRL Press, Oxford); and U.S. Pat. No. 4,683,202. Other amplification methods that can be employed include the ligase chain reaction (LCR) (Wu and Wallace, Genomics 4: 560, 1989; Landegren et al., *Science* 241: 1077, 1988) transcription amplification (Kwoh et al., *Proc. Natl. Acad. Sci. USA* 86: 1173, 1989), self-sustained sequence replication (Guatelli et al., *Proc. Nat. Acad. Sci. USA* 87: 1874, 1990), and nucleic acid based sequence amplification (NASBA). Guidelines for selecting primers for PCR amplification are well known in the art. See, e.g., McPherson et al., PCR 2000, cited supra. A variety of computer programs for designing primers are available, e.g., "Oligo" (National Biosciences, Inc, Plymouth Minn.), MacVector (Kodak/IBI), and the GCG suite of sequence analysis programs (Genetics Computer Group, Madison, Wis. 53711)

According to certain methods for diagnosing late-onset Alzheimer disease or susceptibility to late-onset Alzheimer disease, hybridization methods, such as Southern analysis, Northern analysis, or in situ hybridizations, can be used (see Ausubel et al., supra). For example, a sample (e.g., a sample comprising genomic DNA, RNA, or cDNA), is obtained from a subject suspected of being susceptible to or having Alzheimer disease, e.g., late-onset Alzheimer disease. The DNA, RNA, or cDNA sample is then examined to determine whether a polymorphic variant in a coding or noncoding portion of a gene set forth in Table 1, or a polymorphic variant in a genomic region linked to a coding or noncoding portion of a gene encoding as set forth in Table 1 is present. The presence of the polymorphic variant can be indicated by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant, e.g., a polymorphic variant indicative of susceptibility to late-onset Alzheimer disease.

In order to diagnose susceptibility to late-onset Alzheimer disease, a hybridization sample is formed by contacting the sample with at least one nucleic acid probe. The probe is typically a nucleic acid probe (which can be labeled, e.g., with a radioactive, fluorescent, or enzymatic label or tag) capable of hybridizing to mRNA, genomic DNA, and/or cDNA sequences encompassing detecting a polymorphic variant in a coding or noncoding portion of a gene encoding low density lipoprotein receptor-related protein 6, or a polymorphic variant in a genomic region linked to a coding or noncoding portion of a gene wherein the gene has at least one single nucleotide polymorphism including, but not limited to, a polymorphism corresponding to a lrp6-14e (Ile1062 to Val) of SEQ ID NO:2. The nucleic acid probe can be, for example, a full-length nucleic acid molecule, or a portion thereof, such as an oligonucleotide of at least 15, 30, 50, 100, 250 or 500 nucleotides in length and sufficient to specifically hybridize under stringent conditions to appropriate mRNA, cDNA, or genomic DNA.

The hybridization sample is maintained under conditions selected to allow specific hybridization of the nucleic acid probe to a region encompassing the polymorphic site. Specific hybridization can be performed under high stringency conditions or moderate stringency conditions, for example, as described above. In a particularly preferred embodiment, the hybridization conditions for specific hybridization are high stringency. In general, the probe can be perfectly complementary to the region to which it hybridizes, i.e., perfectly complementary to a region encompassing the polymorphic site when the site contains any particular polymorphic sequence. Multiple nucleic acid probes (e.g., multiple probes differing only at the polymorphic site, or multiple probes designed to detect polymorphic variants at multiple polymorphic sites) can be used concurrently in this method. Specific hybridization of any one of the nucleic acid probes is indicative of a polymorphic variant in a genomic region linked to a coding or noncoding portion of low density lipoprotein receptor-related protein 6 or fragment thereof, or detecting a polymorphic variant or a polymorphism in a genomic region linked to such a gene, wherein the at least one single nucleotide polymorphism is, for example, a lrp6-14e (rs2302685; A to G) polymorphism of SEQ ID NO: 1, a lrp6-14e (Ile1062 to Val) of SEQ ID NO:2, or a lrp6-18e (rs1012672; C to T) polymorphism of SEQ ID NO:3, and is thus diagnostic of susceptibility to late-onset Alzheimer disease.

Northern analysis can be performed using similar nucleic acid probes in order to detect a polymorphic variant or a polymorphism in a coding or noncoding portion of a gene encoding low density lipoprotein receptor-related protein 6, or detecting a polymorphic variant or a polymorphism in a genomic region linked to such a gene, for example, wherein the at least one single nucleotide polymorphism is, for example, a lrp6-14e (rs2302685; A to G) polymorphism of SEQ ID NO:1, a lrp6-14e (Ile1062 to Val) of SEQ ID NO:2, or a lrp6-18e (rs1012672; C to T) polymorphism of SEQ ID NO:3. See, e.g., Ausubel et al., supra.

According to certain embodiments of the invention, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, for example, Nielsen et al., 1994, *Bioconjugate Chemistry* 5 American Chemical Society, p. 1 (1994). The PNA probe can be designed to specifically hybridize to a nucleic acid comprising a polymorphic variant conferring susceptibility to or indicative of the presence of late-onset Alzheimer disease.

According to another method, restriction digest analysis can be used to detect the existence of a polymorphic variant or a polymorphism, if alternate polymorphic variants of the polymorphism result in the creation or elimination of a restriction site. A sample containing genomic DNA is obtained from the individual. Polymerase chain reaction (PCR) can be used to amplify a region comprising the polymorphic site, and restriction fragment length polymorphism analysis is conducted (see, e.g., Ausubel et al., supra). The digestion pattern of the relevant DNA fragment indicates the presence or absence of a particular polymorphic variant of the polymorphism and is therefore indicative of the presence or absence of susceptibility to late-onset Alzheimer disease.

Sequence analysis can also be used to detect specific polymorphic variants. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined.

Allele-specific oligonucleotides can also be used to detect the presence of a polymorphic variant, e.g., through the use of dot-blot hybridization of amplified oligonucleotides with allele-specific oligonucleotide (ASO) probes (see, for example, Saiki et al., *Nature* 324: 163-166, 1986). An "allele-specific oligonucleotide" (also referred to herein as an "allele-specific oligonucleotide probe") is typically an oligonucleotide of approximately 10-50 base pairs, preferably approximately 15-30 base pairs, that specifically hybridizes to a nucleic acid region that contains a polymorphism, e.g., a polymorphism associated with a susceptibility to late-onset Alzheimer disease. An allele-specific oligonucleotide probe that is specific for particular a polymorphism can be prepared, using standard methods (see Ausubel et al., supra).

To determine which of multiple polymorphic variants is present in a subject, a sample comprising DNA is obtained from the individual. PCR can be used to amplify a portion encompassing the polymorphic site. DNA containing the amplified portion can be dot-blotted, using standard methods, and the blot contacted with the oligonucleotide probe. The presence of specific hybridization of the probe to the DNA is then detected. Specific hybridization of an allele-specific oligonucleotide probe (specific for a polymorphic variant indicative of susceptibility to late-onset Alzheimer disease) to DNA from the subject is indicative of susceptibility to late-onset Alzheimer disease.

According to another embodiment of the invention, arrays of oligonucleotide probes that are complementary to nucleic acid portions from a subject can be used to identify polymorphisms. Biochips as described herein can be used.

The array typically includes oligonucleotide probes capable of specifically hybridizing to different polymorphic variants. According to the method, a nucleic acid of interest, e.g., a nucleic acid encompassing a polymorphic site, (which is typically amplified) is hybridized with the array and scanned. Hybridization and scanning are generally carried out according to standard methods. See, e.g., Published PCT Application Nos. WO 92/10092 and WO 95/11995, and U.S. Pat. No. 5,424,186. After hybridization and washing, the array is scanned to determine the position on the array to which the nucleic acid hybridizes. The hybridization data obtained from the scan is typically in the form of fluorescence intensities as a function of location on the array.

Arrays can include multiple detection blocks (i.e., multiple groups of probes designed for detection of particular polymorphisms). Such arrays can be used to analyze multiple different polymorphisms. Detection blocks can be grouped within a single array or in multiple, separate arrays so that varying conditions (e.g., conditions optimized for particular polymorphisms) can be used during the hybridization. For example, it can be desirable to provide for the detection of those polymorphisms that fall within G-C rich stretches of a genomic sequence, separately from those falling in A-T rich segments.

Additional description of use of oligonucleotide arrays for detection of polymorphisms can be found, for example, in U.S. Pat. Nos. 5,858,659 and 5,837,832. In addition, to oligonucleotide arrays, cDNA arrays can be used similarly in certain embodiments of the invention.

Other methods of nucleic acid analysis can be used to detect polymorphisms and/or polymorphic variants. Such methods include, e.g., direct manual sequencing (Church and Gilbert, *Proc. Natl. Acad. Sci. USA* 81: 1991-1995, 1988; Sanger et al., *Proc. Natl. Acad. Sci. USA* 74: 5463-5467, 1977; Beavis et al., U.S. Pat. No. 5,288,644); automated fluorescent sequencing; single-stranded conformation polymorphism assays (SSCP); clamped denaturing gel electrophoresis (CDGE); denaturing gradient gel electrophoresis (DGGE) (Sheffield et al., *Proc. Natl. Acad. Sci. USA* 86: 232-236, 1991), mobility shift analysis (Orita et al., *Proc. Natl. Acad. Sci. USA* 86: 2766-2770, 1989), restriction enzyme analysis (Flavell et al., *Cell* 15: 25, 1978; Geever et al., *Proc. Natl. Acad. Sci. USA* 78: 5081, 1981); heteroduplex analysis; chemical mismatch cleavage (CMC) (Cotton et al., *Proc. Natl. Acad. Sci. USA* 85: 4397-4401, 1985; RNase protection assays (Myers et al., *Science* 230: 1242, 1985); use of polypeptides that recognize nucleotide mismatches, e.g., *E. coli* mutS protein; allele-specific PCR.

In certain embodiments of the invention fluorescence polarization template-directed dye-terminator incorporation (FP-TDI) is used to determine which of multiple polymorphic variants of a polymorphism is present in a subject. This method is based on template-directed primer extension and detection by fluorescence polarization. According to this method, amplified genomic DNA containing a polymorphic site is incubated with oligonucleotide primers (designed to hybridize to the DNA template adjacent to the polymorphic site) in the presence of allele-specific dye-labeled dideoxyribonucleoside triphosphates and a commercially available modified Taq DNA polymerase. The primer is extended by the dye-terminator specific for the allele present on the template, increasing 10-fold the molecular weight of the fluorophore. At the end of the reaction, the fluorescence polarization of the two dye-terminators in the reaction mixture are analyzed directly without separation or purification. This homogeneous DNA diagnostic method has been shown to be highly sensitive and specific and is suitable for automated genotyping of large number of samples. (Chen et al., *Genome Research* 9: 492-498, 1999). Note that rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

Real-time pyrophosphate DNA sequencing is yet another approach to detection of polymorphisms and polymorphic variants (Alderborn et al., *Genome Research* 10: 1249-1258, 2000). Additional methods include, for example, PCR amplification in combination with denaturing high performance liquid chromatography (dHPLC) (Underhill et al., *Genome Research* 7: 996-1005, 1997).

In general, it will be of interest to determine the genotype of a subject with respect to both copies of the polymorphic site present in the genome. For example, the complete genotype can be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means above can be used to determine the genotype of a subject with respect to one or both copies of the polymorphism present in the subject's genome.

According to certain embodiments of the invention it is preferable to employ methods that can detect the presence of multiple polymorphic variants (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel can also be performed so as to detect the presence of multiple polymorphic variants (e.g., polymorphic variants at a plurality of polymorphic sites) in parallel or substantially simultaneously according to certain embodiments of the invention.

The invention provides a database comprising a list of polymorphic sequences stored on a computer-readable medium, wherein the polymorphic sequences occur in a coding or noncoding portion of a gene set forth in Table 1 or fragment thereof, or in a genomic region linked to such a gene, or in a genomic region linked to such a gene, and wherein the list is largely or entirely limited to polymorphisms have been identified as useful in performing genetic diagnosis or prognosis of late-onset Alzheimer disease or susceptibility to late-onset Alzheimer disease, or for performing genetic studies of late-onset Alzheimer disease or susceptibility to late-onset Alzheimer disease.

14. Methods and Reagents for Identification of Late-Onset Alzheimer Disease Susceptibility Loci and Functional Mutations A systematic approach is provided to identifying additional late-onset Alzheimer disease susceptibility loci, polymorphisms useful in diagnosis of late-onset Alzheimer disease or susceptibility to late-onset Alzheimer disease, and to identifying functional mutations that cause or contribute to late-onset Alzheimer disease. The invention provides a variety of methods for the diagnosis or prognosis of late-onset Alzheimer disease. In particular, a method of detecting an increased susceptibility to late onset Alzheimer disease in an individual is provided comprising analyzing a DNA sample from the individual for the presence of at least one single nucleotide polymorphism of a low-density lipoprotein receptor related protein 6 gene sequence, wherein the presence of the at least one single nucleotide polymorphism is indicative of an increased susceptibility to late onset Alzheimer disease. In some methods, the at least one single nucleotide polymorphism is a lrp6-14e (rs2302685; A to G) polymorphism of SEQ ID NO:1. In some methods, the at least one single nucleotide polymorphism is a polymorphism corresponding to a lrp6-14e (Ile1062 to Val) of SEQ ID NO:2. In some methods, the at least one single nucleotide polymorphism is a lrp6-18e (rs1012672; C to T) polymorphism of SEQ ID NO:3. If linkage or association exists, the polymorphism is useful in diagnosis or prognosis of late-onset Alzheimer disease or susceptibility to late-onset Alzheimer disease. Such polymorphisms can thus be located in or define late-onset Alzheimer disease susceptibility locus. The set of samples can comprise samples obtained from one or more families affected with Alzheimer disease (e.g., late-onset Alzheimer disease) and can comprise both related and unrelated individuals. In other embodiments, the at least one single nucleotide polymorphism is, for example, a lrp6-14e (rs2302685; A to G) polymorphism of SEQ ID NO:1, a lrp6-14e (Ile1062 to Val) of SEQ ID NO:2, or a lrp6-18e (rs1012672; C to T) polymorphism of SEQ ID NO:3.

The invention further provides a method of screening drug candidates to treat late-onset Alzheimer disease in a mammalian subject comprising: providing a cell or tissue from a patient with late-onset Alzheimer disease; treating the cell or tissue with a compound that increase Wnt/β-catenin signaling, determining at least one single nucleotide polymorphism including, but not limited to, a lrp6-14e (rs2302685; A to G) polymorphism of SEQ ID NO:1, a lrp6-14e (Ile1062 to Val) of SEQ ID NO:2, or a lrp6-18e (rs1012672; C to T) polymorphism of SEQ ID NO:3 in the cell or tissue; adding a drug candidate to the cell; and determining an effect of the drug candidate on an increased Wnt/β-catenin signaling due to gene expression of low density lipoprotein receptor-related protein 6.

The methods can further comprise analyzing expression of the gene in normal subjects and in subjects affected Alzheimer disease, e.g., late-onset Alzheimer disease, which includes examining the mRNA abundance, size, and tissue expression pattern, examining the abundance, size, tissue expression pattern and/or activity of the encoded protein, and the like.

15. Kits

The differentially expressed protein, agonist or antagonist of the present invention or their homologs are useful tools for examining expression and regulation of, for example, the genes as disclosed herein. Reagents that specifically hybridize to nucleic acids encoding differentially expressed proteins of the invention (including probes and primers of the differentially expressed proteins), and reagents that specifically bind to the differentially expressed proteins, e.g., antibodies, are used to examine expression and regulation.

Also within the scope of the invention are kits comprising the compositions (e.g., monoclonal antibodies, human sequence antibodies, human antibodies, multispecific and bispecific molecules, nucleic acid compositions, e.g., antisense oligonucleotides, double stranded RNA oligonucleotides (RNAi), or DNA oligonucleotides (vectors) containing nucleotide sequences encoding for the transcription of shRNA molecules) of the invention and instructions for use. The kit can further contain a least one additional reagent, or one or more additional human antibodies of the invention (e.g., a human antibody having a complementary activity which binds to an epitope in the antigen distinct from the first human antibody).

Nucleic acid assays for the presence of differentially expressed proteins in a sample include numerous techniques are known to those skilled in the art, such as Southern analysis, northern analysis, dot blots, RNase protection, S1 analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4: 230-250, 1986; Haase et al., *Methods in Virology* 7: 189-226, 1984; and NUCLEIC ACID HYBRDIZATION: A PRACTICAL APPROACH (Hames et al., eds. 1987). In addition, a differentially expressed protein can be detected with the various immunoassay techniques described above. The test sample is typically compared to both a positive control (e.g., a sample expressing recombinant differentially expressed protein) and a negative control.

The present invention also provides for kits for screening drug candidates for treatment of late-onset Alzheimer disease. Such kits can be prepared from readily available materials and reagents. For example, such kits can comprise any one or more of the following materials: the differentially expressed proteins, agonists, or antagonists of the present invention, reaction tubes, and instructions for testing the activities of differentially expressed genes. A wide variety of kits and components can be prepared according to the present invention, depending upon the intended user of the kit and the particular needs of the user. For example, the kit can be tailored for in vitro or in vivo assays for measuring the activity of drug candidates for treatment of late-onset Alzheimer disease.

The invention further provides kits comprising probe arrays as described above. The invention further provides oligonucleotide arrays comprising one or more of the inventive probes described above. In particular, the invention provides an oligonucleotide array comprising oligonucleotide probes that are able to detect polymorphic variants of the genes encoding low density lipoprotein receptor-related protein 6, wherein the at least one single nucleotide polymorphism is, for example, a lrp6-14e (rs2302685; A to G) polymorphism of SEQ ID NO:1, a lrp6-14e (Ile1062 to Val) of SEQ ID NO:2, or a lrp6-18e (rs1012672; C to T) polymorphism of SEQ ID NO:3. In a human subject susceptible to late-onset Alzheimer disease, low density lipoprotein receptor-related protein 6 can be expressed at lower levels in cells of the brain, e.g., in the hippocampus or frontal cortex, of human subjects with a prognosis or diagnosis of late-onset Alzheimer disease. Such arrays can be provided in the form of kits for diagnostic and/or research purposes. Kits can include any of the components mentioned above, in addition to further components specific for hybridization and processing of oligonucleotide arrays. Appropriate software (i.e., computer-readable instructions stored on a computer-readable medium) for analyzing the results obtained by scanning the arrays can be provided by the invention. Such software can, for example, provide the user with an indication of the genotype of a sample and/or provide an assessment of the degree of susceptibility of the subject to Alzheimer disease, e.g., late-onset Alzheimer disease. According to certain embodiments of the invention, the kits are manufactured in accordance with good manufacturing practices (GMP) as required for FDA-approved diagnostic kits.

Optional additional components of the kit include, for example, other restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions.

Usually, the kits of the present invention also contain instructions for carrying out the methods.

16. Inhibiting Expression of Polypeptides and Transcripts

The invention further provides for nucleic acids complementary to (e.g., antisense sequences to) the nucleic acid sequences of the invention. Antisense sequences are capable of inhibiting the transport, splicing or transcription of protein-encoding genes, e.g., the low-density lipoprotein receptor related protein 6 polypeptide encoding nucleic acids of the invention. The inhibition can be effected through the targeting of genomic DNA or messenger RNA. The transcription or function of targeted nucleic acid can be inhibited, for example, by hybridization and/or cleavage. One particularly useful set of inhibitors provided by the present invention includes oligonucleotides which are able to either bind gene or message, in either case preventing or inhibiting the production or function of the protein. The association can be through sequence specific hybridization. Another useful class of inhibitors includes oligonucleotides which cause inactivation or cleavage of protein message. The oligonucleotide can have enzyme activity which causes such cleavage, such as ribozymes. The oligonucleotide can be chemically modified or conjugated to an enzyme or composition capable of cleaving the complementary nucleic acid. One can screen a pool of many different such oligonucleotides for those with the desired activity.

General methods of using antisense, ribozyme technology and RNAi technology, to control gene expression, or of gene therapy methods for expression of an exogenous gene in this manner are well known in the art. Each of these methods utilizes a system, such as a vector, encoding either an antisense or ribozyme transcript of a phosphatase polypeptide of the invention. The term "RNAi" stands for RNA interference. This term is understood in the art to encompass technology using RNA molecules that can silence genes. See, for example, McManus, et al. *Nature Reviews Genetics* 3: 737 (2002). In this application, the term "RNAi" encompasses molecules such as short interfering RNA (siRNA), microRNAs (mRNA), small temporal RNA (stRNA). Generally speaking, RNA interference results from the interaction of double-stranded RNA with genes.

17. Anitsense Oligonucleotides

The invention provides antisense oligonucleotides capable of binding the low-density lipoprotein receptor related protein 6 messenger RNA which can inhibit polypeptide activity by targeting mRNA. Strategies for designing antisense oligonucleotides are well described in the scientific and patent literature, and the skilled artisan can design such oligonucleotides using the novel reagents of the invention. For example, gene walking/RNA mapping protocols to screen for effective antisense oligonucleotides are well known in the art, see, e.g., Ho, *Methods Enzymol.* 314: 168-183, 2000 describing an RNA mapping assay, which is based on standard molecular techniques to provide an easy and reliable method for potent antisense sequence selection. See also Smith, *Eur. J. Pharm. Sci.* 11: 191-198, 2000.

Naturally occurring nucleic acids are used as antisense oligonucleotides. The antisense oligonucleotides can be of any length; for example, in alternative aspects, the antisense oligonucleotides are between about 5 to 100, about 10 to 80, about 15 to 60, about 18 to 40. The optimal length can be determined by routine screening. The antisense oligonucleotides can be present at any concentration. The optimal concentration can be determined by routine screening. A wide variety of synthetic, non-naturally occurring nucleotide and nucleic acid analogues are known which can address this potential problem. For example, peptide nucleic acids (PNAs) containing non-ionic backbones, such as N-(2-aminoethyl) glycine units can be used. Antisense oligonucleotides having phosphorothioate linkages can also be used, as described in WO 97/03211; WO 96/39154; Mata, *Toxicol Appl Pharmacol* 144: 189-197, 1997; Agrawal, *Antisense Therapeutics,* 1996. Antisense oligonucleotides having synthetic DNA backbone analogues provided by the invention can also include phosphoro-dithioate, methylphosphonate, phosphoramidate, alkyl phosphotriester, sulfamate, 3'-thioacetal, methylene(methylimino), 3'-N-carbamate, and morpholino carbamate nucleic acids, as described above.

Combinatorial chemistry methodology can be used to create vast numbers of oligonucleotides that can be rapidly screened for specific oligonucleotides that have appropriate binding affinities and specificities toward any target, such as the sense and antisense polypeptides sequences of the invention (see, e.g., Gold, *J. of Biol. Chem.* 270: 13581-13584, 1995).

18. siRNA

"Small interfering RNA" (siRNA) refers to double-stranded RNA molecules from about 10 to about 30 nucleotides long that are named for their ability to specifically interfere with protein expression through RNA interference (RNAi). Preferably, siRNA molecules are 12-28 nucleotides long, more preferably 15-25 nucleotides long, still more. Preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

RNAi is a two-step mechanism (Elbashir et al., *Genes Dev.,* 2: 188-200, 2001). First, long dsRNAs are cleaved by an enzyme known as Dicer in 21-23 ribonucleotide (nt) fragments, called small interfering RNAs (siRNAs). Then, siRNAs associate with a ribonuclease complex (termed RISC for RNA Induced Silencing Complex) which target this complex to complementary mRNAs. RISC then cleaves the targeted mRNAs opposite the complementary siRNA, which makes the mRNA susceptible to other RNA degradation pathways.

siRNAs of the present invention are designed to interact with a target ribonucleotide sequence, meaning they complement a target sequence sufficiently to bind to the target sequence. The present invention also includes siRNA molecules that have been chemically modified to confer increased stability against nuclease degradation, but retain the ability to bind to target nucleic acids that may be present.

19. Inhibitory Ribozymes

The invention provides ribozymes capable of binding message which can inhibit polypeptide activity by targeting mRNA, e.g., inhibition of polypeptides with low-density lipoprotein receptor related protein 6 or Wnt-β-catenin-signaling activity. Strategies for designing ribozymes and selecting the protein-specific antisense sequence for targeting are well described in the scientific and patent literature, and the skilled artisan can design such ribozymes using the novel reagents of the invention.

Ribozymes act by binding to a target RNA through the target RNA binding portion of a ribozyme which is held in close proximity to an enzymatic portion of the RNA that cleaves the target RNA. Thus, the ribozyme recognizes and binds a target RNA through complementary base-pairing, and once bound to the correct site, acts enzymatically to cleave and inactivate the target RNA. Cleavage of a target RNA in such a manner will destroy its ability to direct synthesis of an encoded protein if the cleavage occurs in the coding sequence. After a ribozyme has bound and cleaved its RNA target, it is typically released from that RNA and so can bind and cleave new targets repeatedly.

In some circumstances, the enzymatic nature of a ribozyme can be advantageous over other technologies, such as antisense technology (where a nucleic acid molecule simply binds to a nucleic acid target to block its transcription, translation or association with another molecule) as the effective concentration of ribozyme necessary to effect a therapeutic treatment can be lower than that of an antisense oligonucleotide. This potential advantage reflects the ability of the ribozyme to act enzymatically. Thus, a single ribozyme molecule is able to cleave many molecules of target RNA. In addition, a ribozyme is typically a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme can be greater than that of antisense oligonucleotide binding the same RNA site.

The enzymatic ribozyme RNA molecule can be formed in a hammerhead motif, but can also be formed in the motif of a hairpin, hepatitis delta virus, group I intron or RnaseP-like RNA (in association with an RNA guide sequence). Examples of such hammerhead motifs are described by Rossi, *Aids Research and Human Retroviruses* 8: 183, 1992; hairpin motifs by Hampel, *Biochemistry* 28: 4929, 1989, and Hampel, *Nuc. Acids Res.* 18: 299, 1990; the hepatitis delta virus motif by Perrotta, *Biochemistry* 31: 16, 1992; the RnaseP motif by Guerrier-Takada, *Cell* 35: 849, 1983; and the group I intron by Cech U.S. Pat. No. 4,987,071. The recitation of these specific motifs is not intended to be limiting; those skilled in the art will recognize that an enzymatic RNA molecule of this invention has a specific substrate binding site complementary to one or more of the target gene RNA regions, and has nucleotide sequence within or surrounding that substrate binding site which imparts an RNA cleaving activity to the molecule.

20. Identification of Compounds for Treatment and Prophylaxis of Disease

When identifying bioactive agents that modulate low-density lipoprotein receptor related protein 6 signaling via Wnt/β-catenin pathway, the information can be used in a wide variety of ways. In one method, one of several cellular assays, e.g., Wnt/β-catenin signaling assay, can be used in conjunction with high throughput screening techniques, to allow monitoring for antagonists or agonists of low-density lipoprotein receptor related protein 6 signaling via Wnt/β-catenin pathway after treatment with a candidate agent, Zlokarnik, et al., Science 279: 84-8, 1998; and Heid et al., Genome Res. 6: 986, 1996; each incorporated herein by reference in their entirety. In one method, the candidate agents are added to cells.

"Candidate bioactive agent" or "drug candidate" or grammatical equivalents as used herein describes any molecule, e.g., protein, oligopeptide, small organic molecule, polysaccharide, polynucleotide, to be tested for bioactive agents that are capable of directly or indirectly altering the activity of low-density lipoprotein receptor related protein 6 signaling via Wnt/β-catenin pathway. In one methods, the bioactive agents modulate low-density lipoprotein receptor related protein 6 signaling via Wnt/β-catenin pathway. In a further embodiment of the method, the candidate agents induce an antagonist or agonist effect in a Wnt/β-catenin signaling assay, as further described below. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, e.g., small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, for example, at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. In a further embodiment, candidate agents are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In some embodiments, the candidate bioactive agents are proteins. By "protein" herein is meant at least two covalently attached amino acids, which includes proteins, polypeptides, oligopeptides and peptides. The protein can be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the methods herein. "Amino acid" also includes imino acid residues such as proline and hydroxyproline. The side chains can be in either the (R) or the (S) configuration. In further embodiments, the amino acids are in the (S) or (L)-configuration. If non-naturally occurring side chains are used, non-amino acid substituents can be used, for example to prevent or retard in vivo degradations.

In one method, the candidate bioactive agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening using the methods herein. The libraries can be bacterial, fungal, viral, and mammalian proteins, and human proteins.

In some methods, the candidate bioactive agents are peptides of from about 5 to about 30 amino acids, typically from about 5 to about 20 amino acids, and typically from about 7 to about 15 being. The peptides can be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In some methods, the library can be fully randomized, with no sequence preferences or constants at any position. In other methods, the library can be biased. Some positions within the sequence are either held constant, or are selected from a limited number of possibilities. For example, in some methods, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, or to purines. In other methods, the candidate bioactive agents are nucleic acids, as defined above.

As described above generally for proteins, nucleic acid candidate bioactive agents can be naturally occurring nucleic acids, random nucleic acids, or "biased" random nucleic acids. For example, digests of procaryotic or eucaryotic genomes can be used as is outlined above for proteins.

In some methods, the candidate bioactive agents are organic chemical moieties.

21. Formulation and Administration of Pharmaceutical Compositions

The invention provides pharmaceutical compositions comprising nucleic acids, peptides and polypeptides (including antibodies) of the invention. As discussed above, the nucleic acids, peptides and polypeptides of the invention can be used to inhibit or activate expression of an endogenous low-density lipoprotein receptor related protein 6 polypeptides. Such inhibition in a cell or a non-human animal can generate a screening modality for identifying compounds to treat or ameliorate Alzheimer disease. Administration of a pharmaceutical composition of the invention to a subject is used to generate a toleragenic immunological environment in the subject. This can be used to tolerize the subject to an antigen.

The nucleic acids, peptides and polypeptides of the invention can be combined with a pharmaceutically acceptable carrier (excipient) to form a pharmacological composition. Pharmaceutically acceptable carriers can contain a physiologically acceptable compound that acts to, e.g., stabilize, or increase or decrease the absorption or clearance rates of the pharmaceutical compositions of the invention. Physiologically acceptable compounds can include, e.g., carbohydrates, such as glucose, sucrose, or dextrans, antioxidants, such as ascorbic acid or glutathione, chelating agents, low molecular weight proteins, compositions that reduce the clearance or hydrolysis of the peptides or polypeptides, or excipients or other stabilizers and/or buffers. Detergents can also used to stabilize or to increase or decrease the absorption of the pharmaceutical composition, including liposomal carriers. Pharmaceutically acceptable carriers and formulations for peptides and polypeptide are known to the skilled artisan and are described in detail in the scientific and patent literature, see e.g., the latest edition of Remington's Pharmaceutical Science, Mack Publishing Company, Easton, Pa. ("Remington's").

Other physiologically acceptable compounds include wetting agents, emulsifying agents, dispersing agents or preservatives which are particularly useful for preventing the growth or action of microorganisms. Various preservatives are well known and include, e.g., phenol and ascorbic acid. One skilled in the art would appreciate that the choice of a pharmaceutically acceptable carrier including a physiologically acceptable compound depends, for example, on the route of administration of the peptide or polypeptide of the invention and on its particular physio-chemical characteristics.

In one aspect, a solution of nucleic acids, peptides or polypeptides of the invention are dissolved in a pharmaceutically acceptable carrier, e.g., an aqueous carrier if the composition is water-soluble. Examples of aqueous solutions that can be used in formulations for enteral, parenteral or transmucosal drug delivery include, e.g., water, saline, phosphate buffered saline, Hank's solution, Ringer's solution, dextrose/saline, glucose solutions and the like. The formulations can contain pharmaceutically acceptable auxiliary substances as required to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration. The concentration of peptide in these formulations can vary widely, and will be selected primarily based on fluid volumes, viscosities, body weight and the like in accordance with the particular mode of administration selected and the patient's needs.

Solid formulations can be used for enteral (oral) administration. They can be formulated as, e.g., pills, tablets, powders or capsules. For solid compositions, conventional nontoxic solid carriers can be used which include, e.g., pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10% to 95% of active ingredient (e.g., peptide). A non-solid formulation can also be used for enteral administration. The carrier can be selected from various oils including those of petroleum, animal, vegetable or synthetic origin, e.g., peanut oil, soybean oil, mineral oil, sesame oil, and the like. Suitable pharmaceutical excipients include e.g., starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol.

Nucleic acids, peptides or polypeptides of the invention, when administered orally, can be protected from digestion. This can be accomplished either by complexing the nucleic acid, peptide or polypeptide with a composition to render it resistant to acidic and enzymatic hydrolysis or by packaging the nucleic acid, peptide or polypeptide in an appropriately resistant carrier such as a liposome. Means of protecting compounds from digestion are well known in the art, see, e.g., Fix, Pharm Res. 13: 1760-1764, 1996; Samanen, J. Pharm. Pharmacol. 48: 119-135, 1996; U.S. Pat. No. 5,391,377, describing lipid compositions for oral delivery of therapeutic agents (liposomal delivery is discussed in further detail, infra).

Systemic administration can also be by transmucosal or transdermal means. For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. See, e.g., Sayani, Crit. Rev. Ther. Drug Carrier Syst. 13: 85-184, 1996. For topical, transdermal administration, the agents are formulated into ointments, creams, salves, powders and gels. Transdermal delivery systems can also include, e.g., patches.

The nucleic acids, peptides or polypeptides of the invention can also be administered in sustained delivery or sustained release mechanisms, which can deliver the formulation internally. For example, biodegradeable microspheres or capsules or other biodegradeable polymer configurations capable of sustained delivery of a peptide can be included in the formulations of the invention (see, e.g., Putney, Nat. Biotechnol. 16: 153-157, 1998).

For inhalation, the nucleic acids, peptides or polypeptides of the invention can be delivered using any system known in the art, including dry powder aerosols, liquids delivery systems, air jet nebulizers, propellant systems, and the like. See, e.g., Patton, Biotechniques 16: 141-143, 1998; product and inhalation delivery systems for polypeptide macromolecules by, e.g., Dura Pharmaceuticals (San Diego, Calif.), Aradigm (Hayward, Calif.), Aerogen (Santa Clara, Calif.), Inhale Therapeutic Systems (San Carlos, Calif.), and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

In preparing pharmaceuticals of the present invention, a variety of formulation modifications can be used and manipulated to alter pharmacokinetics and biodistribution. A number of methods for altering pharmacokinetics and biodistribution are known to one of ordinary skill in the art. Examples of such methods include protection of the compositions of the invention in vesicles composed of substances such as proteins, lipids (for example, liposomes, see below), carbohydrates, or synthetic polymers (discussed above). For a general discussion of pharmacokinetics, see, e.g., Remington's, Chapters 37-39.

The nucleic acids, peptides or polypeptides of the invention can be delivered alone or as pharmaceutical compositions by any means known in the art, e.g., systemically, regionally, or locally (e.g., directly into, or directed to, a tumor); by intraarterial, intrathecal (IT), intravenous (IV), parenteral, intrapleural cavity, topical, oral, or local administration, as subcutaneous, intra-tracheal (e.g., by aerosol) or transmucosal (e.g., buccal, bladder, vaginal, uterine, rectal, nasal mucosa). Actual methods for preparing administrable compositions will be known or apparent to those skilled in the art and are described in detail in the scientific and patent literature, see e.g., Remington's. For a "regional effect," e.g., to focus on a specific organ, one mode of administration includes intra-arterial or intrathecal (IT) injections, e.g., to focus on a specific organ, e.g., brain and CNS (see e.g., Gurun, *Anesth Analg.* 85: 317-323, 1997). For example, intra-carotid artery injection if preferred where it is desired to deliver a nucleic acid, peptide or polypeptide of the invention directly to the brain. Parenteral administration is a preferred route of delivery if a high systemic dosage is needed. Actual methods for preparing parenterally administrable compositions will be known or apparent to those skilled in the art and are described in detail, in e.g., Remington's, See also, Bai, *J. Neuroimmunol.* 80: 65-75, 1997; Warren, *J. Neurol. Sci.* 152: 31-38, 1997; Tonegawa, *J. Exp. Med.* 186: 507-515, 1997.

In one aspect, the pharmaceutical formulations comprising nucleic acids, peptides or polypeptides of the invention are incorporated in lipid monolayers or bilayers, e.g., liposomes, see, e.g., U.S. Pat. Nos. 6,110,490; 6,096,716; 5,283,185; 5,279,833. The invention also provides formulations in which water soluble nucleic acids, peptides or polypeptides of the invention have been attached to the surface of the monolayer or bilayer. For example, peptides can be attached to hydrazide-PEG-(distearoylphosphatidyl) ethanolamine-containing liposomes (see, e.g., Zalipsky, *Bioconjug. Chem.* 6: 705-708, 1995). Liposomes or any form of lipid membrane, such as planar lipid membranes or the cell membrane of an intact cell, e.g., a red blood cell, can be used. Liposomal formulations can be by any means, including administration intravenously, transdermally (see, e.g., Vutla, *J. Pharm. Sci.* 85: 5-8, 1996), transmucosally, or orally. The invention also provides pharmaceutical preparations in which the nucleic acid, peptides and/or polypeptides of the invention are incorporated within micelles and/or liposomes (see, e.g., Suntres, *J. Pharm. Pharmacol.* 46: 23-28, 1994; Woodle, *Pharm. Res.* 9: 260-265, 1992). Liposomes and liposomal formulations can be prepared according to standard methods and are also well known in the art, see, e.g., Remington's; Akimaru, *Cytokines Mol. Ther.* 1: 197-210, 1995; Alving, *Immunol. Rev.* 145: 5-31, 1995; Szoka, *Ann. Rev. Biophys. Bioeng.* 9: 467, 1980; U.S. Pat. Nos. 4,235,871, 4,501,728 and 4,837,028.

The pharmaceutical compositions are generally formulated as sterile, substantially isotonic and in full compliance with all Good Manufacturing Practice (GMP) regulations of the U.S. Food and Drug Administration.

22. Treatment Regimens: Pharmacokinetics

The pharmaceutical compositions of the invention can be administered in a variety of unit dosage forms depending upon the method of administration. Dosages for typical nucleic acid, peptide and polypeptide pharmaceutical compositions are well known to those of skill in the art. Such dosages are typically advisorial in nature and are adjusted depending on the particular therapeutic context, patient tolerance, etc. The amount of nucleic acid, peptide or polypeptide adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

In therapeutic applications, compositions are administered to a patient suffering from Alzheimer disease in an amount sufficient to at least partially arrest the condition or a disease and/or its complications. For example, in one aspect, a soluble peptide pharmaceutical composition dosage for intravenous (IV) administration would be about 0.01 mg/hr to about 1.0 mg/hr administered over several hours (typically 1, 3, or 6 hours), which can be repeated for weeks with intermittent cycles. Considerably higher dosages (e.g., ranging up to about 10 mg/ml) can be used, particularly when the drug is administered to a secluded site and not into the blood stream, such as into a body cavity or into a lumen of an organ, e.g., the cerebrospinal fluid (CSF).

The invention will be further described with reference to the following examples; however, it is to be understood that the invention is not limited to such examples.

EXEMPLARY EMBODIMENTS
Example 1

Association of Low Density Lipoprotein Receptor Related Protein 6 with Late Onset Alzheimer Disease Genome-wide linkage studies have defined a broad susceptibility region for late-onset Alzheimer disease (AD) on chromosome 12, which contains the low density lipoprotein receptor related protein 6 (LRP6), a co-receptor for Wnt signalling. Pericak-Vance et al., *JAMA* 278: 1237-41, 1997; Rogaeva et al., *JAMA* 280: 614-8, 1998; Wu et al., *JAMA* 280: 619-22, 1998; Kehoe et al., *Hum Mol Genet* 8: 237-45, 1999; Scott et al., *Am J Hum Genet* 66: 922-32, 2000; Myers et al., *Am J Med Genet* 114: 235-44, 2002; Mayeux et al., *Am J Hum Genet* 70: 237-43, 2002; Brown et al., *Biochem Biophys Res Commun* 248: 879-88, 1998; Pinson et al., *Nature* 407: 535-8, 2000; Tamai et al., *Nature* 407: 530-5, 2000; Wehrli et al., *Nature* 407: 527-30, 2000. The present study discovered in a large family-based series ascertained by the NIMH-NIA Genetics Initiative that LRP6 single nucleotide polymorphisms (SNPs) 14e (Ile1062→Val) and 18e (Cys1270→Cys) are significantly associated to late-onset AD in the Apolipoprotein E-ε4 (APOE-ε4) negative stratum. Functional analyses revealed that LRP6 14e alleles display differential Wnt signalling activity and that LRP6 is normally expressed in adult human hippocampus. The present data supports the notion that altered Wnt signalling function is central to the onset of this neurodegenerative disease.

Inheritance of the Apolipoprotein E-ε4 (APOE-ε4) allele is a risk factor for Alzheimer disease (AD). Corder et al., *Science* 261: 921-3, 1993. Nevertheless, epidemiological studies estimate that 42-68% of AD sufferers do not present the APOE-ε4 allele, suggesting that additional genetic or environmental factors could play essential roles in the disease. Warwick Daw et al., *Am J Hum Genet* 66: 196-204, 2000. A fact consistent with this observation is that genome-wide screens have identified several regions that show significant linkage to AD, of which the most likely to harbor new risk factors are chromosomes 10 and 12. Pericak-Vance et al., *JAMA* 278: 1237-41, 1997; Rogaeva et al., *JAMA* 280: 614-8, 1998; Wu et al., *JAMA* 280: 619-22, 1998; Kehoe et al., *Hum Mol Genet* 8: 237-45, 1999; Scott et al., *Am J Hum Genet* 66: 922-32, 2000; Myers et al., *Am J Med Genet* 114: 235-44, 2002; Mayeux et al., *Am J Hum Genet* 70: 237-43, 2002; Blacker et al., *Hum Mol Genet* 12: 23-32, 2003. The reported linkage peaks for chromosome 12 show significant association to AD only when samples had been stratified according to APOE carrier status and cluster into two distinct regions (FIG. 1A). One region is located at the p-ter, from ~6-30 cM, in the same vicinity as the α-2-macroglobulin gene (located at ~20 cM) and the low density lipoprotein receptor related protein 6 (LRP6) gene (at ~26 cM). Saunders et al., *Hum Mol Genet* 12: 2765-76, 2003. The other region is pericentromeric, from ~48-68 cM close to the LRP1 gene (~68 cM). It has been proposed that loss of Wnt signalling function may underlie AD, leading to the present examination of whether the LRP6 gene is associated with AD. De Ferrari & Inestrosa, *Brain Res Brain Res Rev* 33: 1-12, 2000; Mudher & Lovestone, *Trends Neurosci* 25: 22-6, 2002; Caricasole et al., *Trends Pharmacol Sci* 24: 233-8, 2003; Moon et al., *Nat Rev Genet* 5: 691-701, 2004.

Initially the present study sought to confirm the existence of single nucleotide polymorphisms (SNPs) in exons 7, 11, 14, 16 and 18 of the LRP6 gene, which have been previously described in the dbSNP database (NCBI) (FIG. 1B). DNA from 18 AD individuals was sequenced, extracted from the affected siblings pairs (ASPs) series coming from the National Institute of Mental Health (NIMH) and the National Cell Repository for Alzheimer Disease, and 11 unrelated individuals. Wu et al., *JAMA* 280: 619-22, 1998; Kehoe et al., *Hum Mol Genet* 8: 237-45, 1999; Myers et al., *Am J Med Genet* 114: 235-44, 2002. It was observed that only the non synonymous coding sequence SNPs in exon 14 (14e, dbSNP id. rs2302685; A→G) and a synonymous SNP in exon 18 (18e, rs1012672; C→T) were polymorphic in the sample and therefore the analysis was continued with LRP6 SNPs 14e and 18e.

Upon genotyping four hundred seventy four families (1372 individuals) corresponding to the full NIMH-NIA ASPs sample, and analysing the data using the Family Based Association Test package FBAT, no significant association was detected in single-locus tests for any of the two LRP6 SNPs (Table 1). Rabinowitz & Laird, *Hum Hered* 50: 211-23, 2000; Lake et al., *Am J Hum Genet* 67: 1515-25, 2000. Given that previous genome-wide reports have shown that the evidence for linkage to chromosome 12 is significant only when the analysis is limited to families lacking an APOE-ε4 allele (FIG. 1a), the ASPs sample subsequently was stratified on the basis of whether both or neither members of an ASP possessed at least one APOE-ε4 allele. Wu et al., *JAMA* 280: 619-22, 1998; Kehoe et al., *Hum Mol Genet* 8: 237-45, 1999; Myers et al., *Am J Med Genet* 114: 235-44, 2002. The ASP sample thus stratified gave 860 individuals corresponding to the APOE-ε4-positive stratum (295 nuclear families; 76.9%) and 259 individuals within the APOE-ε4-negative subgroup (93 nuclear families; 23.1%). Remarkably, FBAT analysis revealed that LRP6 14e was found to be significantly associated in the APOE-ε4-negative stratum (P=0.026; Table 1), while no association was detected in the APOE-ε4-positive stratum. Moreover, FBAT analyses showed that the frequency of the minor allele for 14e (nucleotide G) increased in the ε4-negative stratum, compared to the whole ASP sample or to the ε4-positive stratum and that the Z-statistic score was positive (Z=2.225) indicating that this allele conferred risk/susceptibility for the disease. On the other hand, despite of having 93 nuclear families in the APOE-ε4-negative stratum and due to lack of proper number of "informative families" required by FBAT (a family is informative when it has a non-zero contribution to the FBAT statistic; i.e., families with members that have all the same genotypes for example, are not informative) the statistical software did not yield any reliable results for LRP6 18e in this subgroup. Rabinowitz & Laird, *Hum Hered* 50: 211-23, 2000; Lake et al., *Am J Hum Genet* 67: 1515-25, 2000.

FIG. 1 shows a relationship between late onset Alzheimer disease and chromosome 12.a, Summary of reported genome-wide linkage regions according to APOE carrier status and location of LRP6/BCL-G locus relative to candidate genes showing association to AD. b, Diagram of exon-intron boundaries of LRP6/BCL-G genes and chromosomal position of SNPs (arrows) analyzed in this study.

TABLE 1

Association of LRP6 SNPs 14e and 18e in the NIMH ASP sample.

| | Whole sample | | | APOE-ε4-positive | | | APOE-ε4-negative | | |
|---|---|---|---|---|---|---|---|---|---|
| Stat | Frequency | Families | P value | Frequency | Families | P value | Frequency | Families | P value |
| Single SNPs | | | | | | | | | |
| 14e | 0.204 | 80 | 0.68 | 0.210 | 52 | 0.24 | 0.217 | 14 | 0.03 |
| 18e | 0.090 | 51 | 0.26 | 0.086 | 33 | 0.71 | 0.085 | 7 | — |
| Haplotypes | | | | | | | | | |
| AC | 0.754 | 100 | 0.72 | 0.747 | 65 | 0.42 | 0.731 | 17 | 0.003 |
| GC | 0.179 | 81 | 0.35 | 0.189 | 53 | 0.20 | 0.200 | 16 | 0.09 |
| AT | 0.670 | 53 | 0.10 | 0.064 | 34 | 0.61 | 0.069 | 7.7 | — |
| GT | — | — | — | — | — | — | 0.001 | 0.3 | — |
| Multi-haplotype | $\chi^2$ | P value | | $\chi^2$ | P value | | $\chi^2$ | P value | |
| | 2.99 | 0.22 | | 1.66 | 0.44 | | 9.42 | 0.009 | |

Results of FBAT Single-Locus and HBAT Haplotype (univariate) and Multihaplotype (Global) tests for LRP6 SNPs 14e and 18e.
Frequency of minor alleles: 14e (G); 18e (T).
Families: Number of informative pedigrees.
P value: FBAT or HBAT nominal P value.

The use of haplotypes in family-based association testing is a robust and powerful method especially when the informativeness of individual markers is low. Horvath et al., *Genet Epidemiol* 26: 61-9, 2004. Therefore the haplotype contribution of LRP6 14e and 18e SNPs was examinef with the aid of the program haplotype-FBAT (HBAT). Horvath et al., *Genet Epidemiol* 26: 61-9, 2004. Interestingly, LRP6 haplotype 14eA/18eC was found to be associated with a highly significant P value (P=0.003) within the APOE-ε4-negative stratum (Table 1). In agreement to what was observed before, the Z-statistic for haplotype 14eA/18eC was negative (Z=−2.964) indicating a protective effect for this haplotype in the AD ASP sample (Table 1). Furthermore, Global (multi-haplotype) test between 14e and 18e showed that both SNPs were highly associated to AD only in the APOE-ε4-negative stratum (P=0.009) (Table 1).

Although both LRP6 14e and 18e SNPs are coding sequence polymorphisms, only 14e results in an amino acid substitution (Ile1062→Val). ClustalW alignment of homologous protein sequences of Wnt co-receptors LRP6 and LRP5 from human, mouse and Arrow, its ortholog in *Drosophila*, shows that the LRP6 residue Ile1062 is highly conserved during evolution (FIG. 2A). Likewise LRP6 Ile1062 is also conserved in the human and mouse low density lipoprotein Receptor (LDLR) (FIG. 2A), which constitutes the signature for this family of transmembrane proteins, suggesting that this residue may be important for proper protein function.

Structurally, Ile1062 is located within the fourth YWTD (SEQ ID NO.: 17) β-propeller domain of LRP6, following the second YWTD (SEQ ID NO.: 17) tetrarepeat (FIG. 3a). Most mutations in the LDLR and LRP5 genes that are responsible for different syndromes reside within YWTD (SEQ ID NO.: 17) β-propeller domains (rev, in Jeon et al., *Nat Struct Biol* 8: 499-504, 2001; He et al., *Development* 131: 1663-77, 2004), which are regions involved in ligand recognition and binding. Ile1062 appears to be buried inside the hydrophobic core of the domain (FIG. 3b), thus helping to maintain circularization of the six-bladed β-propeller structure, rather than participating in ligand presentation. Jeon et al., *Nat Struct Biol* 8: 499-504, 2001.

To test whether the LRP14eV SNP displayed altered activation of the Wnt/β-catenin pathway, HEK293T/sTF cells (HEK293T cells were transfected to stably express a β-catenin-responsive luciferase reporter) with cDNAs encoding the 14eI and 14eV alleles. Some of the cells were treated for 48 h with conditioned media (CM) containing Wnt3a, then assayed for activation of a β-catenin responsive luciferase reporter. Interestingly, 14eV was less active than 14eI in signaling, either without (FIG. 2b) or with (FIG. 2e) Wnt3a. Similar results were obtained when 293T cells transiently transfected with either the LRP6 alleles or Wnt8B for 24 h and co-cultured for another 24 h before luciferase determination (not shown). Both alleles are expressed at similar levels (FIG. 2c) and accumulate at the plasma membrane similarly when scored by biotinylating surface proteins followed by immunoprecipitation and western blotting (FIG. 2d). In conclusion, LRP6 14eV displays diminished activation of the Wnt/β-catenin signaling pathway.

Figure 2:
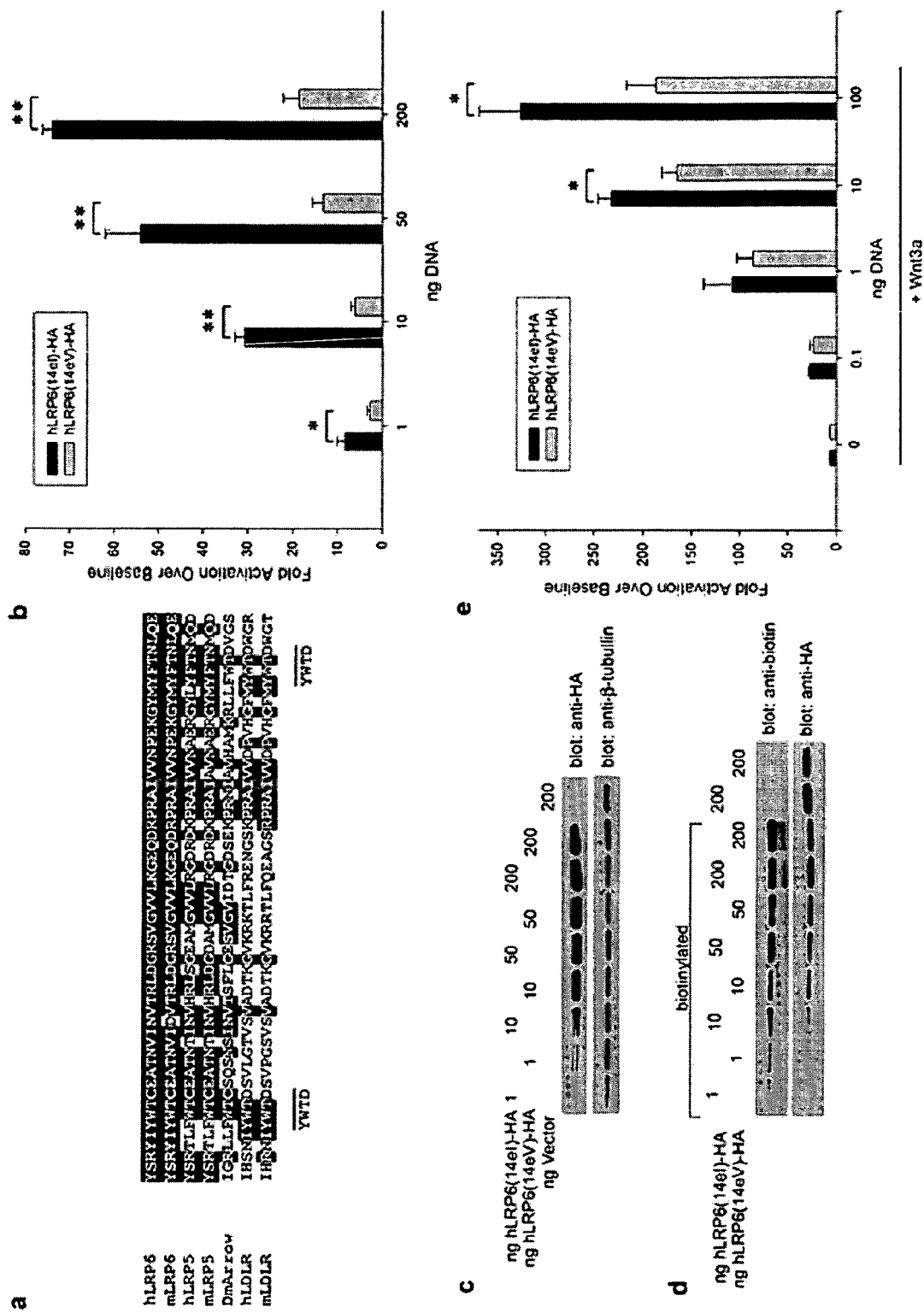
FIGS. 2a (SEQ ID NOs: 10, 11, 12, 13, 14, 15, 16, 17), 2b, 2c, 2d, and 2e show differential effects of LRP6 alleles 14eI and 14eV on Wnt signal transduction.

FIG. 2 shows differential effects of LRP6 alleles 14eI and 14eV on Wnt signal transduction. a. ClustalW multiple sequence alignment showing LRP6 Ile1062 as a highly conserved amino-acid among LDLR-family members in humans (h), mice (m) and *Drosophila melanogaster* (Dm). b. HEK293T/sTF were transfected with increasing DNA doses of HA-tagged hLRP6 allele 14eI or 14eV. Luciferase reporter activity was assessed 48 hours post-transfection. Values represent averages (n=3) of fold activation over control plasmid (pCS2p+). Errors bars represent standard deviation. * denotes P<0.01; ** denotes P<0.001 (Student-t test). c. Representative western blot showing equivalent total expression of each allele at each dose from the whole cell lysates measured in panel b. Blots were probed with anti-HA antibody, stripped, and reblotted with an anti-β-tubullin antibody for normalization. d. Representative western blot showing equivalent plasma membrane expression of each allele from cell lysates measured in panel b. Plasma membrane proteins were biotinylated with sulfo-NHS-biotin and the HA-tagged LRP6 alleles were immunoprecipitated with anti-HA antibody. Blots were probed with anti-biotin to reveal plasma membrane expression, stripped, and reprobed with anti-HA to show total expression of HA-tagged LRP6. e. HEK293T/sTF cells transfected with increasing DNA doses of empty vector, hLRP6 (14eI)-HA, or hLRP6(14eV)-HA were treated with Wnt3a conditioned media diluted 1:5 immediately following transfection. Luciferase reporter activity was assessed 48 hours post-transfection. Data are presented as means ±standard deviations of three separate experiments measured in duplicate. * denotes P<0.01 (Student-t test).

Figure 3:
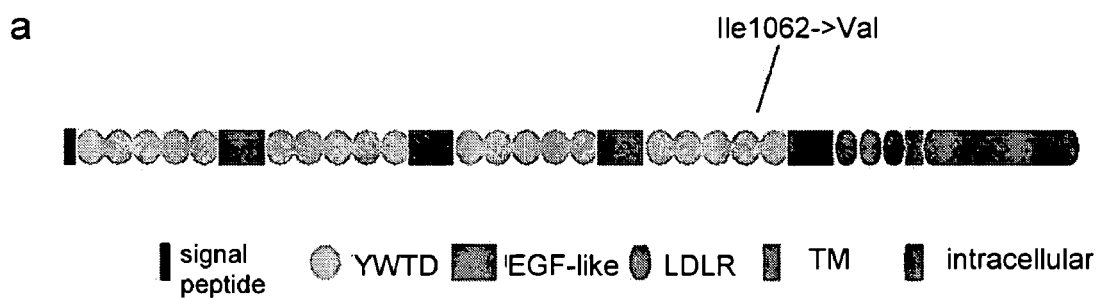
FIGS. 3a and 3b show that LRP6 14e polymorphism is buried within the hydrophobic core of the β-propeller domain.
Figure 3:
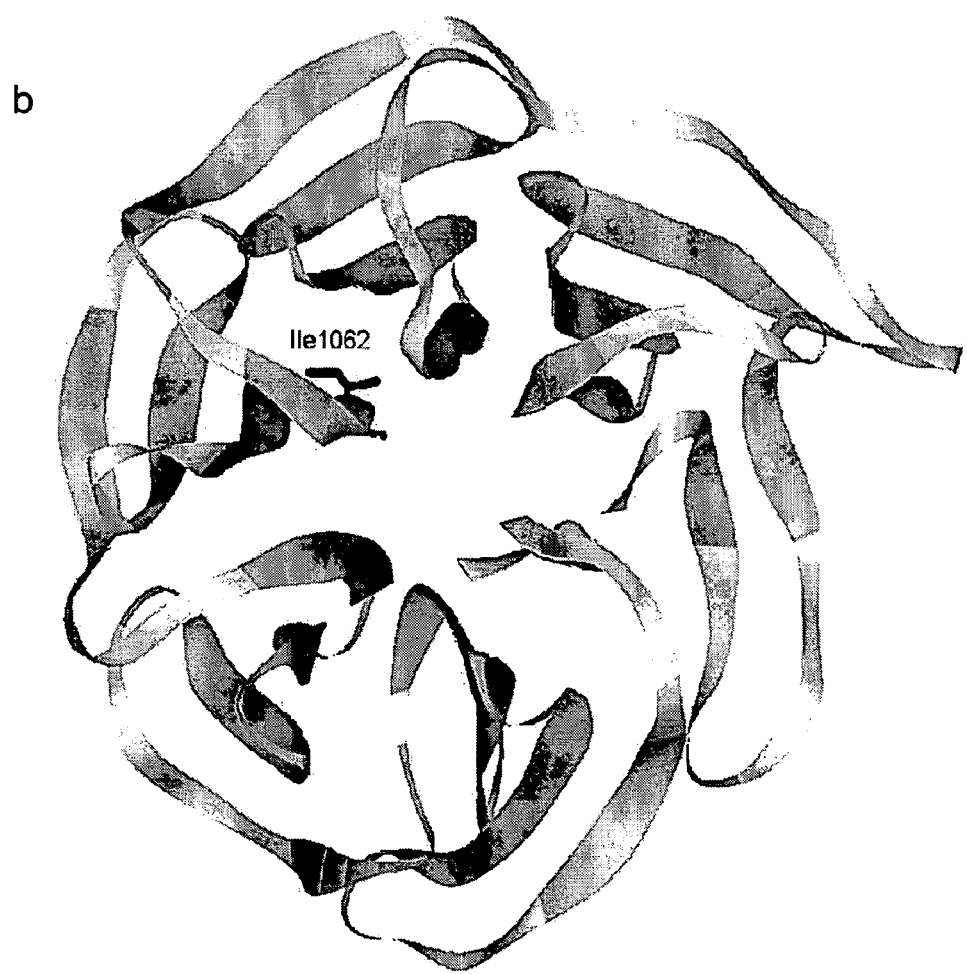

FIG. 3 shows that LRP6 14e polymorphism is buried within the hydrophobic core of the β-propeller domain, a, A schematic of the structure of LRP6. Motifs are identified by their homology to members of the LDLR family. The location of Ile1062 is shown. b, Three dimensional model of the human LRP6 (Modeller 7v7; based on the high resolution structure of the YWTD-EGF (SEQ ID NO.: 17) fragment of the LDLR containing its β-propeller domain (PDB accession code 1IJQ; Jeon et al., 2001).

Wnts are essential molecules in defining the boundaries of the developing human forebrain, most notably the hippocampal formation. Lako et al., *Hum Mol Genet* 7: 813-22, 1998; Abu-Khalil et al., *J Comp Neurol* 474: 276-88, 2004. Nevertheless, the compartmentalisation and physiological function of Wnts in the mature brain, as well as of its complex receptor (i.e., Frizzled and LRP5/6), is still far from being understood. Given that preclinical AD is manifested early in the hippocampal formation, further experiments examined whether LRP5 and/or LRP6 are expressed in the adult human hippocampus. Indeed, by quantitative RT-PCR experiments both transcripts were detected in the adult human hippocampus (FIG. 4), suggesting that the co-receptor for Wnt signalling may be functional in vivo in the mature brain. These results agree well with the observation that Wnt signalling is highly restricted to the hippocampus and the frontal cortex in adult mouse brain. Maretto et al., *Proc Natl Acad Sci USA* 100: 3299-304, 2003.

Figure 4:
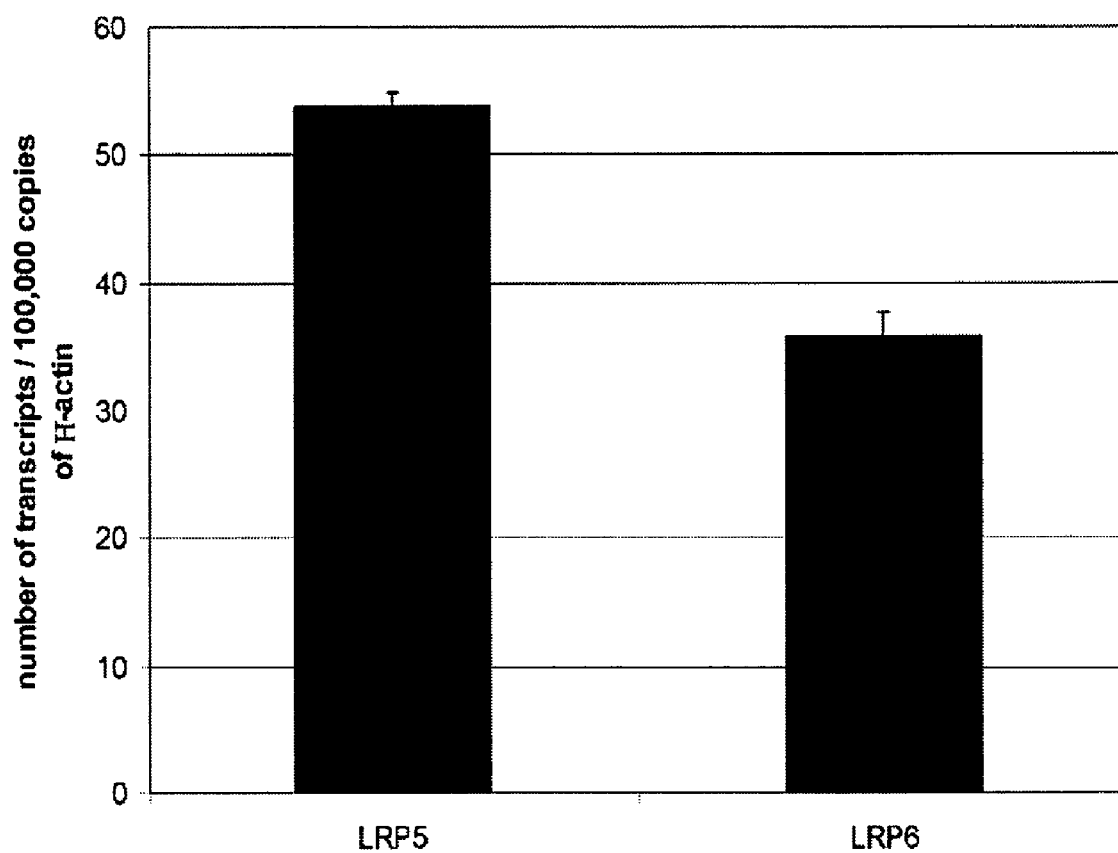
FIG. 4 shows that LRP5 and LRP6 are expressed in normal human hippocampus tissue.

FIG. 4 shows that LRP5 and LRP6 are expressed in normal human hippocampus tissue. Following reverse transcription of hippocampus polyA-mRNA, real-time quantitative PCR for LRP5, LRP6 and β-actin was performed. Quantitative data for LRP5 and LRP6 were normalized to copies of β-actin. The error bars represent the standard error between triplicate real-time PCR quantitations.

The genetic association of the LRP6 gene to late-onset AD observed in this study is strictly dependent on APOE-ε4 carrier status. APOE is a component of several classes of secreted lipoproteins that mediate ligand-receptor presentation/endocytosis through the LDLR family of single transmembrane proteins, including LRP1 (rev. in Li et al., *Mol Neurobiol* 23: 53-67, 2001; Herz, *Neuron* 29: 571-81, 2001). Nonetheless, LRP1 levels decline normally in the aging population and are drastically reduced in AD brains, suggesting that once LRP1 is absent other receptors of this family might become important in modulating APOE effects. Kang et al., *J Clin Invest* 106: 1159-66, 2000. It has been proposed that sustained loss of function of Wnt signalling may underlie the onset and/or development of AD. De Ferrari & Inestrosa, *Brain Res Brain Res Rev* 33: 1-12, 2000; Mudher & Lovestone, *Trends Neurosci* 25: 22-6, 2002; Caricasole et al., *Trends Pharmacol Sci* 24: 233-8, 2003; Moon et al., *Nat Rev Genet* 5: 691-701, 2004; De Ferrari et al., *Mol Psychiatry* 8:

195-208, 2003. In this context, the present results regarding the association of polymorphisms in the LRP6 gene in the sib-pair series—which was originally used to describe the genetic linkage of chromosome 12 to late-onset AD—is the first direct evidence on the involvement of a Wnt signalling component in AD. As such it may well open the door to new insights into the pathological mechanisms of this disorder. Given that the Wnt/β-catenin pathway can be activated pharmacologically (e.g., with lithium), future research will determine whether genetic testing for LRP6 SNPs, and prophylactic treatment of some individuals to augment the activation of Wnt/β-catenin signalling, is warranted as a means to treat or prevent AD. Moon et al., *Nat Rev Genet* 5: 691-701, 2004; De Ferrari et al., *Mol Psychiatry* 8: 195-208, 2003.

Example 2

Methodology

Sample data: Four hundred seventy four families (1372 individuals) corresponding to affected sibling pairs (ASPs) were provided by the National Institute of Mental Health (NIMH), the National Cell Repository for Alzheimer Disease (grant number U24 AG21886) and the United Kingdom. This data set includes many of the families used in Stage I and II late onset AD genomic screens, and more recently ascertained families. Wu et al., *JAMA* 280: 619-22, 1998; Kehoe et al., *Hum Mol Genet* 8: 237-45, 1999; Myers et al., *Am J Med Genet* 114: 235-44, 2002. Each sibling used for analysis had to have an age of onset greater than or equal to 65 years and a diagnosis of definite or probable AD according to NINCDS-ADRDA diagnostic criteria. DNA was extracted from blood or mouth swab samples and informed consent was obtained for all patient samples used in the study according to procedures approved by local and national ethics committees.

Generation of SNP data: Querying dbSNP (NCBI) was used to identify polymorphisms within the LRP6 gene. Non-synonymous coding sequence SNPs were selected for re-sequencing: in exon 7 (SNP 7e; Ile483→Val, id. number rs7975614); in exon 11 (SNP 11e; Ile1062→Val, rs2302686); and in exon 14 (SNP 14e; Cys817→Ser, rs2302685). A synonymous coding sequence SNP in exon 18 was also re-sequenced (SNP 18e; Cys1270→Cys, rs1012672) and a SNP within the boundaries of a putative splicing site in the 5' UTR of exon 16 (SNP 16e, rs2075241). SNPs 14e and 18e were subsequently genotyped by the Pyrosequencing method. Nordstrom et al., *Anal Biochem* 282: 186-93, 2000. Design of primers, PCR cycling, sequencing and Pyrosequencing conditions are given as Supplementary information.

Statistical analysis: In the ASPs sample 14e and 18e were tested for association with AD using the Family-Based Association Test (FBAT; version 1.5.1) package, which includes also haplotype-FBAT (HBAT). Rabinowitz & Laird, *Hum Hered* 50: 211-23, 2000; Lake et al., *Am J Hum Genet* 67: 1515-25, 2000; Horvath et al., *Genet Epidemiol* 26: 61-9, 2004. The sample was analyzed by using an additive model as a whole and two strata based on APOE-ε4 carrier status. The default affected-only analyses was performed, which uses unaffected siblings to provide information about possible parental genotypes, and analyses using an offset equal to 0.5 (i.e. equal weight to each group) to include phenotypic information from unaffected siblings, as it has been described. Saunders et al., *Hum Mol Genet* 12: 2765-76, 2003. Likewise, given that there have been several reports of linkage in this region on chromosome 12, the empirical variance option in FBAT was used. Pericak-Vance et al., *JAMA* 278: 1237-41, 1997; Rogaeva et al., *JAMA* 280: 614-8, 1998; Wu et al., *JAMA* 280: 619-22, 1998; Kehoe et al., *Hum Mol Genet* 8: 237-45, 1999; Scott et al., *Am J Hum Genet* 66: 922-32, 2000; Myers et al., *Am J Med Genet* 114: 235-44, 2002; Mayeux et al., *Am J Hum Genet* 70: 237-43, 2002; Lake et al., *Am J Hum Genet* 67: 1515-25, 2000. In any case, neither the use of the empirical variance option nor the use of an offset=0.5 modified substantially the P value of the FBAT statistic test.

Expression vectors: Plasmid pCDNA3.1 containing Human LRP6 corresponding to allele 14I (determined by sequencing) was used. Brown et al., *Biochem Biophys Res Commun* 248: 879-88, 1998. The COOH-terminal Haemagluttin (HA) tagged hLRP6, hLRP6-HA, was generated by ligating hybridized oligonucleotides to the 3' terminus BsrGI site in hLRP6 and the XbaI site in the pcDNA 3.1 polylinker. The hybridized oligonucleotides contained a BsrGI overhang followed by the remaining 3' hLRP6 sequence (minus stop codon), an HA epitope, a stop codon, and an XbaI overhang. Mutant hLRP6 (14eV)-HA was generated by replacement of an XhoI-XhoI restriction fragment in which the corresponding mutation was engineered by overlap extension PCR-based mutagenesis. All constructs were verified through sequencing.

Cell culture and conditioned media: Human embryonic kidney HEK293T fibroblastic cells and mouse L-cells or L-cells (L-Wnt3a) that stably express Wnt3a were maintained in DMEM medium, 10% foetal bovine serum (Invitrogen) and 100 U/ml pen/strep (Invitrogen). HEK293T/sTF stably expressing the β-catenin responsive superTOPflash luciferase reporter were generated by Lentiviral transduction of HEK293T cells. Robitaille et al., *Nat Genet* 32: 326-30, 2002. HEK293T/sTF cells were transiently transfected with the appropriate constructs using Lipofectamine Plus (Invitrogen) for western blot and luciferase reporter assays.

Wnt3a and control conditioned media were prepared from L-cells and L-Wnt3a cells respectively. Cells were plated at 70% confluence in 150 mm plates. Fresh media was replaced when the cells reached confluence (day 0). Conditioned media was collected and replaced with fresh media every two days for six days. Conditioned media from days 3-4 was used in these experiments.

Luciferase reporter assay and surface protein biotinylation: HEK293T/sTF cells seeded in 6-well plates were transfected with the corresponding amounts of each C-terminal HA-tagged hLRP6 allele and 10 ng of the Renilla luciferase construct, pRLTK (Promega), for normalization. Total DNA in all transfections was brought to 2 µg using pCS2+vector DNA. Immediately following transfection, media was replaced with either complete media (DMEM/10% FBS/100 U/ml pen/strep) or media containing Wnt3a conditioned media diluted 1:5 (Wnt3a conditioned media:complete media). 48 hrs post transfection cells were washed three times with PBS and the cell surface proteins were biotinylated with 30 mg/ml noncleavable sulfo-NHS-biotin in PBS (Pierce Chemical Co.) for 30 min at room temperature. Unreacted biotin was quenched with three washes of TBS containing 10% glycine. Cells were then lysed with 300 µl of passive lysis buffer (Promega) containing 1× complete protease inhibitor cocktail (Roche) for 20 minutes at 4° C. Luciferase reporter activity was measured in duplicate using 5 µl of lysate as described and in accordance with the Dual Luciferase Assay specifications (Promega). Robitaille et al., *Nat Genet* 32: 326-30, 2002. 30 µl of 10× RIPA buffer was added to the remaining lysate for solubilization of membrane proteins. Protein concentration in all samples was determined by Bradford assay (Bio-Rad). Total cellular hLRP6-HA in each sample was determined by SDS-PAGE separation of 10 µg of protein from the whole cell lysate followed by western blot analysis probing with an anti-HA primary antibody (H6908, Sigma). Antibodies were stripped and blots were reprobed with an anti-β-tubulin primary antibody (Sigma) for normalization. From the remaining lysate, 250 µg of total protein from each sample was subjected to an HA immunoprecipitation using 5 µg/ml anti-HA antibody (Sigma) and 30 µl protein G-sepharose beads (Sigma). Immunoprecipitates were washed five times with 1× RIPA and eluted with 30 μl of 100 μg/ml HA peptide (Roche). Eluates were separated by SDS-PAGE, transferred to nitrocellulose and blotted with anti-biotin monoclonal antibody (Sigma). Antibodies were stripped and blots were probed with anti-HA antibody (Sigma).

Western blotting: An equal volume of 2× sample buffer containing 8% β-mercaptoethanol was added to each sample. Samples were heated for 5 minutes at 95° C., separated on a 4-12% gradient SDS-PAGE gel (Criterion, Bio-Rad), and transferred to a nitrocellulose membrane (Trans-Blot transfer media, BioRad). The membrane was blocked with 5% dry milk in TBS/0.1% Tween 20. Blots were probed with primary antibody, washed with TBS/0.1% Tween 20, probed with an HRP-conjugated goat anti primary species secondary antibody, and developed by ECL (Pierce) according to the manufacturer's specifications. Antibody stripping was achieved by incubating blots in TBS/2% SDS containing 7 μl/ml β-mercaptoethanol for 30 minutes followed by six five minute washes with TBS/0.1% Tween 20.

Wnt3a dose response: HEK293T/sTF cells seeded in a 100 mm dishes were transfected with 100 ng pRLTK and 100 ng hLRP6(14eI)-HA, hLRP6(14eV)-HA, or empty vector. The final amount of DNA was increased to a total of 10 μg with pCS2+vector DNA. 48 hours post-transfection, cells were trypsinized and replated in 48 well plates. 24 hours later the media was replaced with serial dilutions of Wnt3a conditioned media. The cells were lysed with 50 μl passive lysis buffer (Promega) and luciferase activity was measured in duplicate. Expression of hLRP6(14eI)-HA and hLRP6 (14eV)-HA was determined by western blot analysis using an anti-HA primary antibody (Sigma) and normalized to β-tubulin.

the genomic sequence flanking each exon to yield products between 200 and 400 bp in length by using Primer 3 (http://frodo.wi.mit.edu/cgi-bin/primer3/primer3_www.cgi) (See Table 2). PCR amplification was performed with Thermo-Start DNA Polymerase mix (ABgene), 5 μM each primer and 50 ng human genomic DNA in a 15-μl reaction. Cycling was conducted on a Hybaid-MBS Satellite Thermal Cycler (Thermo Electron Corporation) with an initial denaturation of 94° C. for 15 min followed by 35 cycles of 94° C. for 30 s, appropriate annealing temperature for 30 s and 68° C. for 45 s, with a final extension step of 68° C. for 10 min. Sized PCR products were confirmed by electrophoresis on 2% agarose gels. PCR purification was achieved using the Montage PCR96 Cleanup Kit (Millipore). Purified products were then bidirectionally sequenced on an ABI3700 DNA Sequencer (Applied Biosystems) with the Big Dye Terminator (v3.1) Cycle Sequencing Kit (Applied Biosystems). Sequence traces were analysed on Sequencher 4.0.5 (Gene Codes Corporation) to characterize polymorphisms. To ensure consistent and high-quality genotyping data, negative control samples were included in every genotyping experiment. In addition, near 5% of the samples were genotyped in duplicate and the genotypes of the duplicate samples were checked for consistency.

TABLE 2

PCR Primers for Sequencing

| PRIMER ID | FORWARD | SIZE | TM | REVERSE | SIZE | TM | Product size (nt) |
|---|---|---|---|---|---|---|---|
| lrp6_7e | AGGGATGGATCTCACCTTTAGAATA SEQ ID NO: 18 | 25 | 60.53 | CATTATACTGTCGACTCAAAACCCATT SEQ ID NO: 23 | 27 | 62.58 | 318 |
| lrp6_11e | CATGAATATGACTCTTTCCCCCAGA SEQ ID NO: 19 | 25 | 64.49 | ACCAATGATAAATAGCAGCCACTGA SEQ ID NO: 24 | 25 | 63.06 | 329 |
| lrp6_14e | ATTGTGACTGATTGCCTCAGGGTTA SEQ ID NO: 20 | 25 | 65.05 | TAACAGGCTGAAAAAGAAGGGTGAG SEQ ID NO: 25 | 25 | 63.98 | 355 |
| lrp6_16e | TGACCCACATGAGTCATTTCTGTTG SEQ ID NO: 21 | 25 | 65.42 | TTCCTCCAATTAGCTTTATCCCATT SEQ ID NO: 26 | 25 | 62.26 | 300 |
| lrp6_18e | GTCACTCCCCTTCTCCTTGTTCATT SEQ ID NO: 22 | 25 | 64.98 | GGCACTGAAGAATTCTGGATACCTT SEQ ID NO: 27 | 25 | 63.01 | 289 |

PCR PRIMERS FOR PYROSEQUENCING

| PRIMER ID | FORWARD | SCORE | RATING |
|---|---|---|---|
| lrp6_14e-PYRO | GACAGACCTCGAGCC SEQ ID NO: 28 | 100 | high |
| lrp6_18e-PYRO | TGGCTTGGCGGTG SEQ ID NO: 29 | 100 | high |

Example 3

Re-Sequencing Exons 7, 11, 14 and 18, and 5'UTR of Exon 16 or LRP6

PCR primers (Operon-Qiagen) were designed to amplify each axon plus at least 40 bp upstream and downstream from Quantitative RT-PCR. Normal human hippocampus polyA-mRNA was purchased from BD Biosciences. cDNA was synthesized with oligodT primers from 500 ng of mRNA using SuperseriptIII (Invitrogen). Real-time PCR was performed using the Roche Light Cycler 1.2 and software, version 3.5 (Roche Diagnostics). Intron-spanning primers (LRP5 forward 5'-ACTCAGAGACCAACCGCATC-3'(SEQ ID NO: 30), reverse 5'-TCC ATT GGG CCA GTA AAT GT-3' (SEQ ID NO: 31); LRP6 forward 5'-CAT GTG ATT GGC TTG GAG AA-3' (SEQ ID NO: 32), reverse 5'-CGA CTT GAA CCA TCC ATT CC-3' (SEQ ID NO: 33), β-actin forward 5'-AGA GCA AGA GAG GCA TCC TC-3' (SEQ ID NO: 34), reverse 5'-CTC AAA CAT GAT CTG GGT CA-3' (SEQ ID NO: 35) were designed to amplify ~200 bp products in order to minimize contamination from genomic DNA.

Quantitative PCR was performed in triplicate using the Fast-Start SyBr Green DNA MasterMix Plus, as directed by the manufacturer (Roche Diagnostics). Primers were annealed at 58° C. Absolute transcript copy number was determined by comparing the gene amplification in hippocampus cDNA to the amplification of standard samples containing $10^2$ to $10^8$ copies of the gene. The absolute copy number of LRP5 and LRP6 was calculated by dividing the average copy number of triplicate quantitations to the average copy number of β-actin. The error bars represent the standard error of the ratios, as calculated using a confidence interval.

Each recited range includes all combinations and sub-combinations of ranges, as well as specific numerals contained therein.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed:

1. A method of predicting late onset Alzheimer's disease in an APOE-ε4 negative human subject with a sibling affected by Alzheimer's Disease, said method comprising:
   providing a sample from the APOE-ε4 negative human subject with a sibling affected by Alzheimer's Disease;
   determining, in a nucleic acid molecule corresponding to SEQ ID NO: 1, which is from the sample, the presence of an A to G substitution at nucleotide position 3184; and
   predicting, based on said determining, late onset of Alzheimer's disease in the human subject.

2. The method of claim 1 wherein said determining comprises:
   sequencing the nucleic acid molecule corresponding to SEQ ID NO: 1 to determine the nucleotide at position 3184.

3. The method of claim 1, wherein the step of determining, in a nucleic acid molecule corresponding to SEQ ID NO: 1, which is from the sample, the presence of an A to G substitution at nucleotide position 3184, is carried out by techniques of polymerase chain reaction, hybridization, Southern blotting onto a membrane, digestion with nucleases, restriction fragment length polymorphism, direct sequencing, or combinations thereof.

4. The method of claim 3, wherein the determining step comprises:
   isolating DNA from the sample and
   amplifying the isolated DNA using primers capable of amplifying the sequence comprising an A to G substitution at nucleotide 3184 in a nucleic acid molecule corresponding to SEQ ID NO:1.

5. A method of detecting an increased susceptibility to late onset Alzheimer's disease in an APOE-ε4 negative human subject with a sibling affected by Alzheimer's Disease comprising:
   analyzing a DNA sample from the APOE-ε4 negative human subject with a sibling affected by Alzheimer's Disease for the presence of an A to G substitution at nucleotide position 3184 in a nucleic acid molecule corresponding to SEQ ID NO: 1, wherein the presence of the A to G substitution at nucleotide position 3184 in a nucleic acid molecule corresponding to SEQ ID NO: 1 is indicative of an increased susceptibility to late onset Alzheimer's disease.

6. The method of claim 5, further comprising:
   performing a pedigree analysis by analyzing DNA samples obtained from family members of the APOE-ε4 negative human subject with a sibling affected by Alzheimer's Disease for the presence of the A to G substitution at nucleotide position 3184 in a nucleic acid molecule corresponding to SEQ ID NO: 1.

7. A method for predicting late onset Alzheimer's disease, wherein the method utilizes a single-stranded conformation polymorphism assay comprising:
   providing a sample from the APOE-ε4 negative human subject with a sibling affected by Alzheimer's Disease;
   sequencing, in the sample, a human LRP6 gene or fragment thereof which contains, in a nucleotide sequence corresponding to SEQ ID NO: 1, position 3184;
   hybridizing an allele specific probe to the LRP6 gene or fragment thereof;
   amplifying a human LRP6 gene or fragment thereof;
   cutting the amplified human LRP6 gene or fragment thereof with a restriction enzyme to produce a restriction pattern; and
   analyzing the restriction pattern, wherein the presence of an A to G substitution at nucleotide position 3184 in a nucleic acid molecule corresponding to SEQ ID NO: 1 is predictive of late onset Alzheimer's disease.

* * * * *